US008883981B2

(12) United States Patent
Shitara et al.

(10) Patent No.: US 8,883,981 B2
(45) Date of Patent: *Nov. 11, 2014

(54) RECOMBINANT ANTIBODY COMPOSITION

(75) Inventors: Kenya Shitara, Machida (JP); Rinpei Niwa, Machida (JP); Akito Natsume, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 143 days.

This patent is subject to a terminal disclaimer.

(21) Appl. No.: 12/829,836

(22) Filed: Jul. 2, 2010

(65) Prior Publication Data

US 2011/0009600 A1 Jan. 13, 2011

Related U.S. Application Data

(63) Continuation of application No. 11/491,501, filed on Jul. 24, 2006, now Pat. No. 7,923,538.

(60) Provisional application No. 60/701,477, filed on Jul. 22, 2005, provisional application No. 60/791,213, filed on Apr. 12, 2006.

(30) Foreign Application Priority Data

Jul. 22, 2005 (JP) ................................. 2005-212979
Apr. 11, 2006 (JP) ................................. 2006-108216

(51) Int. Cl.
C12P 21/08 (2006.01)
C07K 16/28 (2006.01)
A61K 39/00 (2006.01)

(52) U.S. Cl.
CPC ....... *C07K 16/2887* (2013.01); *A61K 2039/505* (2013.01); *C07K 2317/24* (2013.01); *C07K 2317/72* (2013.01); *C07K 2317/732* (2013.01); *C07K 2317/734* (2013.01)
USPC ..................................................... 530/387.3

(58) Field of Classification Search
None
See application file for complete search history.

(56) References Cited

U.S. PATENT DOCUMENTS

| | | | |
|---|---|---|---|
| 6,737,056 B1 | 5/2004 | Presta | |
| 7,297,775 B2 | 11/2007 | Idusogie et al. | |
| 7,923,538 B2 * | 4/2011 | Shitara et al. | 530/387.3 |
| 2003/0158389 A1 | 8/2003 | Idusogie et al. | |
| 2005/0208519 A1 | 9/2005 | Liew et al. | |
| 2007/0111281 A1 | 5/2007 | Sondermann et al. | |
| 2007/0148165 A1* | 6/2007 | Shitara et al. | 424/133.1 |

FOREIGN PATENT DOCUMENTS

| | | |
|---|---|---|
| EP | 1443961 A2 | 8/2004 |
| WO | 02/056910 A1 | 7/2002 |
| WO | 03/035835 A2 | 5/2003 |
| WO | 2006/020114 A2 | 2/2006 |

OTHER PUBLICATIONS

Natsume, Can. Res. 68:3863-3872, 2008.*
J. Amaral et al., "Study on the scale-up of human IgG3 purification using protein A affinity chromatography", Bioseparation, 2002, 10: 139-143.
Ole H. Brekke et al., "Human IgG3 can adopt the disulfide bond pattern characteristic for IgG1 without resembling it in complement mediated cell lysis", Molecular Immunology, 1993, 30(16): 1419-1425.
Elvin A. Kabat et al., "Sequences of Proteins of Immunological Interest", 1987, 4th Edition, pp. 307-308.
Fumiki Kushihata et al., "Human Leukocyte Antigen Antibodies and Human Complement Activation: Role of IgG Subclass, Specificity, and Cytotoxic Potential", Transplantation, 2004, 78(7): 995-1001.
Corneliu Medesan et al., "Delineation of the Amino Acid Residues Involved in Transcytosis and Catabolism of Mouse IgG1", The Journal of Immunology, 1997, 158(5): 2211-2217.
T.E. Michaelsen et al., "Enhancement of Complement Activation and Cytolysis of Human IgG3 by Deletion of Hinge Exons", Scandinavian Journal of Immunology, 1990, 32: 517-528.
Rinpei Niwa et al. "Enhancement of the Antibody-Dependent Cellular Cytotoxicity of Low-Fucose IgG1 Is Independent of FcγRIIIa Functional Polymorphism", Clinical Cancer Research, 2004, 10(18): 6248-6255.
Lars Norderhaug et al., "Chimeric mouse human IgG3 antibodies with an IgG4-like hinge region induce complement-mediated lysis more efficiently than IgG3 with normal hinge", European Journal of Immunology, 1991, 21: 2379-2384.
Akira Okazaki et al., "Fucose Kesshitsu ni yoru Kotai Efector Kassei no Kojo", Seikagaku, 2005, 77: 45-50.
Robert L. Shields, et al.; "Lack of Fucose on Human IgG1 N-Linked Oligosaccharide Improves Binding to Human FcγRIII and Antibody-dependent Cellular Toxicity", Journal of Biological Chemistry, 2002, 277(30): 26733-26740.
Toyohide Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, 2003, 278(5): 3466-3473.

(Continued)

Primary Examiner — Brad Duffy
(74) Attorney, Agent, or Firm — Sughrue Mion, PLLC

(57) ABSTRACT

The present invention relates to a recombinant antibody composition having higher complement-dependent cytotoxic activity than a human IgG1 antibody and a human IgG3 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al.; a DNA encoding the antibody molecule or a heavy chain constant region of the antibody molecule contained in the recombinant antibody composition; a transformant obtainable by introducing the recombinant vector into a host cell; a process for producing the recombinant antibody composition using the transformant; and a medicament comprising the recombinant antibody composition as an active ingredient.

6 Claims, 29 Drawing Sheets

(56) References Cited

OTHER PUBLICATIONS

Mi-Hua Tao et al., "Structural Features of Human Immunoglobulin G that Determine Isotype-specific Differences in Complete Activation", Journal of Experimental Medicine, 1993, 178: 661-667.

Jessica L. Teeling et al., "Characterization of new human CD20 monoclonal antibodies with potent cytolytic activity against non-Hodgkin lymphomas", Blood, 2004, 104: 1793-1800.

Naoko Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity", Biotechnology and Bioengineering, 2004, 87(5): 614-622.

Tonetti, M. et al. "Synthesis of GDP-L-fucose by the Human FX Protein", The Journal of Biological Chemistry, Nov. 1, 1995 vol. 271, No. 44, pp. 27274-27279.

Idusogie, E. et al. "Engineered Antibodies with Increased Activity to Recruit Complement", The Journal of Immunology, 2001, 166: pp. 2571-2575.

Tao, M. et al. "The Differential Ability of Human IgG1 and IgG4 to Activate Complement Is Determined by the COOH-terminal Sequence of the CH2 Domain", J. Exp. Med. vol. 173, Apr. 1, 1991, pp. 1025-1028.

Bruggemann, M. et al. "Comparison of the Effector Functions of Human Immunoglobulins Using a Matched Set of Chimeric Antibodies", J. Exp. Med. vol. 166 Nov. 1987, pp. 1351-1361.

Schumaker, V. et al. "Ultracentrifuge Studies of the Binding of IgG of Different Subclasses to the C1q Subunit of the First Component of Complement", Biochemistry 1976, vol. 15, No. 23, pp. 5175-5181.

Ohyama, C. et al. "Molecular Cloning and Expression of GDP-D-mannose-4,6-dehydratase, a Key Enzyme for Fucose Metabolism Defective in Lec13 Cells", The Journal of Biological Chemistry, Jun. 5, 1998, vol. 273, No. 23. pp. 14582-14587.

Japanese Patent Office, Office Action dated Feb. 21, 2012 issued in Japanese Application No. 2007-526072.

* cited by examiner

Fig. 1

```
        CH1
       ┌──────►
       |120      130        140        150        160        170
IgG1   ASTKGPSVFPLAPSSKSTSGGTAALGCLVKDYFPEPVTVSWNSGALTSGVHTFPAVLQSS    SEQ ID NO: 76
IgG2   ASTKGPSVFPLAPCSRSTSESTAALGCLVKDYFPEPVTVSWNSGALTSGVHTFPAVLQSS    SEQ ID NO: 77
IgG3   ASTKGPSVFPLAPCSRSTSGGTAALGCLVKDYFPEPVTVSWNSGALTSGVHTFPAVLQSS    SEQ ID NO: 78
IgG4   ASTKGPSVFPLAPCSRSTSESTAALGCLVKDYFPEPVTVSWNSGALTSGVHTFPAVLQSS    SEQ ID NO: 79
       ************.*.***  ****************************************
                                                      Hinge
                                                     ┌──────►
         180        190        200        210        220
IgG1   GLYSLSSVVTVPSSSLGTQTYICNVNHKPSNTKVDKKVEPKSCDKTHT------------    SEQ ID NO: 76
IgG2   GLYSLSSVVTVPSSNFGTQTYTCNVDHKPSNTKVDKTVERKCCVE---------------    SEQ ID NO: 77
IgG3   GLYSLSSVVTVPSSSLGTQTYTCNVNHKPSNTKVDKRVELKTPLGDTTHTCPRCPEPKSC    SEQ ID NO: 78
IgG4   GLYSLSSVVTVPSSSLGTKTYTCNVDHKPSNTKVDKRVESKYGPP---------------    SEQ ID NO: 79
       **************..**.**.*** *********** ** *
                                                  CH2
                                                 ┌──────►
                                                 230        240        250
IgG1   --------------------------------CPPCPAPELLGGPSVFLFPPKPKDT      SEQ ID NO: 76
IgG2   --------------------------------CPPCPAPPVA-GPSVFLFPPKPKDT      SEQ ID NO: 77
IgG3   DTPPPCPRCPEPKSCDTPPPCPRCPEPKSCDTPPPCPRCPAPELLGGPSVFLFPPKPKDT    SEQ ID NO: 78
IgG4   --------------------------------CPSCPAPEFLGGPSVFLFPPKPKDT      SEQ ID NO: 79
                                       ** ****. ..**************

260        270        280        290        300        310
IgG1   LMISRTPEVTCVVVDVSHEDPEVKFNWYVDGVEVHNAKTKPREEQYNSTYRVVSVLTVLH    SEQ ID NO: 76
IgG2   LMISRTPEVTCVVVDVSHEDPEVQFNWYVDGVEVHNAKTKPREEQFNSTFRVVSVLTVVH    SEQ ID NO: 77
IgG3   LMISRTPEVTCVVVDVSHEDPEVQFKWYVDGVEVHNAKTKPREEQFNSTFRVVSVLTVLH    SEQ ID NO: 78
IgG4   LMISRTPEVTCVVVDVSQEDPEVQFNWYVDGVEVHNAKTKPREEQFNSTYRVVSVLTVLH    SEQ ID NO: 79
       *****************.*****.*.**********.*****************.*
                                  CH3
                                 ┌──────►
         320        330        340        350        360        370
IgG1   QDWLNGKEYKCKVSNKALPAPIEKTISKAKGQPREPQVYTLPPSRDELTKNQVSLTCLVK    SEQ ID NO: 76
IgG2   QDWLNGKEYKCKVSNKGLPAPIEKTISKTKGQPREPQVYTLPPSREEMTKNQVSLTCLVK    SEQ ID NO: 77
IgG3   QDWLNGKEYKCKVSNKALPAPIEKTISKTKGQPREPQVYTLPPSREEMTKNQVSLTCLVK    SEQ ID NO: 78
IgG4   QDWLNGKEYKCKVSNKGLPSSIEKTISKAKGQPREPQVYTLPPSQEEMTKNQVSLTCLVK    SEQ ID NO: 79
       ***************.**..*******.****************..*.************

380        390        400        410        420        430
IgG1   GFYPSDIAVEWESNGQPENNYKTTPPVLDSDGSFFLYSKLTVDKSRWQQGNVFSCSVMHE    SEQ ID NO: 76
IgG2   GFYPSDIAVEWESNGQPENNYKTTPPMLDSDGSFFLYSKLTVDKSRWQQGNVFSCSVMHE    SEQ ID NO: 77
IgG3   GFYPSDIAVEWESSGQPENNYNTTPPMLDSDGSFFLYSKLTVDKSRWQQGNIFSCSVMHE    SEQ ID NO: 78
IgG4   GFYPSDIAVEWESNGQPENNYKTTPPVLDSDGSFFLYSRLTVDKSRWQEGNVFSCSVMHE    SEQ ID NO: 79
       *************.*******.****.***********.********.**.********

440
IgG1   ALHNHYTQKSLSLSPGK    SEQ ID NO: 76
IgG2   ALHNHYTQKSLSLSPGK    SEQ ID NO: 77
IgG3   ALHNRFTQKSLSLSPGK    SEQ ID NO: 78
IgG4   ALHNHYTQKSLSLSLGK    SEQ ID NO: 79
       ****..********.**
```

● : N-acetylglucosamine (GlcNAc)

☐ : Mannose

■ : Galactose

☆ : Fucose

Fig. 9
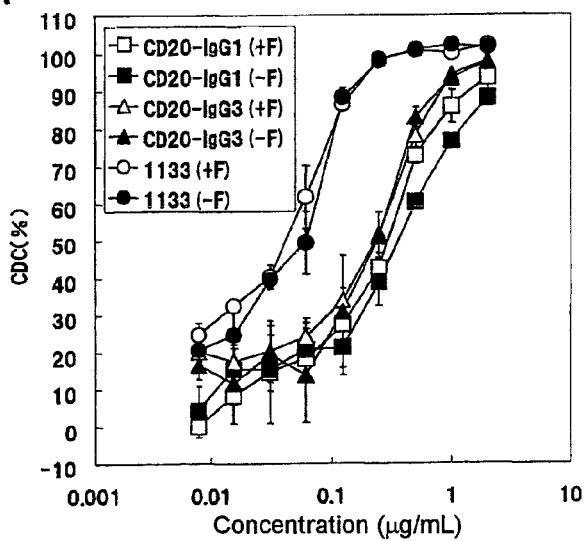
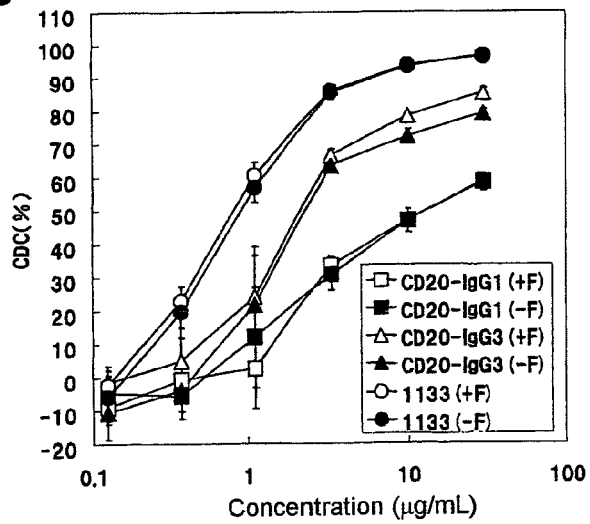

FIG. 12
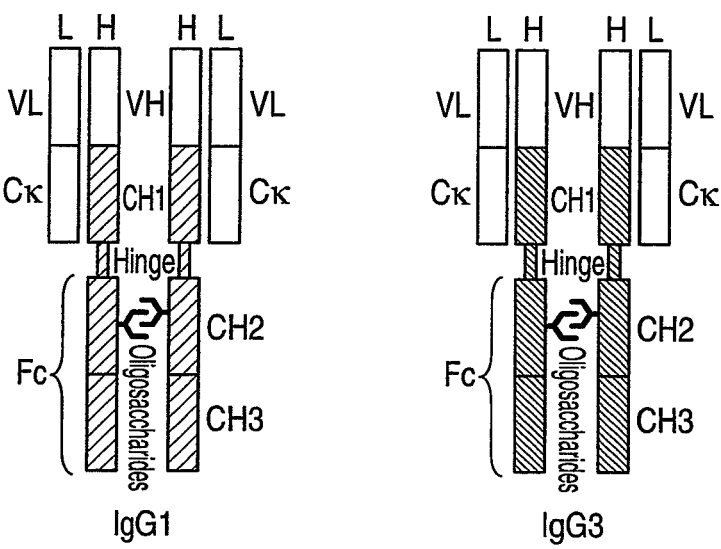
IgG1    IgG3
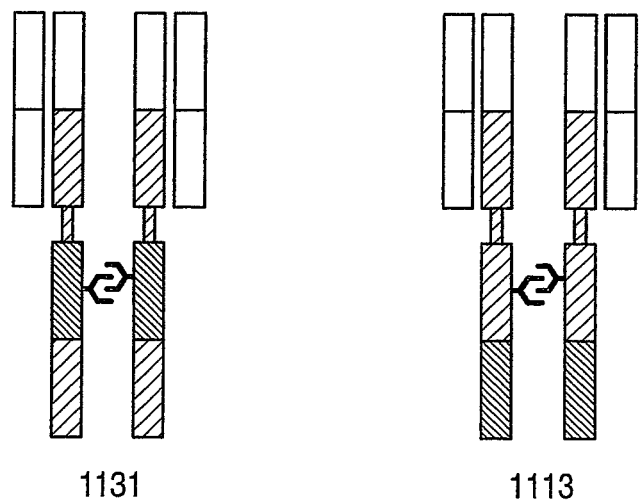
1131    1113

Fig. 18
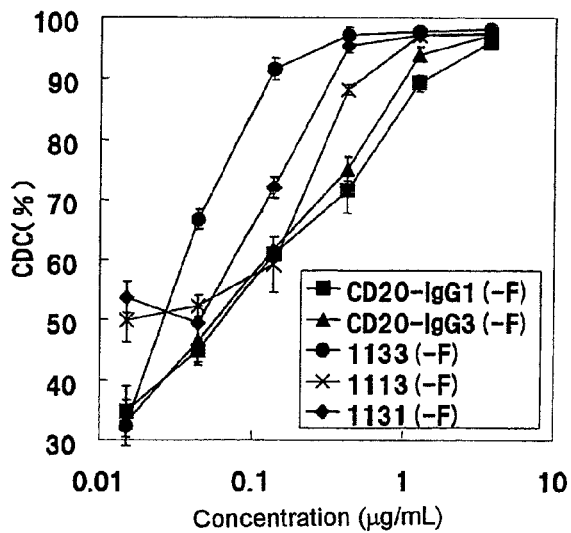
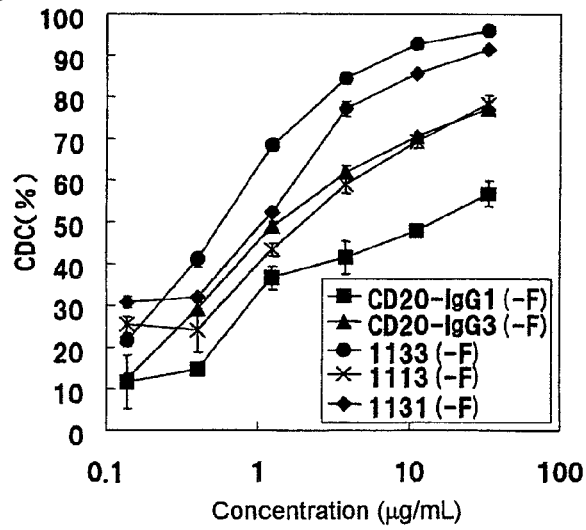

RECOMBINANT ANTIBODY COMPOSITION

CROSS REFERENCES

This is a continuation application of U.S. patent application Ser. No. 11/491,501, filed Jul. 24, 2006, which is based on U.S. Provisional Patent Application No. 60/701,477 filed Jul. 22, 2005 and 60/791,213 filed Apr. 12, 2006, and Japanese Patent Applications No. 2005-212979 filed Jul. 22, 2005, and 2006-108216 filed Apr. 11, 2006, the entire contents of which are incorporated hereinto by reference. All references cited herein are incorporated in their entirety.

FIELD OF THE INVENTION

The present invention relates to a recombinant antibody composition having higher complement-dependent cytotoxic activity than a human IgG1 antibody and a human IgG3 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al. (hereinafter referred to as EU index); a DNA encoding the antibody molecule or a heavy chain constant region of the antibody molecule contained in the recombinant antibody composition; a transformant obtainable by introducing the DNA into a host cell; a process for producing the recombinant antibody composition using the transformant; and a medicament comprising the recombinant antibody composition as an active ingredient.

BACKGROUND OF THE INVENTION

Since antibodies have high binding activity, binding specificity and high stability in blood, applications thereof to diagnostic, preventive and therapeutic agents for various human diseases have been attempted (Non-patent Reference 1). In addition, human chimeric antibodies or humanized antibodies have been prepared from non-human animal antibodies using gene recombination techniques (Non-patent References 2 to 5). The human chimeric antibody is an antibody in which its variable region is an antibody of non-human animal and its constant region is a human antibody. The humanized antibody is an antibody in which the complementarity determining region (hereinafter referred to as CDR) of a non-human animal is replaced by CDR of a human antibody.

The human chimeric antibodies and humanized antibodies have resolved problems possessed by mouse antibodies and the like, such as the high immunogenicity, low effector function and short blood half-life of non-human animal antibodies, and applications of monoclonal antibodies to pharmaceutical preparations were made possible by using them (Non-patent References 6 to 9). In the Unites States, for example, plurality of humanized antibodies have already been approved as an antibody for cancer treatment, and on the market (Non-patent Reference 10).

These human chimeric antibodies and humanized antibodies actually show effects to a certain degree at clinical level, but therapeutic antibodies having higher effects are in demand. For example, in the case of single administration of Rituxan™ (Non-patent Reference 11) (manufactured by IDEC/Roche/Genentech) which is a human chimeric antibody to CD20, it has been reported that its response ratio for recurrent low malignancy non-Hodgkin lymphoma patients by the phase III clinical test is no more than 48% (complete remission 6%, partial remission 42%), and its average duration of response is 12 months (Non-patent Reference 12). In the case of combination use of Rituxan™ and chemotherapy (CHOP: Cyclophosphamide, Doxorubicin, Vincristine), it has been reported that its response ratio for recurrent low malignancy and follicular non-Hodgkin lymphoma patients by the phase II clinical test is 95% (complete remission 55%, partial remission 45%), but side effects due to CHOP were found (Non-patent Reference 13). In the case of single administration of Herceptin™ (manufactured by Genentech) which is a humanized antibody to HER2, it has been reported that its response ratio for metastatic breast cancer patients by the phase III clinical test is only 15%, and its average duration of response is 9.1 months (Non-patent Reference 14).

The human antibody molecule is also called immunoglobulin (hereinafter referred to as Ig) and classified into respective classes of IgA, IgD, IgE, IgG and IgM based on its molecular structure. The antibody molecule of human IgG (hereinafter referred to as IgG) mainly used as the therapeutic antibody is formed by two respective polypeptides called heavy chain (hereinafter referred to as H chain) and light chain (hereinafter referred to as L chain). The H chain is formed by respective domain structures called H chain variable region (hereinafter referred to as VH), CH1, hinge, CH2 and CH3, from the N-terminal side. The respective domains CH1, hinge, CH2 and CH3 are also called heavy chain constant region as a whole (hereinafter referred to as CH), and the CH2 and CH3 domains are also called Fc region as a whole. The L chain is formed by respective domain structures called L chain variable region (hereinafter referred to as VL) and L chain constant region (hereinafter referred to as CL), from the N-terminal side.

Four subclasses including IgG1, IgG2, IgG3 and IgG4 exist in the IgG antibody H chain. The H chains of respective IgG subclasses mutually have about 95% homology of amino acid sequence in the constant region excluding the hinge which is rich in variability (FIG. 1).

Regardless of the high homology of amino acid sequences in respective IgG subclasses, height of the biological activity possessed thereby varies (Non-patent Reference 15). The biological activity includes effector functions such as complement-dependent cytotoxic activity (hereinafter referred to as CDC), antibody-dependent cell-mediated cytotoxic activity (hereinafter referred to as ADCC) and phagocytotic activity, and these functions play an important role in the living body, such as exclusion of foreign matters and pathogens.

A family of Fcγ receptor (hereinafter referred to as FcγR) are expressed on the surface of various leukocytes such as natural killer cell (hereinafter referred to as NK cell), monocyte, macrophage and granulocyte. The FcγR is classified into active type FcγR including FcγRI, FcγRIIa, FcγRIIIa and FcγRIIIb and suppression type FcγR of FcγRIIb. IgG antibodies, particularly IgG1 and IgG3 in human, strongly bind to these receptors and induce ADCC activity and phagocytotic activity by leukocytes as a result.

The ADCC activity is a cytolytic reaction in which an antibody bound to its antigen binds to mainly FcγRIIIa on the NK cell surface via Fc moiety, and as a result, the reaction is generated by cytotoxic molecules, such as perforin and granzyme, released from the NK cell (Non-patent References 16 and 17). The grade of the ADCC activity is generally in order of IgG1>IgG3>>IgG4≥IgG2 (Non-patent References 18 and 19).

The CDC activity is a reaction in which an antibody bound to its antigen activates reaction cascade of a group of serum proteins, called serum complement system, and finally lyses the target cell. The CDC activity is high in human IgG1 and IgG3, and the grade is generally in order of IgG3≥IgG1>>IgG2≈IgG4. The complement system is classified into respective components of C1 to C9, and most of them are enzyme precursors which express enzyme activities by partial degradation. The CDC activity starts with the binding of C1q as a component of C1 to the Fc region of an antibody on the target cell, each of the subsequent components is partially degraded by the former step component to advance cascade of the activation, and finally, C5 to C9 form a pore-forming polymer called membrane attacking complex on the cell membrane of the target cell to cause the cell lysis reaction (Non-patent References 16 and 17).

Importance of the above-described effector functions is also recognized on the mechanism of action of therapeutic antibodies used in the clinical field. The above-described Rituxan™ is a human chimeric antibody of IgG1 subclass, and not only it shows ADCC activity and CDC activity in vitro (Non-patent Reference 21) but it has also been suggested on its clinical effects that Rituxan™ actually exerts effector functions in the body of patients, because of the facts that its therapeutic affect is high in the patients showing a genotype of strong ADCC activity (Non-patent Reference 22), that the complement components are quickly consumed from blood after its administration (Non-patent Reference 23), and that expression of CD59 as a factor for suppressing CDC activity increases in cancer cells of relapsed patients after its administration (Non-patent Reference 24). Herceptin™ is also a humanized antibody of IgG1 subclass, and it has been reported that it has ADCC activity in vitro (Non-patent Reference 25).

Based on the above, human IgG1 antibodies are most suitable as therapeutic antibodies, because they have higher ADCC activity and CDC activity and also have longer half-life in human blood than other subclasses.

In order to analyze functions of IgG antibodies, studies have been carried out for the preparation of antibodies in which the domain units were swapped among different IgG subclasses. In the latter half of 1980s, Morrison et al. have pointed out that antibody molecules in which respective domains (CH1, CH2, CH3, hinge) of the heavy chain constant region were swapped between IgG1 and IgG4, or between IgG2 and IgG3, can be expressed as recombinant proteins, and that antibodies in which the hinges of IgG3 and IgG4 were mutually swapped do not show changes in the respective complement fixation capacity and Fc receptor binding ability of the original antibodies (Patent Reference 1). Thereafter, they have examined these domain-swapped antibodies of IgG1 with IgG4 and IgG2 with IgG3 and shown as a result that the C-terminal side of CH2 is important for the CDC activity of IgG1, and CH2 for the CDC activity of IgG3 (Non-patent Reference 26), and that the CH2 domain and hinge are important for the binding of IgG1 and IgG3 to FcγRI which is one of the Fc receptors (Non-patent Reference 27).

It is known that C1q binds to the Fc region of antibody molecules. Binding constants (Ka) of C1q for monomers of human IgG1, IgG2, IgG3 and IgG4 are $1.2 \times 10^4$, $0.64 \times 10^4$, $2.9 \times 10^4$ and $0.44 \times 10^4$ $M^{-1}$, respectively (Non-patent Reference 20). As described in the above, the CH2 domain is particularly important in the Fc region (Non-patent Reference 26), and more illustratively, it is known that, according to the definition of EU index by Kabat et al. (Non-patent Reference 28), Leu 235 (Non-patent Reference 29) and Asp 270, Lys 322, Pro 329 and Pro 331 (Non-patent Reference 30) in the CH2 are important in the case of human IgG1, and Glu 233, Leu 234, Leu 235 and Gly 236 (Non-patent Reference 31) and Lys 322 (Non-patent Reference 32) in the case of human IgG3.

Attempts have been made to further enhance CDC activity by replacing a part of the amino acid sequence of heavy chain constant region of human IgG3, as a subclass having the highest CDC activity, by an amino acid sequence from other subclass. Regarding hinge lengths of respective IgG subclasses, IgG1 has 15 amino acids, IgG2 has 12 amino acids, IgG3 has 62 amino acids, and IgG4 has 12 amino acids, so that the human IgG3 has a structural characteristic that its hinge region is longer than other IgG subclasses (Non-patent Reference 1). Michaelsen et al. have pointed out that CDC activity of an Ig, in which the 62 amino acids of the hinge of wild type human IgG3 polypeptide were shortened to 15 amino acids by deleting 3 exons of the N-terminal side, exceeds those of IgG3 and IgG1 (Non-patent Reference 33). In addition, Norderhaug et al. have pointed out that the CDC activity is further enhanced when the amino acid sequence of the above-described shortened hinge is allowed to approximate the amino acid sequence of the hinge of IgG4 (Non-patent Reference 34). Also, Brekke et al. have pointed out that in an IgG3 in which its hinge part is replaced by IgG1, and the hinge part, and an IgG3 in which an N-terminal moiety of CH1 is replaced by IgG1, the CDC activity is higher than that of IgG3 and becomes equal to or higher than that of IgG1 (Non-patent Reference 35).

In addition, attempts have also been made to enhance the CDC activity by preparing modified forms of IgG by introducing mutation in all sorts of amino acid sequence in the human IgG heavy chain constant regions, and increasing the binding activity of these modified forms to C1q. Idusogie et al. have reported that the CDC activity is enhanced approximately by 2-fold at the maximum by replacing when Lys at position 326 or Glu at position 333 indicated by the EU index in the CH2 domain in the heavy chain constant region of an anti-CD20 chimeric antibody Rituxan™ having human IgG1 constant region and mouse-derived variable region is replaced by other amino acid (Non-patent Reference 36, Patent Reference 2). Idusogie et al. also have pointed out that the CDC activity of IgG2, which is approximately one-to-several hundreds of the CDC activity of IgG1, increases to about ½ of the CDC activity of IgG1, when Lys at position 326 or Glu at position 333 indicated by the EU index is replaced by other amino acid (Patent References 3 to 5).

FcγR-dependent activity such as ADCC activity or phagocytic activity and CDC activity are both important for the therapeutic effect of therapeutic antibodies. However, since both of the C1q binding as the early stage for inducing CDC activity and the binding to FcγR as the early stage for inducing ADCC activity mediate the antibody Fc, there is a possibility that the ADCC activity is reduced when the CDC activity is enhanced. Idusogie et al. have reported that a point mutation-introduced mutant of Fc amino acids of CDC activity-enhanced IgG shows sharply reduced ADCC activity (Non-patent Reference 36).

Also, it is known that the ADCC activity of an antibody having a human IgG constant region changes by the structure of the complex type N-glycoside-linked sugar chain (its schematic illustration is shown in FIG. 2) to be added to asparagine at position 297 in the CH2 domain (Patent Reference 6). Although there are reports stating that the ADCC activity of antibodies changes depending on the contents of galactose and N-acetylglucosamine in the sugar chain to be bound to the antibody (Non-patent References 37 to 40), the substance which mostly influences on the ADCC activity is a fucose bound to N-acetylglucosamine in the reducing terminal through α1,6 bond. An IgG antibody having a complex type N-glycoside-linked sugar chain in which fucose does not bind to N-acetylglucosamine in the reducing terminal shows remarkably higher ADCC activity than that of an IgG antibody having a complex type N-glycoside-linked sugar chain in which fucose is bound to N-acetylglucosamine in the reducing terminal (Non-patent References 41 and 42, Patent Reference 7). Cells in which the α1,6-fucosyltransferase gene was knocked out are known as the cell which produces an antibody composition having a complex type N-glycoside-linked sugar chain in which fucose is not bound to N-acetylglucosamine in the reducing terminal (Patent References 7 and 8).

Since human IgG3 does not have binding activity to protein A unlike other subclasses (Non-patent Reference 1), it is difficult to purify it when produced as a medicine. It is known that IgG molecules associate with protein A at the interface of CH2 domain and CH3 domain, illustratively, it has been suggested based on an X-ray crystallography that a loop moiety containing amino acids of positions 252 to 254 and positions 308 to 312 indicated by the EU index in the immunoglobulin structure (immunoglobulin fold) of CH2 and positions 433 to 436 in the immunoglobulin structure of CH3 is important (Non-patent Reference 43). It was further shown by a nuclear magnetic resonance method (NMR method) that Ile 253, Ser 254, His 310 and Gln 311 in the CH2 and His 433, His 435 and His 436 in the CH3 of IgG 1 are important (Non-patent Reference 44). In addition, Kim et al. have found that the binding activity to protein A is decreased when His 435 in the human IgG1 heavy chain constant region is replaced with Arg derived from IgG3 (Non-patent Reference 45).

(Non-patent reference 1) *Monoclonal Antibodies: Principles and Applications*, Wiley-Liss, Inc. (1995)
(Non-patent reference 2) *Nature*, 312, 643 (1984)
(Non-patent reference 3) *Proc. Natl. Acad. Sci. USA*, 81, 6851 (1984)
(Non-patent reference 4) *Nature*, 321, 522 (1986)
(Non-patent reference 5) *Nature*, 332, 323 (1988)
(Non-patent reference 6) *Immunol. Today*, 21, 364 (2000)
(Non-patent reference 7) *Immunol. Today*, 21, 403 (2000)
(Non-patent reference 8) *Ann. Allergy Asthma Immunol.*, 81, 105 (1998)
(Non-patent reference 9) *Nature Biotechnol.*, 16, 1015 (1998)
(Non-patent reference 10) *Nature Reviews Cancer*, 1, 119 (2001)
(Non-patent reference 11) *Curr. Opin. Oncol.*, 10, 548 (1998)
(Non-patent reference 12) *J. Clin. Oncol.*, 16, 2825 (1998)
(Non-patent reference 13) *J. Clin. Oncol.*, 17, 268 (1999)
(Non-patent reference 14) *J. Clin. Oncol.*, 17, 2639 (1999)
(Non-patent reference 15) *Monoclonal Antibodies: Principles and Applications*, Wiley-Liss, Inc. (1995)
(Non-patent reference 16) *Chemical Immunology*, 65, 88 (1997)
(Non-patent reference 17) *Immunol. Today*, 20, 576 (1999)
(Non-patent reference 18) *Nature*, 332, 323 (1988)
(Non-patent reference 19) *Journal of Experimental Medicine*, 166, 1351 (1987)
(Non-patent reference 20) *Biochemistry*, 15, 5175 (1976)
(Non-patent reference 21) *Oncogene*, 22, 7359 (2003)
(Non-patent reference 22) *Blood*, 99, 754 (2002)
(Non-patent reference 23) *J. Immunol.*, 172, 3280 (2004)
(Non-patent reference 24) *J. Clin. Oncol.*, 21, 1466 (2003)
(Non-patent reference 25) *Cancer Immunol. Immunother.*, 37, 255 (1993)
(Non-patent reference 26) *Journal of Experimental Medicine*, 173, 1025 (1991)
(Non-patent reference 27) *Journal of Experimental Medicine*, 173, 1483 (1991)
(Non-patent reference 28) *Sequence of Proteins of Immunological Interest*, 5th Edition (1991)
(Non-patent reference 29) *Immunology*, 86, 319 (1995)
(Non-patent reference 30) *J. Immunol.*, 164, 4178 (2000)
(Non-patent reference 31) *Mol. Immunol.*, 34, 1019 (1997)
(Non-patent reference 32) *Mol. Immunol.*, 37, 995 (2000)
(Non-patent reference 33) *Scand. J. Immunol.*, 32, 517 (1990)
(Non-patent reference 34) *Eur. J. Immunol.*, 21, 2379 (1991)
(Non-patent reference 35) *Mol. Immunol.*, 30, 1419 (1993)
(Non-patent reference 36) *J. Immunol.*, 166, 2571 (2001)
(Non-patent reference 37) *Human Antib Hybrid*, 5, 143 (1994)
(Non-patent reference 38) *Hum Antib Hybrid*, 6, 82 (1995)
(Non-patent reference 39) *Nat. Biotechnol.*, 17, 176 (1999)
(Non-patent reference 40) *Biotechnol. Bioeng.*, 74, 288 (2001)
(Non-patent reference 41) *J. Biol. Chem.*, 277, 26733 (2002)
(Non-patent reference 42) *J. Biol. Chem.*, 278, 3466 (2003)
(Non-patent reference 43) *Biochemistry*, 20, 2361 (1981)
(Non-patent reference 44) *FEBS Lett.*, 328, 49 (1993)
(Non-patent reference 45) Eur. J. Immunol., 29, 2819 (1999)
(Patent reference 1) EP0327378A1
(Patent reference 2) US2003/0158389A1
(Patent reference 3) WO00/42072
(Patent reference 4) US2004/0132101 A1
(Patent reference 5) US2005/0054832 A1
(Patent reference 6) WO00/61739
(Patent reference 7) WO02/31140
(Patent reference 8) WO03/85107

SUMMARY OF THE INVENTION

An antibody which does not have antigenicity, has enhanced effector functions such as CDC activity and ADCC activity and has improved therapeutic effect is in demand. In addition, an antibody which can be produced as a medicine is in demand.

The present invention provides a recombinant antibody composition having higher complement-dependent cytotoxic activity than a human IgG1 antibody and a human IgG3 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al.; a DNA encoding the antibody molecule or a heavy chain constant region of the antibody molecule contained in the recombinant antibody composition; a transformant obtainable by introducing the recombinant vector into a host cell; a process for producing the recombinant antibody composition using the transformant; and a medicament comprising the recombinant antibody composition as an active ingredient.

BRIEF DESCRIPTION OF THE DRAWINGS

FIG. 1 shows amino acid sequences of heavy chain constant regions of respective IgG subclasses.

FIG. 9 shows CDC activity of anti-CD20 human IgG1 chimeric antibodies, anti-CD20 human IgG3 chimeric antibodies and 1133-type anti-CD20 domain-swapped antibodies to ST 486 cell (A) or Raji cell (B). The abscissa shows sample concentration, and the ordinate shows CDC activity in each sample concentration. In the graph, □ shows CD20-IgG1(+F), ■ shows CD20-IgG1(−F), Δ shows CD20-IgG3(+F), ▲ shows CD20-IgG3(−F), ○ shows 1133(+F) and ● shows 1133(−F).

FIG. 12 is a schematic illustration showing an anti-CD20 domain-swapped antibody.

FIG. 18 shows CDC activity of 1133-type anti-CD20 domain-swapped antibody, 1113-type anti-CD20 domain-swapped antibody, 1131-type anti-CD20 domain-swapped antibody, human IgG1 anti-CD20 antibody CD20-IgG1 and human IgG3 anti-CD20 antibody CD20-IgG3 to ST 486 cell (A) or Raji cell (B). The abscissa shows sample concentration, and the ordinate shows cytotoxicity ratio at each sample concentration. In the graph, ■ shows CD20-IgG1, ▲ shows CD20-IgG3, ● shows 1133, × shows 1113 and ♦ shows 1131.

FIG. 25A shows binding activity of CD20-IgG1(–F) (●), CD20-IgG3(–F) (○), 1133(–F) (■), 1131(–F) (☐) and 1113(–F) (∆) to protein A. FIG. 25B shows binding activity of CD20-IgG1(–F) (●), 1133(–F) (■), 113A (–F) (○), 113B(–F) (☐), 113C(–F) (+), 113D(–F) (*), 113E (–F) (◇), 113F(–F) (◆), 113G(–F) (▲) and 113H(–F) (∆) to protein A.

DETAILED DESCRIPTION OF THE INVENTION

Figure 2:
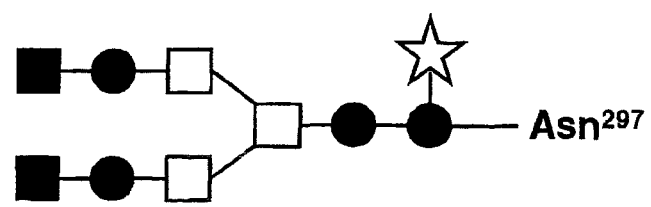
FIG. 2 is a schematic illustration showing structure of a complex type N-linked sugar chain bound to asparagine at position 297 in the H chain of IgG antibody.

Specifically, the present invention relates to the following (1) to (25):
(1) A recombinant antibody composition having higher complement-dependent cytotoxic activity than a human IgG1 antibody and a human IgG3 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al. (hereinafter referred to as EU index).
(2) The recombinant antibody composition according to (1), further having binding activity to protein A, which is substantially equal to that of a human IgG1 antibody.
(3) The recombinant antibody composition according to (1), wherein the polypeptide comprising a CH2 domain in the Fc region of a human IgG1 antibody to be replaced is a polypeptide selected from the following 1 to 10:
1. a polypeptide comprising the amino acid sequence at positions 231 to 340 of an IgG1 antibody indicated by the EU index (SEQ ID NO: 80);
2. a polypeptide comprising the amino acid sequence at positions 231 to 356 of an IgG1 antibody indicated by the EU index (SEQ ID NO: 81);
3. a polypeptide comprising the amino acid sequence at positions 231 to 358 of an IgG1 antibody indicated by the EU index (SEQ ID NO: 82);
4. a polypeptide comprising the amino acid sequence at positions 231 to 384 of an IgG1 antibody indicated by the EU index (SEQ ID NO: 83);
5. a polypeptide comprising the amino acid sequence at positions 231 to 392 of an IgG1 antibody indicated by the EU index (SEQ ID NO: 84);
6. a polypeptide comprising the amino acid sequence at positions 231 to 397 of an IgG1 antibody indicated by the EU index (SEQ ID NO: 85);
7. a polypeptide comprising the amino acid sequence at positions 231 to 422 of an IgG1 antibody indicated by the EU index (SEQ ID NO: 86);
8. a polypeptide comprising the amino acid sequences at positions 231 to 434 (SEQ ID NO: 87)) and at positions 436 to 447 (SEQ ID NO: 88) of an IgG1 antibody indicated by the EU index;
9. a polypeptide comprising the amino acid sequence at positions 231 to 435 of an IgG1 antibody indicated by the EU index (SEQ ID NO: 89); and
10. a polypeptide comprising the amino acid sequence at positions 231 to 447 of an IgG1 antibody indicated by the EU index (SEQ ID NO: 90).
(4) The recombinant antibody composition according to (2), wherein the polypeptide comprising a CH2 domain in the Fc region of a human IgG1 antibody to be replaced is a polypeptide selected from the following 1 to 8:
1. a polypeptide comprising the amino acid sequence at positions 231 to 340 of an IgG1 antibody indicated by the EU index (SEQ ID NO: 80);
2. a polypeptide comprising the amino acid sequence at positions 231 to 356 of an IgG1 antibody indicated by the EU index (SEQ ID NO: 81);
3. a polypeptide comprising the amino acid sequence at positions 231 to 358 of an IgG1 antibody indicated by the EU index (SEQ ID NO: 82);
4. a polypeptide comprising the amino acid sequence at positions 231 to 384 of an IgG1 antibody indicated by the EU index (SEQ ID NO: 83);
5. a polypeptide comprising the amino acid sequence at positions 231 to 392 of an IgG1 antibody indicated by the EU index (SEQ ID NO: 84);
6. a polypeptide comprising the amino acid sequence at positions 231 to 397 of an IgG1 antibody indicated by the EU index (SEQ ID NO: 85);
7. a polypeptide comprising the amino acid sequence at positions 231 to 422 of an IgG1 antibody indicated by the EU index (SEQ ID NO: 86); and
8. a polypeptide comprising the amino acid sequences at positions 231 to 434 (SEQ ID NO: 87) and at positions 436 to 447 (SEQ ID NO: 88) of an IgG1 antibody indicated by the EU index.
(5) The recombinant antibody composition according to any one of (1) to (4), comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more.
(6) The recombinant antibody composition according to any one of (1) to (4), comprising an antibody molecule having complex type N-glycoside-linked sugar chains in the Fc region, wherein the complex type N-glycoside-linked sugar chains bound to the Fc region of the antibody are sugar chains in which fucose is not bound to N-acetylglucosamine in the reducing terminal in the sugar chains.

(7) A DNA encoding the antibody molecule contained in the recombinant antibody composition described in any one of (1) to (4).
(8) A DNA encoding a heavy chain constant region of the antibody molecule contained in the recombinant antibody composition described in any one of (1) to (4).
(9) A transformant obtainable by introducing the DNA described in (8) into a host cell.
(10) The transformant according to (9), wherein the host cell is a cell resistant to a lectin which recognizes a sugar chain structure in which 1-position of fucose is bound to 6-position of N-acetylglucosamine in the reducing terminal through α-bond in the N-glycoside-linked sugar chain.
(11) The transformant according to (9), wherein when a gene encoding an antibody molecule is introduced into the host cell, the host cell is capable of producing an antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more.
(12) The transformant according to (11), wherein the sugar chains in which fucose is not bound are sugar chains in which 1-position of fucose is bound to 6-position of N-acetylglucosamine in the reducing terminal through α-bond in the complex type N-glycoside-linked sugar chain.
(13) The transformant according to (9), wherein the host cell is a cell in which a genome is modified so as to have decreased or deleted activity of an enzyme relating to the synthesis of an intracellular sugar nucleotide, GDP-fucose and/or an enzyme relating to the modification of a sugar chain in which 1-position of fucose is bound to 6-position of N-acetylglucosamine in the reducing terminal through α-bond in the complex type N-glycoside-linked sugar chain.
(14) The transformant according to (9), wherein the host cell is a cell in which all of alleles on a genome encoding an enzyme relating to the synthesis of an intracellular sugar nucleotide, GDP-fucose and/or an enzyme relating to the modification of a sugar chain in which 1-position of fucose is bound to 6-position of N-acetylglucosamine in the reducing terminal through α-bond in the complex type N-glycoside-linked sugar chain are knocked out.
(15) The transformant according to (13) or (14), wherein the enzyme relating to the synthesis of an intracellular sugar nucleotide, GDP-fucose is an enzyme selected from GDP-mannose 4,6-dehydratase (GMD) and GDP-4-keto-6-deoxy-D-mannose-3,5-epimerase (Fx).
(16) The transformant according to (15), wherein the GDP-mannose 4,6-dehydratase is a protein encoded by a DNA selected from the group consisting of the following (a) and (b):
(a) a DNA comprising the nucleotide sequence represented by SEQ ID NO:18;
(b) a DNA which hybridizes with the DNA consisting of the nucleotide sequence represented by SEQ ID NO:18 under stringent conditions and encodes a protein having GDP-mannose 4,6-dehydratase activity.
(17) The transformant according to (15), wherein the GDP-mannose 4,6-dehydratase is a protein selected from the group consisting of the following (a) to (c):
(a) a protein comprising the amino acid sequence represented by SEQ ID NO:19;
(b) a protein consisting of an amino acid sequence in which one or more amino acid(s) is/are deleted, substituted, inserted and/or added in the amino acid sequence represented by SEQ ID NO:19 and having GDP-mannose 4,6-dehydratase activity;
(c) a protein consisting of an amino acid sequence which has 80% or more homology with the amino acid sequence represented by SEQ ID NO:19 and having GDP-mannose 4,6-dehydratase activity.
(18) The transformant according to (15), wherein the GDP-4-keto-6-deoxy-D-mannose-3,5-epimerase is a protein encoded by a DNA selected from the group consisting of the following (a) and (b):
(a) a DNA comprising the nucleotide sequence represented by SEQ ID NO:20;
(b) a DNA which hybridizes with the DNA consisting of the nucleotide sequence represented by SEQ ID NO:20 under stringent conditions and encodes a protein having GDP-4-keto-6-deoxy-D-mannose-3,5-epimerase activity.
(19) The transformant according to (16), wherein the GDP-4-keto-6-deoxy-D-mannose-3,5-epimerase is a protein selected from the group consisting of the following (a) to (c):
(a) a protein comprising the amino acid sequence represented by SEQ ID NO:21;
(b) a protein consisting of an amino acid sequence in which one or more amino acid(s) is/are deleted, substituted, inserted and/or added in the amino acid sequence represented by SEQ ID NO:21 and having GDP-4-keto-6-deoxy-D-mannose-3,5-epimerase activity;
(c) a protein consisting of an amino acid sequence which has 80% or more homology with the amino acid sequence represented by SEQ ID NO:21 and has GDP-4-keto-6-deoxy-D-mannose-3,5-epimerase activity.
(20) The transformant according to (13) or (14), wherein the enzyme relating to the modification of a sugar chain in which 1-position of fucose is bound to 6-position of N-acetylglucosamine in the reducing terminal through α-bond in the complex type N-glycoside-linked sugar chain is α1,6-fucosyltransferase.
(21) The transformant according to (20), wherein the α1,6-fucosyltransferase is a protein encoded by a DNA selected from the group consisting of the following (a) to (d):
(a) a DNA comprising the nucleotide sequence represented by SEQ ID NO:22;
(b) a DNA comprising the nucleotide sequence represented by SEQ ID NO:23;
(c) a DNA which hybridizes with the DNA consisting of the nucleotide sequence represented by SEQ ID NO:22 under stringent conditions and encodes a protein having α1,6-fucosyltransferase activity;
(d) a DNA which hybridizes with the DNA consisting of the nucleotide sequence represented by SEQ ID NO:23 under stringent conditions and encodes a protein having α-1,6-fucosyltransferase activity.
(22) The transformant according to (20), wherein the α1,6-fucosyltransferase is a protein selected from the group consisting of the following (a) to (f):
(a) a protein comprising the amino acid sequence represented by SEQ ID NO:24;
(b) a protein comprising the amino acid sequence represented by SEQ ID NO:25;
(c) a protein consisting of an amino acid sequence in which one or more amino acid(s) is/are deleted, substituted, inserted and/or added in the amino acid sequence represented by SEQ ID NO:24 and having α1,6-fucosyltransferase activity;

(d) a protein consisting of an amino acid sequence in which one or more amino acid(s) is/are deleted, substituted, inserted and/or added in the amino acid sequence represented by SEQ ID NO:25 and having α1,6-fucosyltransferase activity;

(e) a protein consisting of an amino acid sequence which has 80% or more homology with the amino acid sequence represented by SEQ ID NO:24 and having α1,6-fucosyltransferase activity;

(f) a protein consisting of an amino acid sequence which has 80% or more homology with the amino acid sequence represented by SEQ ID NO:25 and having α1,6-fucosyltransferase activity.

(23) The transformant according to any one of (9) to (22), wherein the host cell is a cell selected from the group consisting of the following (a) to (i):

(a) a CHO cell derived from a Chinese hamster ovary tissue;
(b) a rat myeloma cell line, YB2/3HL.P2.G11.16Ag.20 cell;
(c) a mouse myeloma cell line, NS0 cell;
(d) a mouse myeloma cell line, 5P2/0-Ag14 cell;
(e) a BHK cell derived from a syrian hamster kidney tissue;
(f) an antibody-producing hybridoma cell;
(g) a human leukemia cell line, Namalwa cell;
(h) an embryonic stem cell;
(i) a fertilized egg cell.

(24) A process for producing a recombinant antibody composition, which comprises culturing the transformant described in any one of (9) to (23) in a medium to form and accumulate the antibody composition in the culture; and recovering and purifying the antibody composition from the culture.

(25) A medicament comprising the recombinant antibody composition described in any one of (1) to (6) as an active ingredient.

An antibody molecule is constituted by polypeptides called H chain and L chain. Also, the H chain is constituted by regions of a variable region (VH) and CH from its N-terminal, and the L chain is constituted by regions of a variable region (VL) and CL from its N-terminal. CH is further constituted by domains of a CH1 domain, a hinge domain, a CH2 domain and a CH3 domain. The domain means a functional constitution unit constituting each polypeptide in the antibody molecule. Also, the CH2 domain and the CH3 domain in combination are called Fc region.

The CH1 domain, the hinge domain, the CH2 domain, the CH3 domain and the Fc region are defined by positions of amino acid residues from the N-terminal indicated by the EU index as in Kabat, et al. [*Sequence of Proteins of Immunological Interest*, 5th Edition (1991)]. Specifically, CH1 is defined as the amino acid sequence of positions 118 to 215 indicated by the EU index, the hinge is defined as the amino acid sequence of positions 216 to 230 indicated by the EU index, CH2 is defined as the amino acid sequence of positions 231 to 340 indicated by the EU index, and CH3 is defined as the amino acid sequence of positions 341 to 447 indicated by the EU index.

The recombinant antibody composition of the present invention may be any antibody composition, so long as it is a recombinant antibody composition having higher complement-dependent cytotoxic activity than a human IgG1 antibody and a human IgG3 antibody, wherein a polypeptide comprising a CH2 domain in the Fg region of a human IgG1 antibody is replaced by a polypeptide comprising an amino acid sequence which corresponds to the same position of a human IgG3 antibody indicated by the EU index as in Kabat et al., among the recombinant antibody compositions in which domains of CH1, the hinge, CH2 and CH3 in the heavy chain constant region of a human IgG1 are swapped into domains corresponding to IgG3 (hereinafter referred to as domain-swapped antibody).

The recombinant antibody composition of the present invention may be any antibody composition, so long as it is a fusion protein having a heavy chain constant region, having an antibody or heavy chain constant region which has binding activity to a target molecule, and having binding activity to a target molecule.

The antibody having binding activity to a target molecule includes a human chimeric antibody, a humanized antibody and a human antibody.

The fusion protein having a heavy chain constant region and binding activity to a target molecule includes, in the case where the target molecule is a ligand, a fusion protein of a receptor for the ligand and a heavy chain constant region; in the case where the target molecule is a receptor, a fusion protein of a ligand for the receptor and a heavy chain constant region; a fusion protein of an antibody or antibody fragment having binding activity to a target molecule and a heavy chain constant region; and the like.

A human chimeric antibody is an antibody which comprises VH and VL of a non-human animal antibody, and CH and CL of human antibody. The non-human animal may be any animal such as a mouse, a rat, a hamster or a rabbit, so long as a hybridoma can be prepared therefrom.

The human chimeric antibody of the present invention can be produced by obtaining cDNAs encoding VH and VL from a monoclonal antibody-producing hybridoma, inserting them into an expression vector for animal cell comprising DNAs encoding CH and CL of human antibody to thereby construct a human chimeric antibody expression vector, and then introducing the vector into an animal cell to express the antibody.

As the CH of human chimeric antibody, any CH can be used, so long as it belongs to human immunoglobulin (hIg), and those belonging to the hIgG class are preferred, and any one of the subclasses belonging to the hIgG class, such as γ1, γ2, γ3 and γ4, can be used. As the CL of human chimeric antibody, any CL can be used, so long as it belongs to the hIg class, and those belonging to the κ class or λ class can be used.

A humanized antibody is an antibody in which amino acid sequences of CDRs of VH and VL of a non-human animal antibody are grafted into appropriate positions of VH and VL of a human antibody.

The humanized antibody of the present invention can be produced by constructing cDNAs encoding V regions in which the amino acid sequences of CDRs of VH and VL of a non-human animal antibody are grafted into the FRs of VH and VL of any human antibody, inserting them into an expression vector for animal cell comprising DNAs encoding CH and CL of a human antibody to thereby construct a humanized antibody expression vector, and then introducing the expression vector into an animal cell to express the humanized antibody.

As the CH of the humanized antibody, any CH can be used, so long as it belongs to the hIg, and those of the hIgG class are preferred and any one of the subclasses belonging to the hIgG class, such as γ1, γ2, γ3 and γ4, can be used. As the CL of the human CDR-grafted antibody, any CL can be used, so long as it belongs to the hIg class, and those belonging to the κ class or λ class can be used.

A human antibody is originally an antibody naturally existing in the human body, but it also includes antibodies obtained from a human antibody phage library or a human antibody-producing transgenic animal, which is prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the culture.

The antibody fragment having binding activity to a target molecule includes Fab, Fab', F(ab')$_2$, scFv, diabody, dsFv, a peptide comprising CDR, and the like.

An Fab is an antibody fragment having a molecular weight of about 50,000 and having antigen binding activity, in which about a half of the N-terminal side of H chain and the entire L chain, among fragments obtained by treating IgG with a protease, papain (cleaving an amino acid residue at the 224th position of the H chain), are bound together through a disulfide bond (S—S bond).

An F(ab')$_2$ is an antibody fragment having antigen binding activity and having a molecular weight of about 100,000 which is somewhat larger than one in which Fab are bound via an S—S bond in the hinge region, among fragments obtained by treating IgG with a protease, pepsin (by cleaving the H chain at the 234th amino acid residue).

An Fab' is an antibody fragment having a molecular weight of about 50,000 and having antigen binding activity, which is obtained by cleaving an S—S bond in the hinge region of the F(ab')$_2$.

An scFv is a VH-P-VL or VL-P-VH polypeptide in which one chain VH and one chain VL are linked using an appropriate peptide linker (P) having 12 or more residues and is an antibody fragment having antigen binding activity.

A diabody is an antibody fragment in which scFv's having the same or different antigen binding specificity forms a dimer, and has divalent antigen binding activity to the same antigen or two specific antigen binding activities to different antigens.

A dsFv is obtained by binding polypeptides in which one amino acid residue of each of VH and VL is substituted with a cysteine residue via an S—S bond between the cysteine residues.

A peptide comprising CDR is constituted by including at least one region or more of CDRs of VH or VL. Plural peptide comprising CDRs can be produced by binding directly or via an appropriate peptide linker.

Specifically, the recombinant antibody composition of the present invention include a recombinant composition in which the polypeptide comprising a CH2 domain in the Fc region of a human IgG1 antibody to be replaced is a polypeptide selected from the following 1 to 10:

1. a polypeptide comprising the amino acid sequence at positions 231 to 340 of an IgG1 antibody indicated by the EU index (SEQ ID NO: 80);
2. a polypeptide comprising the amino acid sequence at positions 231 to 356 of an IgG1 antibody indicated by the EU index (SEQ ID NO: 81);
3. a polypeptide comprising the amino acid sequence at positions 231 to 358 of an IgG1 antibody indicated by the EU index (SEQ ID NO: 82);
4. a polypeptide comprising the amino acid sequence at positions 231 to 384 of an IgG1 antibody indicated by the EU index (SEQ ID NO: 83);
5. a polypeptide comprising the amino acid sequence at positions 231 to 392 of an IgG1 antibody indicated by the EU index (SEQ ID NO: 84);
6. a polypeptide comprising the amino acid sequence at positions 231 to 397 of an IgG1 antibody indicated by the EU index (SEQ ID NO: 85);
7. a polypeptide comprising the amino acid sequence at positions 231 to 422 of an IgG1 antibody indicated by the EU index (SEQ ID NO: 86);
8. a polypeptide comprising the amino acid sequences at positions 231 to 434 (SEQ ID NO: 87) and at positions 436 to 447 (SEQ ID NO: 88) of an IgG1 antibody indicated by the EU index;
9. a polypeptide comprising the amino acid sequence at positions 231 to 435 of an IgG1 antibody indicated by the EU index (SEQ ID NO: 89); and
10. a polypeptide comprising the amino acid sequence at positions 231 to 447 of an IgG1 antibody indicated by the EU index (SEQ ID NO: 90).

The amino acid sequence of the CL region in the recombinant antibody composition of the present invention may be either an amino acid sequence of a human antibody or an amino acid sequence from a non-human animal, but it is preferably Cκ or Cλ of an amino acid sequence of a human antibody.

In the variable region of the recombinant antibody composition of the present invention, VH and VL may be any of an amino acid sequence of a human antibody, an amino acid sequence of a non-human animal antibody or a mixed amino acid sequence of these amino acid sequences. Specifically, they include a variable region constituting an antibody produced by a hybridoma, a variable region constituting a humanized antibody, a variable region constituting a human antibody, and the like.

A hybridoma is a cell which is obtained by cell fusion between a B cell obtained by immunizing a non-human mammal with an antigen and a myeloma cell derived from mouse or the like and can produce a monoclonal antibody having the desired antigen specificity. Accordingly, the variable region constituting the antibody produced by the hybridoma consists of amino acid sequences of non-human animal antibody.

The recombinant antibody composition of the present invention includes antibodies having any specificity, and is preferably an antibody which recognizes a tumor-related antigen, an antibody which recognizes an allergy- or inflammation-related antigen, an antibody which recognizes cardiovascular disease-related antigen, an antibody which recognizes an autoimmune disease-related antigen or an antibody which recognizes a viral or bacterial infection-related antigen.

The antibody which recognizes a tumor-related antigen includes anti-GD2 antibody [*Anticancer Res.*, 13, 331 (1993)], anti-GD3 antibody [*Cancer Immunol. Immunother.*, 36, 260 (1993)], anti-GM2 antibody [*Cancer Res.*, 54, 1511 (1994)], anti-HER2 antibody [*Proc. Natl. Acad. Sci. USA*, 89, 4285 (1992)], anti-CD52 antibody [*Proc. Natl. Acad. Sci. USA*, 89, 4285 (1992)], anti-MAGE antibody [*British J. Cancer*, 83, 493 (2000)], anti-HM1.24 antibody [*Molecular*

Immunol., 36, 387 (1999)], anti-parathyroid hormone-related protein (PTHrP) antibody [Cancer, 88, 2909 (2000)], anti-basic fibroblast growth factor antibody, anti-fibroblast growth factor 8 antibody [Proc. Natl. Acad. Sci. USA, 86, 9911 (1989)], anti-basic fibroblast growth factor receptor antibody, anti-fibroblast growth factor 8 receptor antibody [J. Biol. Chem., 265, 16455 (1990)], anti-insulin-like growth factor antibody [J. Neurosci. Res., 40, 647 (1995)], anti-insulin-like growth factor receptor antibody [J. Neurosci. Res., 40, 647 (1995)], anti-PSMA antibody [J. Urology, 160, 2396 (1998)], anti-vascular endothelial cell growth factor antibody [Cancer Res., 57, 4593 (1997)], anti-vascular endothelial cell growth factor receptor antibody [Oncogene, 19, 2138 (2000)], anti-CD20 antibody [Curr. Opin. Oncol., 10, 548 (1998)], anti-Her2 antibody, anti-CD10 antibody, and the like.

The antibody which recognizes an allergy- or inflammation-related antigen includes anti-interleukin 6 antibody [Immunol. Rev., 127, 5 (1992)], anti-interleukin 6 receptor antibody [Molecular Immunol., 31, 371 (1994)], anti-interleukin 5 antibody [Immunol. Rev., 127, 5 (1992)], anti-interleukin 5 receptor antibody, anti-interleukin 4 antibody [Cytokine, 3, 562 (1991)], anti-interleukin 4 receptor antibody [J. Immunol. Meth., 217, 41 (1998)], anti-tumor necrosis factor antibody [Hybridoma, 13, 183 (1994)], anti-tumor necrosis factor receptor antibody [Molecular Pharmacol., 58, 237 (2000)], anti-CCR4 antibody [Nature, 400, 776 (1999)], anti-chemokine antibody [Peri et al., J. Immuno. Meth., 174, 249-257 (1994)], anti-chemokine receptor antibody [J. Exp. Med., 186, 1373 (1997)] or the like. The antibody which recognizes a cardiovascular disease-related antigen includes anti-GpIIb/IIIa antibody [J. Immunol., 152, 2968 (1994)], anti-platelet-derived growth factor antibody [Science, 253, 1129 (1991)], anti-platelet-derived growth factor receptor antibody [J. Biol. Chem., 272, 17400 (1997)], anti-blood coagulation factor antibody [Circulation, 101, 1158 (2000)] and the like.

The antibody which recognizes a viral or bacterial infection-related antigen includes anti-gp120 antibody [Structure, 8, 385 (2000)], anti-CD4 antibody [J. Rheumatology, 25, 2065 (1998)], anti-CCR5 antibody and anti-Vero toxin antibody [J. Clin. Microbiol., 37, 396 (1999)] and the like.

The recombinant antibody composition of the present invention has higher CDC activity than a human IgG1 antibody and a human IgG3 antibody by replacing polypeptide comprising a CH2 domain in the Fc region of a human IgG1 antibody with a polypeptide comprising an amino acid sequence which corresponds to the same position of a human IgG3 antibody indicated by the EU index.

Furthermore, the recombinant antibody composition of the present invention includes recombinant antibody composition having higher complement-dependent cytotoxic activity than a human IgG1 antibody and a human IgG3 antibody and having binding activity to protein A, which is substantially equal to that of a human IgG1 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al.

Specifically, examples include the recombinant antibody composition wherein the polypeptide comprising a CH2 domain in the Fc region of a human IgG1 antibody to be replaced is a polypeptide selected from the following 1 to 8:
1. a polypeptide comprising the amino acid sequence at positions 231 to 340 of an IgG1 antibody indicated by the EU index (SEQ ID NO: 80);
2. a polypeptide comprising the amino acid sequence at positions 231 to 356 of an IgG1 antibody indicated by the EU index (SEQ ID NO: 81);
3. a polypeptide comprising the amino acid sequence at positions 231 to 358 of an IgG1 antibody indicated by the EU index (SEQ ID NO: 82);
4. a polypeptide comprising the amino acid sequence at positions 231 to 384 of an IgG1 antibody indicated by the EU index (SEQ ID NO: 83);
5. a polypeptide comprising the amino acid sequence at positions 231 to 392 of an IgG1 antibody indicated by the EU index (SEQ ID NO: 84);
6. a polypeptide comprising the amino acid sequence at positions 231 to 397 of an IgG1 antibody indicated by the EU index (SEQ ID NO: 85);
7. a polypeptide comprising the amino acid sequence at positions 231 to 422 of an IgG1 antibody indicated by the EU index (SEQ ID NO: 86);
8. a polypeptide comprising the amino acid sequences at positions 231 to 434 (SEQ ID NO: 87) and at positions 436 to 447 (SEQ ID NO: 88) of an IgG1 antibody indicated by the EU index.

The binding activity to protein A can be measured by ELISA, surface plasmon resonance or the like. Specifically, the antibody composition is allowed to react with protein A solid-phased on a plate and then is further allowed to react with an antibody which recognizes the variously labeled antibodies, and the binding activity can be measured by determining the antibody composition bound to protein A.

Also, the antibody composition is allowed to react with protein A bound to a carrier such as sepharose at high pH conditions such as a pH of about 5 to 8, followed by washing, and then the binding activity can be measured by determining the antibody composition eluted at low pH conditions such as a pH of about 2 to 5.

The Fc region in the antibody molecule comprises regions to which N-glycoside-linked sugar chains are bound. Accordingly, two sugar chains are bound per one antibody molecule.

The N-glycoside-linked sugar chain include a complex type sugar chain in which the non-reducing terminal side of the core structure comprises one or plurality of parallel side chains of galactose-N-acetylglucosamine (hereinafter referred to as "Gal-GlcNAc") and the non-reducing terminal side of Gal-GlcNAc further comprises a structure of sialic acid, bisecting N-acetylglucosamine or the like.

In the present invention, the complex type N-glycoside-linked sugar chain is represented by the following formula:

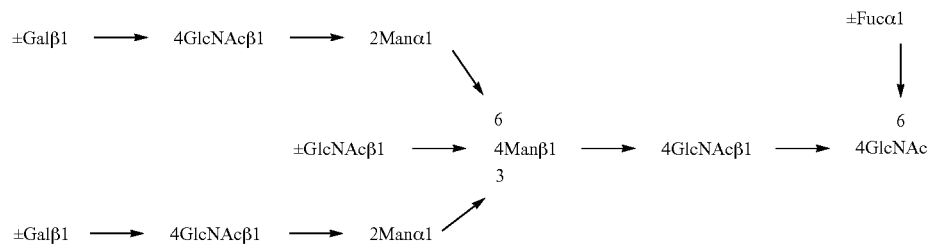

Among the recombinant antibody compositions of the present invention, the recombinant antibody composition comprising an antibody molecule in the Fc region of the N-glycoside-linked sugar chain may comprise an antibody molecule having the same sugar chain structure or an antibody molecule having different sugar chain structures, so long as it has the above sugar chain structure. That is, the recombinant antibody composition of the present invention means a composition comprising a recombinant antibody molecule having the same or different sugar chain structure(s).

Furthermore, among the recombinant antibodies of the present invention, the antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more, has high ADCC activity in addition to CDC activity.

In the present invention, the sugar chain in which fucose is not bound may have any sugar chain structure in the non-reducing terminal, so long as fucose is not bound to N-acetylglucosamine in the reducing terminal in the above formula.

In the present invention, the case where fucose is not bound to N-acetylglucosamine in the reducing terminal in the sugar chain means that fucose is not substantially bound. An antibody composition in which fucose is not substantially bound specifically refers to an antibody composition in which fucose is not substantially detected, i.e., the content of fucose is below the detection limit, when subjected to the sugar chain analysis described in the following item 4. A recombinant antibody composition in which fucose is not bound to N-acetylglucosamine in the reducing terminals of all sugar chains has highest ADCC activity.

The ratio of sugar chains in which fucose is not bound to N-acetylglucosamine in the reducing terminal in the sugar chains contained in the composition which comprises an antibody molecule having complex type N-glycoside-linked sugar chains in the Fc region can be determined by releasing the sugar chains from the antibody molecule using a known method such as hydrazinolysis or enzyme digestion [*Biochemical Experimentation Methods* 23—*Method for Studying Glycoprotein Sugar Chain* (Japan Scientific Societies Press), edited by Reiko Takahashi (1989)], carrying out fluorescence labeling or radioisotope labeling of the released sugar chains and then separating the labeled sugar chains by chromatography. Also, the released sugar chains can also be determined by analyzing it with the HPAED-PAD method [*J. Liq. Chromatogr.*, 6, 1577 (1983)].

The transformant producing the recombinant antibody composition of the present invention can be obtained by introducing, into an animal cell, an animal cell expression vector into which DNAs encoding a variable region and a constant region of an antibody molecule are inserted.

The animal cell expression vector is constructed below.

Each of the above DNAs encoding CH and CL is introduced into an expression vector for animal cell to produce an expression vector for animal cell.

The expression vector for animal cell includes pAGE107 (Japanese Published Unexamined Patent Application No. 22979/91; Miyaji H. et al., *Cytotechnology*, 3, 133-140 (1990)), pAGE103 (Mizukami T. and Itoh S., *J. Biochem.*, 101, 1307-1310 (1987)), pHSG274 (Brady G. et al., Gene, 27, 223-232 (1984)), pKCR (O'Hare K. et al., *Proc. Natl. Acad. Sci. USA.*, 78, 1527-1531 (1981)), pSG1βd2-4 (Miyaji H. et al., *Cytotechnology*, 4, 173-180 (1990)) and the like. The promoter and enhancer used for the expression vector for animal cell include SV40 early promoter and enhancer (Mizukami T. and Itoh S., *J. Biochem.*, 101, 1307-1310 (1987)), LTR promoter and enhancer of Moloney mouse leukemia virus (Kuwana Y. et al., *Biochem. Biophys. Res. Commun.*, 149, 960-968 (1987)), immunoglobulin H chain promoter (Mason J. O. et al., *Cell*, 41, 479-487 (1985)) and ehnancer (Gillies S. D. et al., *Cell*, 33, 717-728 (1983)) and the like.

The vector for expression of recombinant antibody composition may be either of a type in which genes encoding the H chain and L chain exist on separate vectors or of a type in which both genes exist on the same vector (tandem type). In respect of easiness of construction of a recombinant antibody composition expression vector, easiness of introduction into animal cells, and balance between the expression amounts of the H and L chains of an antibody in animal cells, a tandem type of the vector for expression of recombinant antibody composition is more preferred (Shitara K. et al., *J. Immunol. Methods*, 167, 271-278 (1994)). The tandem type vector for expression of recombinant antibody composition includes pKANTEX93 (WO97/10354), pEE18 (Bentley K. J. et al., Hybridoma, 17, 559-567 (1998)) and the like.

cDNAs encoding VH and VL of antibodies for various antigens are cloned into the upstream of DNAs encoding CH and CL of the constructed vector for expression of recombinant antibody composition to thereby construct a recombinant antibody composition expression vector.

A method for introducing the expression vector into a host cell includes electroporation (Japanese Published Unexamined Patent Application No. 257891-90; Miyaji H. et al., *Cytotechnology*, 3, 133-140 (1990)) and the like.

The host cell producing the recombinant antibody composition of the present invention may be any host cell which is generally used in production of a recombinant protein, such as an animal cell, a plant cell or a microorganism.

The host cell producing the recombinant antibody composition of the present invention includes a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag14 cell, a BHK cell derived from a syrian hamster kidney tissue, a human leukemia cell line Namalwa cell, a hybridoma cell produced by using a myeloma cell and any B cell, a hybridoma cell produced by a B cell obtained by immunizing with an antigen a transgenic non-human animal produced by using an embryonic stem cell or a fertilized egg cell and any myeloma cell; a hybridoma cell produced by the above myeloma cell and a B cell obtained by immunizing a transgenic non-human animal produced by using an embryonic stem cell or a fertilized egg cell; and the like, with an antigen.

The host cell capable of expressing a recombinant antibody composition having high ADCC activity as well as CDC activity includes a host cell resistant to a lectin which recognizes a sugar chain structure in which 1-position of fucose is bound to 6-position of N-acetylglucosamine in the reducing terminal through α-bond in the complex type N-glycoside-linked sugar chain, such as a host cell capable of producing an antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more. Examples include cells in which activity of at least one protein described below is decreased or deleted, and the like:
(a) an enzyme protein relating to synthesis of an intracellular sugar nucleotide, GDP-fucose;
(b) an enzyme protein relating to the modification of a sugar chain in which 1-position of fucose is bound to 6-position of N-acetylglucosamine in the reducing terminal through α-bond in a complex type N-glycoside-linked sugar chain;
(c) a protein relating to transport of an intracellular sugar nucleotide, GDP-fucose, to the Golgi body.

The above host cell is preferably a host cell in which a gene encoding α1,6-fucosyltransferase in the host cell is knocked out (WO02/31140, WO03/85107).

The enzyme protein relating to synthesis of an intracellular sugar nucleotide, GDP-fucose may be any enzyme, so long as it is an enzyme relating to the synthesis of the intracellular sugar nucleotide, GDP-fucose, as a supply source of fucose to a sugar chain. The enzyme relating to synthesis of an intracellular sugar nucleotide, GDP-fucose includes an enzyme which has influence on the synthesis of the intracellular sugar nucleotide, GDP-fucose, and the like.

The intracellular sugar nucleotide, GDP-fucose, is supplied by a de novo synthesis pathway or a salvage synthesis pathway. Thus, all enzymes relating to the synthesis pathways are included in the enzyme relating to synthesis of an intracellular sugar nucleotide, GDP-fucose.

The enzyme relating to the de novo synthesis pathway of an intracellular sugar nucleotide, GDP-fucose includes GDP-mannose 4,6-dehydratase (hereinafter referred to as "GMD"), GDP-keto-6-deoxymannose-3,5-epimerase, 4,6-reductase (hereinafter referred to as "Fx") and the like.

The enzyme relating to the salvage synthesis pathway of an intracellular sugar nucleotide, GDP-fucose includes GDP-beta-L-fucose pyrophosphorylase (hereinafter referred to as "GFPP"), fucokinase and the like.

As the enzyme which has influence on the synthesis of an intracellular sugar nucleotide, GDP-fucose, an enzyme which has influence on the activity of the enzyme relating to the synthesis pathway of the intracellular sugar nucleotide, GDP-fucose described above, and an enzyme which has influence on the structure of substances as the substrate of the enzyme are also included.

The GDP-mannose 4,6-dehydratase includes:
(a) a DNA comprising the nucleotide sequence represented by SEQ ID NO:18;
(b) a DNA which hybridizes with the DNA consisting of the nucleotide sequence represented by SEQ ID NO:18 under stringent conditions and encodes a protein having GDP-mannose 4,6-dehydratase activity,
and the like.

The GDP-mannose 4,6-dehydratase includes:
(a) a protein comprising the amino acid sequence represented by SEQ ID NO:19;
(b) a protein consisting of an amino acid sequence in which one or more amino acid(s) is/are deleted, substituted, inserted and/or added in the amino acid sequence represented by SEQ ID NO:19 and having GDP-mannose 4,6-dehydratase activity;
(c) a protein consisting of an amino acid sequence which has 80% or more homology with the amino acid sequence represented by SEQ ID NO:19 and having GDP-mannose 4,6-dehydratase activity;
and the like.

The GDP-4-keto-6-deoxy-D-mannose-3,5-epimerase includes:
(a) a DNA comprising the nucleotide sequence represented by SEQ ID NO:20;
(b) a DNA which hybridizes with the DNA consisting of the nucleotide sequence represented by SEQ ID NO:20 under stringent conditions and encodes a protein having GDP-4-keto-6-deoxy-D-mannose-3,5-epimerase activity;
and the like.

The GDP-4-keto-6-deoxy-D-mannose-3,5-epimerase includes:
(a) a protein comprising the amino acid sequence represented by SEQ ID NO:21;
(b) a protein consisting of an amino acid sequence in which one or more amino acid(s) is/are deleted, substituted, inserted and/or added in the amino acid sequence represented by SEQ ID NO:21 and having GDP-4-keto-6-deoxy-D-mannose-3,5-epimerase activity;
(c) a protein consisting of an amino acid sequence which has 80% or more homology with the amino acid sequence represented by SEQ ID NO:21 and has GDP-4-keto-6-deoxy-D-mannose-3,5-epimerase activity;
and the like.

The enzyme protein relating to the modification of a sugar chain in which 1-position of fucose is bound to 6-position of N-acetylglucosamine in the reducing terminal through α-bond in a complex type N-glycoside-linked sugar chain includes any enzyme, so long as it is an enzyme relating to the reaction of binding of 1-position of fucose to 6-position of N-acetylglucosamine in the reducing terminal through α-bond in the complex type N-glycoside-linked sugar chain. The enzyme relating to the reaction of binding of 1-position of fucose to 6-position of N-acetylglucosamine in the reducing terminal through α-bond in the complex type N-glycoside-linked sugar chain includes an enzyme which has influence on the reaction of binding of 1-position of fucose to 6-position of N-acetylglucosamine in the reducing terminal through α-bond in the complex type N-glycoside-linked sugar chain. Examples include α1,6-fucosyltransferase, α-L-fucosidase and the like.

Also, the enzyme relating to the reaction of binding of 1-position of fucose to 6-position of N-acetylglucosamine in the reducing terminal through α-bond in the complex type N-glycoside-linked sugar chain includes an enzyme which has influence on the activity of the enzyme relating to the reaction of binding of 1-position of fucose to 6-position of N-acetylglucosamine in the reducing terminal through α-bond in the complex type N-glycoside-linked sugar chain and an enzyme which has influence on the structure of substances as the substrate of the enzyme.

In the present invention, the α1,6-fucosyltransferase is a protein encoded by a DNA of the following (a), (b), (c) or (d):
(a) a DNA comprising the nucleotide sequence represented by SEQ ID NO:22;
(b) a DNA comprising the nucleotide sequence represented by SEQ ID NO:23;
(c) a DNA which hybridizes with the DNA consisting of the nucleotide sequence represented by SEQ ID NO:22 under stringent conditions and encodes a protein having α1,6-fucosyltransferase activity;
(d) a DNA which hybridizes with the DNA consisting of the nucleotide sequence represented by SEQ ID NO:23 under stringent conditions and encodes a protein having α-1,6-fucosyltransferase activity, or
(e) a protein comprising the amino acid sequence represented by SEQ ID NO:24;
(f) a protein comprising the amino acid sequence represented by SEQ ID NO:25;
(g) a protein consisting of an amino acid sequence in which one or more amino acid(s) is/are deleted, substituted, inserted and/or added in the amino acid sequence represented by SEQ ID NO:24 and having α1,6-fucosyltransferase activity;
(h) a protein consisting of an amino acid sequence in which one or more amino acid(s) is/are deleted, substituted, inserted and/or added in the amino acid sequence represented by SEQ ID NO:25 and having α1,6-fucosyltransferase activity;
(i) a protein consisting of an amino acid sequence which has 80% or more homology with the amino acid sequence represented by SEQ ID NO:24 and having α1,6-fucosyltransferase activity;
(j) a protein consisting of an amino acid sequence which has 80% or more homology with the amino acid sequence represented by SEQ ID NO:25 and having α1,6-fucosyltransferase activity;
and the like.

The protein relating to transport of an intracellular sugar nucleotide, GDP-fucose, to the Golgi body may be any protein, so long as it is a protein relating to the transport of the intracellular sugar nucleotide, GDP-fucose, to the Golgi body, or a protein which has an influence on the reaction for the transport of the intracellular sugar nucleotide, GDP-fucose, to the Golgi body.

The protein relating to the transport of the intracellular sugar nucleotide, GDP-fucose, to the Golgi body includes a GDP-fucose transporter and the like.

Also, the protein which has an influence on the reaction for the transport of the intracellular sugar nucleotide, GDP-fucose, to the Golgi body include a protein which has an influence on the activity of the above protein relating to the transport of the intracellular sugar nucleotide, GDP-fucose, to the Golgi body or has influence on the expression thereof.

The DNA encoding the amino acid sequence of the enzyme relating to synthesis of an intracellular sugar nucleotide, GDP-fucose includes a DNA comprising the nucleotide sequence represented by SEQ ID NO:18 or 20; a DNA which hybridizes with the DNA consisting of the nucleotide sequence represented by SEQ ID NO:18 or 20 under stringent conditions and encodes a protein having activity of the enzyme relating to synthesis of an intracellular sugar nucleotide, GDP-fucose; and the like.

The DNA encoding the amino acid sequence of the α1,6-fucosyltransferase includes a DNA comprising the nucleotide sequence represented by SEQ ID NO:22 or 23; a DNA which hybridizes with the DNA consisting of the nucleotide sequence represented by SEQ ID NO:22 or 23 under stringent conditions and encodes a protein having α1,6-fucosyltransferase activity; and the like.

The method for obtaining a cell in which the above enzyme activity is decreased or deleted may by any method, so long as it is a method for decreasing or deleting the objective enzyme activity. Examples include:
(a) gene disruption targeting at a gene encoding the enzyme;
(b) introduction of a dominant-negative mutant of a gene encoding the enzyme;
(c) introduction of a mutation into the enzyme;
(d) suppression of transcription or translation of a gene encoding the enzyme;
(e) selection of a cell line resistant to a lectin which recognizes a sugar chain structure in which 1-position of fucose is bound to 6-position of N-acetylglucosamine in the reducing terminal through α-bond in a N-glycoside-linked sugar chain;
and the like.

As the lectin which recognizes a sugar chain structure in which 1-position of fucose is bound to 6-position of N-acetylglucosamine in the reducing terminal through α-bond in a N-glycoside-linked sugar chain, any lectin capable of recognizing the sugar chain structure can be used. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*), *Aleuria aurantia* lectin AAL (lectin derived from *Aleuria aurantia*) and the like.

The "cell resistant to a lectin" refers to a cell in which growth is not inhibited by the presence of a lectin at an effective concentration. The "effective concentration" is a concentration higher than the concentration that does not allow the normal growth of a cell prior to the genome modification (hereinafter referred to also as parent cell line), preferably equal to the concentration that does not allow the normal growth of a cell prior to the genome modification, more preferably 2 to 5 times, further preferably 10 times, most preferably 20 or more times the concentration that does not allow the normal growth of a cell prior to the modification of the genomic gene.

The effective concentration of lectin that does not inhibit growth may be appropriately determined according to each cell line. It is usually 10 μg/ml to 10 mg/ml, preferably 0.5 mg/ml to 2.0 mg/ml.

Processes for producing the recombinant antibody composition of the present invention are explained below in detail.

1. Process for Producing Recombinant Antibody Composition

The recombinant antibody composition of the present invention can be obtained, for example, by expressing it in a host cell using the methods described in *Molecular Cloning*, Second Edition; *Current Protocols in Molecular Biology*; *Antibodies, A Laboratory manual*, Cold Spring Harbor Laboratory (1988) (hereinafter referred to as *Antibodies*); *Monoclonal Antibodies: principles and practice*, Third Edition, Acad. Press (1993) (hereinafter referred to as *Monoclonal Antibodies*); *Antibody Engineering, A Practical Approach*, IRL Press at Oxford University Press, 1996 (hereinafter referred to as *Antibody Engineering*); and the like, for example, in the following manner.

(1) Construction of a Vector for Expression of the Recombinant Antibody Composition of the Present Invention A vector for expression of the recombinant antibody composition of the present invention is an expression vector for animal cell into which genes encoding H chain and L chain constant regions of an antibody molecule contained in the recombinant antibody composition of the present invention are introduced. The vector for expression of the recombinant antibody composition can be constructed by cloning each of the genes encoding H chain and L chain constant regions of an antibody molecule contained in the recombinant antibody composition into a vector for expression of animal cell.

The gene encoding the CH region of an antibody molecule contained in the recombinant antibody composition of the present invention can be produced by cloning genes encoding constant regions of IgG1 and IgG3 antibodies and then ligating gene fragments encoding respective domains. Also, the total DNA can be synthesized by using synthetic DNAs and synthesis using PCR can also be carried out (*Molecular Cloning*, Second Edition). Furthermore, it can be produced by combining these techniques.

The expression vector for animal cell may by any vector, so long as the above gene encoding the constant region of an antibody molecule can be introduced and expressed. Examples include pKANTEX93 [*Mol. Immunol.*, 37, 1035 (2000)], pAGE107 [*Cytotechnology*, 3, 133 (1990), pAGE103 [*J. Biochem.*, 101, 1307 (1987)], pHSG274 [*Gene*, 27, 223 (1984)], pKCR [*Proc. Natl. Acad. Sci. U.S.A.*, 78, 1527 (1981)], pSG1βd2-4 [*Cytotechnology*, 4, 173 (1990)] and the like. The promoter and enhancer used for the expression vector for animal cell include SV40 early promoter and enhancer [*J. Biochem.*, 101, 1307 (1987)], LTR of Moloney mouse leukemia virus [*Biochem. Biophys. Res. Commun.*, 149, 960 (1987)], immunoglobulin H chain promoter [*Cell*, 41, 479 (1985)] and ehnancer [*Cell*, 33, 717 (1983)] and the like.

The vector for expression of the recombinant antibody composition of the present invention may be either of a type in which genes encoding the H chain and L chain of antibody exist on separate vectors or of a type in which both genes exist on the same vector (tandem type). In respect of easiness of construction of a vector for expression of the recombinant antibody composition of the present invention, easiness of introduction into animal cells, and balance between the expression amounts of the H and L chains of antibody in animal cells, a tandem type of the vector for expression of humanized antibody is more preferred (*J. Immunol. Methods*, 167, 271 (1994)).

The constructed vector for expression of the recombinant antibody composition of the present invention can be used for expression of a human chimeric antibody and a humanized antibody in animal cells.

(2) Obtaining of cDNA Encoding V Region of Non-Human Animal Antibody cDNAs encoding VH and VL of a non-human animal antibody such as a mouse antibody can be obtained in the following manner.

A cDNA is synthesized by using as a probe mRNA extracted from a hybridoma cell which produces any antibody. The synthesized cDNA is cloned into a vector such as a phage or a plasmid to obtain a cDNA library. Each of a recombinant phage or recombinant plasmid comprising a cDNA encoding the H chain V region and a recombinant phage or recombinant plasmid comprising a cDNA encoding the L chain V region is isolated from the library by using cDNA encoding C region or V region of a known mouse antibody as the probe. Full length nucleotide sequences of VH and VL of the mouse antibody of interest on the recombinant phage or recombinant plasmid are determined, and full length amino acid sequences of VH and VL are deduced from the nucleotide sequences.

Hybridoma cells producing any non-human animal-derived antibody can be obtained by immunizing a non-human animal with an antigen bound to the antibody, preparing hybridomas from antibody-producing cells of the immunized animal and myeloma cells according to a known method [*Molecular Cloning*, Second Edition; *Current Protocols in Molecular Biology*; *Antibodies, A Laboratory manual*, Cold Spring Harbor Laboratory (1988) (hereinafter referred to as *Antibodies*); *Monoclonal Antibodies: principles and practice*, Third Edition, Acad. Press (1993) (hereinafter referred to as *Monoclonal Antibodies*), *Antibody Engineering, A Practical Approach*, IRL Press at Oxford University Press (1996) (hereinafter referred to as *Antibody Engineering*)], selecting cloned hybridomas, culturing the selected hybridomas and purifying cells from the culture supernatant.

As the non-human animal, any animal can be used so long as hybridoma cells can be prepared from the animal. Suitable animals include mouse, rat, hamster and rabbit.

The methods for preparing total RNA from a hybridoma cell include the guanidine thiocyanate-cesium trifluoroacetate method [*Methods in Enzymol.*, 154, 3 (1987)], and the methods for preparing mRNA from the total RNA include the oligo (dT) immobilized cellulose column method [*Molecular Cloning, A Laboratory Manual*, Cold Spring Harbor Lab. Press (1989)]. Examples of the kits for preparing mRNA from a hybridoma cell include Fast Track mRNA Isolation Kit (manufactured by Invitrogen) and Quick Prep mRNA Purification Kit (manufactured by Pharmacia).

The methods for synthesizing the cDNA and preparing the cDNA library include conventional methods [*Molecular Cloning, A Laboratory Manual*, Cold Spring Harbor Lab. Press (1989), *Current Protocols in Molecular Biology*, Supplement 1-34], or methods using commercially available kits such as SuperScript™ Plasmid System for cDNA Synthesis and Plasmid Cloning (manufactured by GIBCO BRL) and ZAP-cDNA Synthesis Kit (manufactured by Stratagene).

In preparing the cDNA library, the vector for integrating the cDNA synthesized using the mRNA extracted from a hybridoma cell as a template may be any vector so long as the cDNA can be integrated. Examples of suitable vectors include ZAP Express [*Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning: A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* for introducing the cDNA library constructed with a phage or plasmid vector, any *Escherichia coli* can be used so long as the cDNA library can be introduced, expressed and maintained. Examples of suitable *Escherichia coli* include XL1-Blue MRF' [*Strategies*, 5, 81 (1992)], C600 [*Genetics*, 39, 440 (1954)], Y1088, Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

The methods for selecting the cDNA clones encoding VH and VL of a non-human animal-derived antibody from the cDNA library include colony hybridization or plaque hybridization [*Molecular Cloning, A Laboratory Manual*, Cold Spring Harbor Laboratory Press (1989)] using an isotope- or fluorescence-labeled probe. It is also possible to prepare the cDNAs encoding VH and VL by preparing primers and carrying out PCR [*Molecular Cloning, A Laboratory Manual*, Cold Spring Harbor Laboratory Press (1989), *Current Protocols in Molecular Biology*, Supplement 1-34] using the cDNA or cDNA library as a template.

The nucleotide sequences of the cDNAs selected by the above methods can be determined by cleaving the cDNAs with appropriate restriction enzymes, cloning the fragments into a plasmid such as pBluescript SK(–) (manufactured by STRATAGENE), and then analyzing the sequences by generally employed nucleotide sequence analyzing methods such as the dideoxy method of Sanger, et al. [*Proc. Natl. Acad. Sci. USA*, 74, 5463 (1977)] or by use of nucleotide sequence analyzers such as ABI PRISM 377 DNA Sequencer (manufactured by Applied Biosystems).

The full length of amino acid sequences of VH and VL are deduced from the determined nucleotide sequences and compared with the full length of amino acid sequences of VH and VL of a known antibody [*Sequences of Proteins of Immunological Interest*, US Dept. Health and Human Services (1991)], whereby it can be confirmed that the obtained cDNAs encode amino acid sequences which completely comprise VH and VL of the antibody including secretory signal sequences.

Further, when the amino acid sequence of an antibody variable region or the nucleotide sequence of DNA encoding the variable region is already known, the DNA can be obtained by the following methods.

When the amino acid sequence is known, the DNA can be obtained by designing a DNA sequence encoding the variable region taking into consideration the frequency of codon usage [*Sequences of Proteins of Immunological Interest*, US Dept. Health and Human Services (1991)], synthesizing several synthetic DNAs constituting approximately 100-nucleotides based on the designed DNA sequence, and carrying out PCR using the synthetic DNAs. When the nucleotide sequence is known, the DNA can be obtained by synthesizing several synthetic DNAs constituting approximately 100-nucleotides based on the nucleotide sequence information and carrying out PCR using the synthetic DNAs.

(3) Analysis of the Amino Acid Sequence of the V Region of an Antibody from a Non-Human Animal By comparing the full length of amino acid sequences of VH and VL of the antibody including secretory signal sequences with the amino acid sequences of VH and VL of a known antibody [*Sequences of Proteins of Immunological Interest*, US Dept. Health and Human Services (1991)], it is possible to deduce the length of the secretory signal sequences and the N-terminal amino acid sequences and further to know the subgroup to which the antibody belongs. In addition, the amino acid sequences of CDRs of VH and VL can be deduced in a similar manner.

(4) Construction of a Human Chimeric Antibody Expression Vector

A human chimeric antibody expression vector can be constructed by inserting the cDNAs encoding VH and VL of an antibody of a non-human animal into sites upstream of the genes encoding CH and CL of a human antibody in the vector for expression of recombinant antibody composition described in the above 1 (1). For example, a human chimeric antibody expression vector can be constructed by ligating the cDNAs encoding VH and VL of an antibody of a non-human animal respectively to synthetic DNAs comprising the 3'-terminal nucleotide sequences of VH and VL of an antibody of a non-human animal and the 5'-terminal nucleotide sequences of CH and CL of a human antibody and also having recognition sequences for appropriate restriction enzymes at both ends, and inserting them into sites upstream of the genes encoding CH and CL of a human antibody in the vector for recombinant antibody composition described in the above 1 (1) so as to express them in an appropriate form.

(5) Construction of cDNA Encoding V Region of a Humanized Antibody cDNAs encoding VH and VL of a humanized antibody can be constructed in the following manner. First, amino acid sequences of FRs of VH and VL of a human antibody for grafting CDRs of VH and VL of a non-human animal-derived antibody are selected. The amino acid sequences of FRs of VH and VL of a human antibody may be any of those from human antibodies. Suitable sequences include the amino acid sequences of FRs of VHs and VLs of human antibodies registered at databases such as Protein Data Bank, and the amino acid sequences common to subgroups of FRs of VHs and VLs of human antibodies [*Sequences of Proteins of Immunological Interest*, US Dept. Health and Human Services (1991)]. In order to prepare a humanized antibody having a sufficient activity, it is preferred to select amino acid sequences having a homology of as high as possible (at least 60% or more) with the amino acid sequences of FRs of VH and VL of the desired non-human animal-derived antibody.

Next, the amino acid sequences of CDRs of VH and VL of the desired non-human animal-derived antibody are grafted to the selected amino acid sequences of FRs of VH and VL of a human antibody to design amino acid sequences of VH and VL of a humanized antibody. The designed amino acid sequences are converted into DNA sequences taking into consideration the frequency of codon usage in the nucleotide sequences of antibody genes [*Sequences of Proteins of Immunological Interest*, US Dept. Health and Human Services (1991)], and DNA sequences encoding the amino acid sequences of VH and VL of the humanized antibody are designed. Several synthetic DNAs constituting approximately 100-nucleotides are synthesized based on the designed DNA sequences, and PCR is carried out using the synthetic DNAs. It is preferred to design 4 to 6 synthetic DNAs for each of the H chain and the L chain in view of the reaction efficiency of PCR and the lengths of DNAs that can be synthesized.

Cloning into the vector for expression of the recombinant antibody composition of the present invention constructed in the above 1 (1) can be easily carried out by introducing recognition sequences for appropriate restriction enzymes to the 5'-terminals of synthetic DNAs present on both ends. After the PCR, the amplification products are cloned into a plasmid such as pBluescript SK(−) (manufactured by STRATAGENE) and the nucleotide sequences are determined by the method described in the above 1 (2) to obtain a plasmid carrying DNA sequences encoding the amino acid sequences of VH and VL of the desired humanized antibody.

(6) Modification of the Amino Acid Sequence of V Region of a Humanized Antibody

It is known that a humanized antibody prepared merely by grafting CDRs of VH and VL of a non-human animal-derived antibody to FRs of VH and VL of a human antibody has a lower antigen-binding activity compared with the original non-human animal-derived antibody [*BIO/TECHNOLOGY*, 9, 266 (1991)]. This is probably because in VH and VL of the original non-human animal-derived antibody, not only CDRs but also some of the amino acid residues in FRs are involved directly or indirectly in the antigen-binding activity, and such amino acid residues are replaced by amino acid residues of FRs of VH and VL of the human antibody by CDR grafting. In order to solve this problem, attempts have been made in the preparation of a humanized antibody to raise the lowered antigen-binding activity by identifying the amino acid residues in the amino acid sequences of FRs of VH and VL of a human antibody which are directly relating to the binding to an antigen or which are indirectly relating to it through interaction with amino acid residues in CDRs or maintenance of the three-dimensional structure of antibody, and modifying such amino acid residues to those derived from the original non-human animal-derived antibody [*BIO/TECHNOLOGY*, 9, 266 (1991)].

In the preparation of a humanized antibody, it is most important to efficiently identify the amino acid residues in FR which are relating to the antigen-binding activity. For the efficient identification, construction and analyses of the three-dimensional structures of antibodies have been carried out by X ray crystallography [*J. Mol. Biol.*, 112, 535 (1977)], computer modeling [*Protein Engineering*, 7, 1501 (1994)], etc. Although these studies on the three-dimensional structures of antibodies have provided much information useful for the preparation of humanized antibodies, there is no established method for preparing a humanized antibody that is adaptable to any type of antibody. That is, at present, it is still necessary to make trial-and-error approaches, e.g., preparation of several modifications for each antibody and examination of each modification for the relationship with the antigen-binding activity.

Modification of the amino acid residues in FRs of VH and VL of a human antibody can be achieved by PCR as described in the above 1 (5) using synthetic DNAs for modification. The nucleotide sequence of the PCR amplification product is determined by the method described in the above 1 (2) to confirm that the desired modification has been achieved.

(7) Construction of a Humanized Antibody Expression Vector

A humanized antibody expression vector can be constructed by inserting the cDNAs encoding VH and VL of the humanized antibody constructed in the above 1 (5) and (6) into sites upstream of the genes encoding CH and CL of a human antibody in the vector for expression of the recombinant antibody composition of the present invention described in the above 1 (1). For example, a humanized antibody expression vector can be constructed by introducing recognition sequences for appropriate restriction enzymes to the 5'-terminals of synthetic DNAs present on both ends among the synthetic DNAs used for constructing VH and VL of the humanized antibody in the above 1 (5) and (6), and inserting them into sites upstream of the genes encoding CH and CL of a human antibody in the vector for expression of the recombinant antibody of the present invention described in the above 1 (1) so as to express them in an appropriate form.

(8) Stable Production of a Humanized Antibody

Transformants capable of stably producing a human chimeric antibody and a humanized antibody can be obtained by introducing the human chimeric antibody or humanized antibody expression vectors described in the above 1 (4) and (7) into appropriate animal cells.

Introduction of the humanized antibody expression vector into an animal cell can be carried out by electroporation [Japanese Published Unexamined Patent Application No. 257891/90; Cytotechnology, 3, 133 (1990)], etc.

As the animal cell for introducing the human chimeric antibody or humanized antibody expression vector, any animal cell capable of producing a human chimeric antibody or a humanized antibody can be used.

Examples of the animal cells include mouse myeloma cell lines NS0 and SP2/0, Chinese hamster ovary cells CHO/dhfr− and CHO/DG44, rat myeloma cell lines YB2/0 and IR983F, Syrian hamster kidney-derived BHK cell, and human myeloma cell line Namalwa. Chinese hamster ovary cell CHO/DG44 and rat myeloma cell line YB2/0 are preferred.

After the introduction of the human chimeric antibody or humanized antibody expression vector, the transformant capable of stably producing the human chimeric antibody or the humanized antibody can be selected using a medium for animal cell culture containing an agent such as G418 sulfate (hereinafter referred to as G418; manufactured by SIGMA) according to the method described in Japanese Published Unexamined Patent Application No. 257891/90. Examples of the media for animal cell culture include RPMI1640 medium (manufactured by Nissui Pharmaceutical Co., Ltd.), GIT medium (manufactured by Nihon Pharmaceutical Co., Ltd.), EX-CELL 302 medium (manufactured by JRH), IMDM medium (manufactured by GIBCO BRL), Hybridoma-SFM medium (manufactured by GIBCO BRL), and media prepared by adding various additives such as fetal calf serum (hereinafter referred to as FCS) to these media. By culturing the obtained transformant in the medium, the human chimeric antibody or the humanized antibody can be formed and accumulated in the culture supernatant. The amount and the antigen-binding activity of the human chimeric antibody or the humanized antibody produced in the culture supernatant can be measured by enzyme-linked immunosorbent assay [hereinafter referred to as ELISA; *Antibodies: A Laboratory Manual*, Cold Spring Harbor Laboratory, Chapter 14 (1998); *Monoclonal Antibodies: Principles and Practice*, Academic Press Limited (1996)] or the like. The amount of the human chimeric antibody or the humanized antibody to be produced by the transformant can be increased by utilizing a DHFR gene amplification system or the like according to the method described in Japanese Published Unexamined Patent Application No. 257891/90.

The human chimeric antibody or the humanized antibody can be purified from the culture supernatant of the transformant using a protein A column [*Antibodies: A Laboratory Manual*, Cold Spring Harbor Laboratory, Chapter 8 (1988); *Monoclonal Antibodies: Principles and Practice*, Academic Press Limited (1996)]. In addition, purification methods generally employed for the purification of proteins can also be used. For example, the purification can be carried out by combinations of gel filtration, ion exchange chromatography, ultrafiltration and the like. The molecular weight of the H chain, L chain or whole antibody molecule of the purified human chimeric antibody or humanized antibody can be measured by SDS-denatured polyacrylamide gel electrophoresis [hereinafter referred to as SDS-PAGE; *Nature*, 227, 680 (1970)], Western blotting [*Antibodies: A Laboratory Manual*, Cold Spring Harbor Laboratory, Chapter 12 (1988); *Monoclonal Antibodies: Principles and Practice*, Academic Press Limited (1996)], etc.

Shown above is the method for producing the antibody composition using an animal cell as the host. The antibody composition can also be produced using yeast, an insect cell, a plant cell, an animal individual or a plant individual by similar methods.

Accordingly, when the host cell is capable of expressing an antibody molecule, the antibody composition of the present invention can be produced by introducing a gene encoding an antibody into the host cell which expresses an antibody molecule, culturing the cell, and purifying the desired antibody composition from the culture.

When yeast is used as the host cell, YEP13 (ATCC 37115), YEp24 (ATCC 37051), YCp50 (ATCC 37419), etc. can be used as the expression vector.

As the promoter, any promoters capable of expressing in yeast strains can be used. Suitable promoters include promoters of genes of the glycolytic pathway such as hexosekinase, PHO5 promoter, PGK promoter, GAP promoter, ADH promoter, gal 1 promoter, gal 10 promoter, heat shock protein promoter, MFα1 promoter and CUP 1 promoter.

Examples of suitable host cells are microorganisms belonging to the genera *Saccharomyces*, *Schizosaccharomyces*, *Kluyveromyces*, *Trichosporon* and *Schwanniomyces*, and specifically, *Saccharomyces cerevisiae*, *Schizosaccharomyces pombe*, *Kluyveromyces lactis*, *Trichosporon pullulans*, *Schwanniomyces alluvius* and the like.

Introduction of the recombinant vector can be carried out by any of the methods for introducing DNA into yeast, for example, electroporation [*Methods Enzymol.*, 194, 182 (1990)], the spheroplast method [*Proc. Natl. Acad. Sci. USA*, 84, 1929 (1978)], the lithium acetate method [*J. Bacteriology*, 153, 163 (1983)] and the method described in *Proc. Natl. Acad. Sci. USA*, 75, 1929 (1978).

When an animal cell is used as the host cell, pcDNAI, pcDM8 (commercially available from Funakoshi Co., Ltd.), pAGE107 [Japanese Published Unexamined Patent Application No. 22979/91; Cytotechnology, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen Corp.), pREP4 (manufactured by Invitrogen Corp.), pAGE103 [*J. Biochemistry*, 101, 1307 (1987)], pAGE210, etc. can be used as the expression vector.

As the promoter, any promoters capable of expressing in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, etc. The enhancer of IE gene of human CMV may be used in combination with the promoter.

Examples of suitable host cells are human-derived Namalwa cells, monkey-derived COS cells, Chinese hamster-derived CHO cells, HBT5637 (Japanese Published Unexamined Patent Application No. 299/88), rat myeloma cells, mouse myeloma cells, cells derived from Syrian hamster kidney, embryonic stem cells, fertilized egg cells and the like.

When an insect cell is used as the host cell, the protein can be expressed by the methods described in *Current Protocols in Molecular Biology; Baculovirus Expression Vectors, A Laboratory Manual*, W. H. Freeman and Company, New York (1992); Bio/Technology, 6, 47 (1988), etc.

That is, the expression vector and a baculovirus are cotransfected into insect cells to obtain a recombinant virus in the culture supernatant of the insect cells, and then insect cells are infected with the recombinant virus, whereby the protein can be expressed.

The gene introducing vectors useful in this method include pVL1392, pVL1393, pBlueBacIII (products of Invitrogen Corp.) and the like.

An example of the baculovirus is Autographa californica nuclear polyhedrosis virus, which is a virus infecting insects belonging to the family Barathra.

Examples of the insect cells are *Spodoptera frugiperda* ovarian cells Sf9 and Sf21 [*Current Protocols in Molecular Biology; Baculovirus Expression Vectors, A Laboratory Manual*, W.H. Freeman and Company, New York (1992)] and *Trichoplusia ni* ovarian cell High 5 (manufactured by Invitrogen Corp.).

Cotransfection of the above expression vector and the above baculovirus into insect cells for the preparation of the recombinant virus can be carried out by the calcium phosphate method (Japanese Published Unexamined Patent Application No. 227075/90), lipofection [*Proc. Natl. Acad. Sci. USA*, 84, 7413 (1987)], etc.

When a plant cell is used as the host cell, Ti plasmid, tobacco mosaic virus vector, etc. can be used as the expression vector.

As the promoter, any promoters capable of expressing in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Introduction of the recombinant vector can be carried out by any of the methods for introducing DNA into animal cells, for example, electroporation [*Cytotechnology*, 3, 133 (1990)], the calcium phosphate method (Japanese Published Unexamined Patent Application No. 227075/90), lipofection [*Proc. Natl. Acad. Sci. USA*, 84, 7413 (1987)], the injection method (*Manipulating the Mouse Embryo, A Laboratory Manual*), the method using particle gun (gene gun) (Japanese Patent Nos. 2606856 and 2517813), the DEAE-dextran method [*Biomanual Series 4—Methods of Gene Transfer, Expression and Analysis* (Yodosha), edited by Takashi Yokota and Kenichi Arai (1994)] and the virus vector method (*Manipulating the Mouse Embryo, A Laboratory Manual*).

Expression of the gene encoding the antibody can be carried out not only by direct expression but also by secretory production, expression of a fusion protein of the Fc region and another protein, etc. according to the methods described in *Molecular Cloning*, Second Edition.

The antibody composition can be produced by culturing the transformant obtained as above in a medium, allowing the antibody molecules to form and accumulate in the culture, and recovering them from the culture. Culturing of the transformant in a medium can be carried out by conventional methods for culturing the host cell.

For the culturing of the transformant obtained by using a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate, calcium carbonate and the like.

Culturing is usually carried out under aerobic conditions, for example, by shaking culture or submerged spinner culture under aeration. The culturing temperature is preferably 15 to 40° C., and the culturing period is usually 16 hours to 7 days. The pH is maintained at 3.0 to 9. during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with a recombinant vector using an inducible promoter is cultured, an inducer may be added to the medium, if necessary. For example, in the case of a microorganism transformed with a recombinant vector using lac promoter, isopropyl-β-D-thiogalactopyranoside or the like may be added to the medium; and in the case of a microorganism transformed with a recombinant vector using trp promoter, indoleacrylic acid or the like may be added.

For the culturing of the transformant obtained by using an animal cell as the host, generally employed media such as RPMI1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)] and Whitten's medium [*Developmental Engineering Experimentation Manual—Preparation of Transgenic Mice* (Kodansha), edited by Motoya Katsuki (1987)], media prepared by adding fetal calf serum or the like to these media, etc. can be used as the medium.

Culturing is usually carried out under conditions of pH 6.0 to 8.0 at 30 to 40° C. for 1 to 7 days in the presence of 5% $CO_2$.

If necessary, antibiotics such as kanamycin and penicillin may be added to the medium during the culturing.

For the culturing of the transformant obtained by using an insect cell as the host, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.) and Grace's Insect Medium [*Nature*, 195, 788 (1962)] can be used as the medium.

Culturing is usually carried out under conditions of pH 6.0 to 7.0 at 25 to 30° C. for 1 to 5 days.

If necessary, antibiotics such as gentamicin may be added to the medium during the culturing.

The transformant obtained by using a plant cell as the host may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out under conditions of pH 5.0 to 9.0 at 20 to 40° C. for 3 to 60 days.

If necessary, antibiotics such as kanamycin and hygromycin may be added to the medium during the culturing.

As described above, the antibody composition can be produced by culturing, according to a conventional culturing method, the transformant derived from an animal cell or a plant cell and carrying an expression vector into which DNA encoding the antibody molecule has been integrated, allowing the antibody composition to form and accumulate, and recovering the antibody composition from the culture.

Expression of the gene encoding the antibody can be carried out not only by direct expression but also by secretory production, fusion protein expression, etc. according to the methods described in *Molecular Cloning*, Second Edition.

The antibody composition may be produced by intracellular expression in host cells, may be produced by extracellular secretion from host cells or may be produced on outer membranes of host cells. A desirable production method can be adopted by changing the kind of the host cells used or the structure of the antibody molecule to be produced.

When the antibody composition is produced in host cells or on outer membranes of host cells, it is possible to force the antibody composition to be secreted outside the host cells by applying the method of Paulson, et al. [*J. Biol. Chem.*, 264, 17619 (1989)], the method of Lowe, et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, etc.

That is, it is possible to force the desired antibody molecule to be secreted outside the host cells by inserting DNA encoding the antibody molecule and DNA encoding a signal peptide suitable for the expression of the antibody molecule into an expression vector, introducing the expression vector into the host cells, and then expressing the antibody molecule by use of recombinant DNA techniques.

It is also possible to increase the amount of the antibody composition to be produced by utilizing a gene amplification system using a dihydrofolate reductase gene or the like according to the method described in Japanese Published Unexamined Patent Application No. 227075/90.

Further, the antibody composition can be produced using an animal individual into which a gene is introduced (non-human transgenic animal) or a plant individual into which a gene is introduced (transgenic plant) constructed by redifferentiating the animal or plant cells into which genes are introduced.

When the transformant is an animal individual or plant individual, the antibody composition can be produced by rearing or cultivating the animal or plant in a usual manner, allowing the antibody composition to form and accumulate therein, and collecting the antibody composition from the animal individual or plant individual.

Production of the antibody composition using an animal individual can be carried out, for example, by producing the desired antibody composition in an animal constructed by introducing the gene according to known methods [*American Journal of Clinical Nutrition*, 63, 639S (1996); *American Journal of Clinical Nutrition*, 63, 627S (1996); *Bio/Technology*, 9, 830 (1991)].

In the case of an animal individual, the antibody composition can be produced, for example, by raising a non-human transgenic animal into which DNA encoding the antibody molecule is introduced, allowing the antibody composition to form and accumulate in the animal, and collecting the antibody composition from the animal. The places where the antibody composition is formed and accumulated include milk (Japanese Published Unexamined Patent Application No. 309192/88), egg or the like of the animal. As the promoter in this process, any promoters capable of expressing in an animal can be used. Preferred promoters include mammary gland cell-specific promoters such as a casein promoter, β casein promoter, β lactoglobulin promoter and whey acidic protein promoter.

Production of the antibody composition using a plant individual can be carried out, for example, by cultivating a transgenic plant into which DNA encoding the antibody molecule is introduced according to known methods [*Soshiki Baiyo (Tissue Culture)*, 20 (1994); *Soshiki Baiyo (Tissue Culture)*, 21 (1995); *Trends in Biotechnology*, 15, 45 (1997)], allowing the antibody composition to form and accumulate in the plant, and collecting the antibody composition from the plant.

When the antibody composition produced by the transformant into which the gene encoding the antibody molecule is introduced is expressed in a soluble form in cells, the cells are recovered by centrifugation after the completion of culturing and suspended in an aqueous buffer, followed by disruption using a sonicator, French press, Manton Gaulin™ homogenizer, Dynomill™ or the like to obtain a cell-free extract. A purified preparation of the antibody composition can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION™ HPA-75 (manufactured by Mitsubishi Chemical Corporation), cation exchange chromatography using resins such as S-Sepharose FF (manufactured by Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the antibody composition is expressed as an insoluble body in cells, the cells are similarly recovered and disrupted, followed by centrifugation to recover the insoluble body of the antibody composition as a precipitate fraction. The recovered insoluble body of the antibody composition is solubilized with a protein-denaturing agent. The solubilized antibody solution is diluted or dialyzed, whereby the antibody composition is renatured to have normal three-dimensional structure. Then, a purified preparation of the antibody composition can be obtained by the same isolation and purification steps as described above.

When the antibody composition is extracellularly secreted, the antibody composition or its derivative can be recovered in the culture supernatant. That is, the culture is treated by the same means as above, e.g., centrifugation, to obtain the culture supernatant. A purified preparation of the antibody composition can be obtained from the culture supernatant by using the same isolation and purification methods as described above.

2. Preparation of Recombinant Antibody Composition-Producing Cell of the Present Invention The cell producing the recombinant antibody composition having high ADCC activity as well as high CDC activity among the recombinant antibody compositions of the present invention can be produced by preparing a host cell used for the production of the recombinant antibody composition of the present invention by the following techniques and then introducing the human chimeric antibody or humanized antibody expression vector described in the above 1 (4) and (7) into the host cell.

Specifically, a cell in which an enzyme relating to the modification of the N-glycoside-linked sugar chain bound to the Fc region of an antibody molecule, that is, an enzyme relating to the synthesis of an intracellular sugar nucleotide, GDP-fucose and/or an enzyme relating to the modification of a sugar chain in which 1-position of fucose is bound to 6-position of N-acetylglucosamine in the reducing terminal through α-bond in the complex type N-glycoside-linked sugar chain is inactivated is selected, or a cell obtained by various artificial techniques described below can be used as a host cell. The details are described below.

(1) Gene Disruption Technique Targeting at a Gene Encoding an Enzyme

The host cell used for the production of the cell producing the antibody having high ADCC activity (hereinafter referred to as high ADCC activity antibody) can be prepared by a gene disruption technique targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain. Examples of the enzymes relating to the synthesis of an intracellular sugar nucleotide, GDP-fucose include GDP-mannose 4,6-dehydratase (hereinafter referred to as GMD) and GDP-4-keto-6-deoxy-D-mannose-3,5-epimerase (hereinafter referred to as Fx).

Examples of the enzymes relating to the modification of a sugar chain in which 1-position of fucose is bound to 6-position of N-acetylglucosamine in the reducing terminal through α-bond in a complex type N-glycoside-linked sugar chain include α1,6-fucosyltransferase, α-L-fucosidase, and the like. The gene as used herein includes DNA and RNA.

The method of gene disruption may be any method capable of disrupting the gene encoding the enzyme. Useful methods include the antisense method, the ribozyme method, the homologous recombination method, the RNA-DNA oligonucleotide method (hereinafter referred to as the RDO method), the RNA interference method (hereinafter referred to as the RNAi method), the method using a retrovirus and the method using a transposon, and the like. These methods are specifically described below.

(a) Preparation of the Host Cell for the Production of the High ADCC Activity Antibody-Producing Cell by the Antisense Method or the Ribozyme Method The host cell used for the production of the high ADCC activity antibody-producing cell can be prepared by the antisense method or the ribozyme method described in *Cell Technology*, 12, 239 (1993); *BIO/TECHNOLOGY*, 17, 1097 (1999); *Hum. Mol. Genet.*, 5, 1083 (1995); *Cell Technology*, 13, 255 (1994); *Proc. Natl. Acad. Sci. U.S.A.*, 96, 1886 (1999); and the like targeting at a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain, for example, in the following manner.

A cDNA or a genomic DNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain is prepared.

The nucleotide sequence of the prepared cDNA or genomic DNA is determined.

Based on the determined DNA sequence, an antisense gene or a ribozyme of appropriate length is designed which comprises a DNA moiety encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, non-translated regions or introns.

In order to express the antisense gene or ribozyme in a cell, a recombinant vector is prepared by inserting a fragment or full-length of the prepared DNA into a site downstream of a promoter in an appropriate expression vector.

A transformant can be obtained by introducing the recombinant vector into a host cell suited for the expression vector.

The host cell used for the production of the recombinant antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more of the present invention can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. The host cell used for the production of the high ADCC activity antibody-producing cell can also be obtained by selecting a transformant using, as an index, the sugar chain structure of a glycoprotein on the cell membrane or the sugar chain structure of the produced antibody molecule.

As the host cell used for the production of the high ADCC activity antibody-producing cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the designed antisense gene or ribozyme. Examples of the expression vectors include those described in the above 1.

Introduction of a gene into various host cells can be carried out by the methods suitable for introducing a recombinant vector into various host cells described in the above 1.

Selection of a transformant using, as an index, the activity of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain can be carried out, for example, by the following methods.

Methods for Selecting a Transformant

A cell in which the activity of an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain is deleted can be selected by measuring the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain using biochemical methods or genetic engineering techniques described in *Shin Seikagaku Jikken Koza (New Lectures on Experiments in Biochemistry)* 3—*Saccharides I, Glycoprotein* (Tokyo Kagaku Dojin), edited by The Japanese Biochemical Society (1988); *Cell Technology, Extra Edition, Experimental Protocol Series, Glycobiology Experimental Protocol, Glycoprotein, Glycolipid and Proteoglycan* (Shujunsha), edited by Naoyuki Taniguchi, Akemi Suzuki, Kiyoshi Furukawa and Kazuyuki Sugawara (1996); *Molecular Cloning,* Second Edition; *Current Protocols in Molecular Biology;* and the like. An example of the biochemical methods is a method in which the enzyme activity is evaluated using an enzyme-specific substrate. Examples of the genetic engineering techniques include Northern analysis and RT-PCR in which the amount of mRNA for a gene encoding the enzyme is measured.

Selection of a transformant using, as an index, the sugar chain structure of a glycoprotein on the cell membrane can be carried out, for example, by the method described in 2(5) below. Selection of a transformant using, as an index, the sugar chain structure of a produced antibody molecule can be carried out, for example, by the methods described in 4 or 5 below.

Preparation of a cDNA encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain can be carried out, for example, by the following method.

Preparation Method of cDNA

Total RNA or mRNA is prepared from a various host cell tissue or cell.

A cDNA library is prepared from the obtained total RNA or mRNA.

Degenerative primers are prepared based on the amino acid sequence of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain, and a gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain is obtained by PCR using the prepared cDNA library as a template.

A DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be obtained by screening the cDNA library using the obtained gene fragment as a probe.

As the mRNA of a human or non-human animal tissue or cell, commercially available one (for example, manufactured by Clontech) may be used, or it may be prepared from a human or non-human animal tissue or cell in the following manner.

The methods for preparing total RNA from a human or non-human animal tissue or cell include the guanidine thiocyanate-cesium trifluoroacetate method [*Methods in Enzymology,* 154, 3 (1987)], the acidic guanidine thiocyanate-phenol-chloroform (AGPC) method [*Analytical Biochemistry,* 162, 156 (1987); *Experimental Medicine,* 9, 1937 (1991)] and the like.

The methods for preparing mRNA as poly(A)⁺RNA from the total RNA include the oligo (dT) immobilized cellulose column method (*Molecular Cloning,* Second Edition).

It is also possible to prepare mRNA by using a commercially available kit such as Fast Track mRNA Isolation Kit (manufactured by Invitrogen) or Quick Prep™ mRNA Purification Kit (manufactured by Pharmacia).

A cDNA library is prepared from the obtained mRNA of a human or non-human animal tissue or cell. The methods for preparing the cDNA library include the methods described in *Molecular Cloning,* Second Edition; *Current Protocols in Molecular Biology; A Laboratory Manual,* 2nd Ed. (1989); etc., and methods using commercially available kits such as SuperScript™ Plasmid System for cDNA Synthesis and Plasmid Cloning (manufactured by Life Technologies) and ZAP-cDNA™ Synthesis Kit (manufactured by STRATAGENE).

As the cloning vector for preparing the cDNA library, any vectors, e.g. phage vectors and plasmid vectors, can be used so long as they are autonomously replicable in *Escherichia coli* K12. Examples of suitable vectors include ZAP™ Express [manufactured by STRATAGENE; *Strategies,* 5, 58 (1992)], pBluescript II SK(+) [*Nucleic Acids Research,* 17, 9494 (1989)], λZAP II (manufactured by STRATAGENE), λgt10, λgt11 [*DNA Cloning, A Practical Approach,* 1, 49 (1985)], λTriplEx (manufactured by Clontech), λExCell (manufactured by Pharmacia), pT7T318U (manufactured by Pharmacia), pcD2 [*Mol. Cell. Biol.,* 3, 280 (1983)], pUC18 [*Gene,* 33, 103 (1985)], and the like.

Any microorganism can be used as the host microorganism for preparing the cDNA library, but *Escherichia coli* is preferably used. Examples of suitable host microorganisms are *Escherichia coli* XL1-Blue MRF' [manufactured by STRATAGENE; *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)], and the like.

The cDNA library may be used as such in the following analysis. Alternatively, in order to efficiently obtain full-length cDNAs by decreasing the ratio of partial cDNAs, a cDNA library prepared using the oligo-cap method developed by Sugano, et al. [*Gene*, 138, 171 (1994); *Gene*, 200, 149 (1997); *Protein, Nucleic Acid and Enzyme*, 41, 603 (1996); *Experimental Medicine*, 11, 2491 (1993); *cDNA Cloning* (Yodosha) (1996); *Methods for Preparing Gene Libraries* (Yodosha) (1994)] may be used in the following analysis.

Degenerative primers specific for the 5'-terminal and 3'-terminal nucleotide sequences of a nucleotide sequence presumed to encode the amino acid sequence of an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain are prepared based on the amino acid sequence of the enzyme. A gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be obtained by DNA amplification by PCR [*PCR Protocols*, Academic Press (1990)] using the prepared cDNA library as a template.

It can be confirmed that the obtained gene fragment is a DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain by analyzing the nucleotide sequence by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

A DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be obtained from the cDNA or cDNA library synthesized from the mRNA contained in a human or non-human animal tissue or cell by colony hybridization or plaque hybridization (*Molecular Cloning*, Second Edition) using the above gene fragment as a probe.

A cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can also be obtained by amplification by PCR using the cDNA or cDNA library synthesized from the mRNA contained in a human or non-human animal tissue or cell as a template and using the primers used for obtaining the gene fragment encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain.

The nucleotide sequence of the DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be determined by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer™ (manufactured by Applied Biosystems).

By carrying out a search of nucleotide sequence databases such as GenBank, EMBL or DDBJ using a homology search program such as BLAST based on the determined nucleotide sequence of the cDNA, it can be confirmed that the obtained DNA is a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain among the genes in the nucleotide sequence database.

Examples of the nucleotide sequences of the genes encoding the enzyme relating to the synthesis of an intracellular sugar nucleotide, GDP-fucose obtained by the above methods include the nucleotide sequences represented by SEQ ID NO:18 or 20.

Examples of the nucleotide sequences of the genes encoding the enzyme relating to the modification of a sugar chain in which 1-position of fucose is bound to 6-position of N-acetylglucosamine in the reducing terminal through α-bond in a complex type N-glycoside-linked sugar chain obtained by the above methods include the nucleotide sequence represented by SEQ ID NO:22 or 23.

The cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can also be obtained by chemical synthesis with a DNA synthesizer such as DNA Synthesizer Model 392 (manufactured by Perkin Elmer) utilizing the phosphoamidite method based on the determined nucleotide sequence of the desired DNA.

Preparation of a genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be carried out, for example, by the following method.

Method for Preparing Genomic DNA

The genomic DNA can be prepared by known methods described in *Molecular Cloning*, Second Edition, *Current Protocols in Molecular Biology*, etc. In addition, the genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can also be obtained by using a kit such as Genomic DNA Library Screening System (manufactured by Genome Systems) or Universal GenomeWalker™ Kits (manufactured by CLONTECH).

The nucleotide sequence of the DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be determined by generally employed nucleotide analyzing methods such as the dideoxy method of Sanger, et al. [*Proc. Natl. Acad. Sci. U.S.A.,* 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the genomic DNA, it can be confirmed that the obtained DNA is a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain among the genes in the nucleotide sequence database.

The genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can also be obtained by chemical synthesis with a DNA synthesizer such as DNA Synthesizer Model 392 (manufactured by Perkin Elmer) utilizing the phosphoamidite method based on the determined nucleotide sequence of the DNA.

Examples of the nucleotide sequences of the genomic DNAs encoding the enzyme relating to the synthesis of an intracellular sugar nucleotide, GDP-fucose obtained by the above methods include the nucleotide sequences represented by SEQ ID NOs:26, 27, 28 and 29.

An example of the nucleotide sequence of the genomic DNA encoding the enzyme relating to the modification of a sugar chain in which 1-position of fucose is bound to 6-position of N-acetylglucosamine in the reducing terminal through α-bond in a complex type N-glycoside-linked sugar chain obtained by the above methods is the nucleotide sequence represented by SEQ ID NO:30.

The host cell used for the production of the antibody composition of the present invention can also be obtained without using an expression vector by directly introducing into a host cell an antisense oligonucleotide or ribozyme designed based on the nucleotide sequence encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain.

The antisense oligonucleotide or ribozyme can be prepared by known methods or by using a DNA synthesizer. Specifically, based on the sequence information on an oligonucleotide having a sequence corresponding to 5 to 150, preferably 5 to 60, more preferably 10 to 40 continuous nucleotides in the nucleotide sequence of the cDNA and genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, an oligonucleotide corresponding to the sequence complementary to the above oligonucleotide (antisense oligonucleotide) or a ribozyme comprising the oligonucleotide sequence can be synthesized.

The oligonucleotide includes oligo RNA and derivatives of the oligonucleotide (hereinafter referred to as oligonucleotide derivatives).

The oligonucleotide derivatives include an oligonucleotide derivative wherein the phosphodiester bond in the oligonucleotide is converted to a phosophorothioate bond, an oligonucleotide derivative wherein the phosphodiester bond in the oligonucleotide is converted to an N3'-P5' phosphoamidate bond, an oligonucleotide derivative wherein the ribose-phosphodiester bond in the oligonucleotide is converted to a peptide-nucleic acid bond, an oligonucleotide derivative wherein the uracil in the oligonucleotide is substituted with C-5 propynyluracil, an oligonucleotide derivative wherein the uracil in the oligonucleotide is substituted with C-5 thiazolyluracil, an oligonucleotide derivative wherein the cytosine in the oligonucleotide is substituted with C-5 propynylcytosine, an oligonucleotide derivative wherein the cytosine in the oligonucleotide is substituted with phenoxazine-modified cytosine, an oligonucleotide derivative wherein the ribose in the oligonucleotide is substituted with 2'-O-propylribose, and an oligonucleotide derivative wherein the ribose in the oligonucleotide is substituted with 2'-methoxyethoxyribose [*Cell Technology,* 16, 1463 (1997)].

(b) Preparation of the Host Cell for the Production of High ADCC Activity Antibody-Producing Cell by the Homologous Recombination Method The host cell used for the production of the high ADCC activity antibody-producing cell of the present invention can be prepared by modifying a target gene on the chromosome by the homologous recombination method targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain.

Modification of the target gene on the chromosome can be carried out by using the methods described in *Manipulating the Mouse Embryo, A Laboratory Manual,* Second Edition, Cold Spring Harbor Laboratory Press (1994) (hereinafter referred to as "*Manipulating the Mouse Embryo, A Laboratory Manual*"; *Gene Targeting, A Practical Approach,* IRL Press at Oxford University Press (1993); *Biomanual Series* 8, *Gene Targeting, Preparation of Mutant Mice Using ES Cells,* Yodosha (1995) (hereinafter referred to as *Preparation of Mutant Mice Using ES Cells*); etc., for example, in the following manner.

A genomic DNA encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain is prepared.

Based on the nucleotide sequence of the genomic DNA, a target vector is prepared for homologous recombination of a target gene to be modified (e.g., the structural gene or promoter gene for the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain).

The host cell used for the production of the high ADCC activity antibody-producing cell can be prepared by introducing the prepared target vector into a host cell and selecting a cell in which homologous recombination occurred between the target gene on the chromosome and the target vector.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1.

The genomic DNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be prepared by the methods for preparing a genomic DNA described in the above 1 (1) (a).

Examples of the nucleotide sequences of the genomic DNAs encoding the enzyme relating to the synthesis of the intracellular sugar nucleotide, GDP-fucose obtained by the above methods include the nucleotide sequences represented by SEQ ID NOs:26, 27, 28 and 29.

An example of the nucleotide sequence of the genomic DNA encoding the enzyme relating to the modification of a sugar chain in which 1-position of fucose is bound to 6-position of N-acetylglucosamine in the reducing terminal through α-bond in a complex type N-glycoside-linked sugar chain obtained by the above methods is the nucleotide sequence represented by SEQ ID NO:30.

The target vector for use in the homologous recombination of the target gene on the chromosome can be prepared according to the methods described in *Gene Targeting, A Practical Approach*, IRL Press at Oxford University Press (1993); *Biomanual Series* 8, *Gene Targeting, Preparation of Mutant Mice Using ES Cells*, Yodosha (1995); etc. The target vector may be either a replacement-type or an insertion-type.

Introduction of the target vector into various host cells can be carried out by the methods suitable for introducing a recombinant vector into various host cells described in the above 1.

The methods for efficiently selecting a homologous recombinant include positive selection, promoter selection, negative selection and polyA selection described in *Gene Targeting, A Practical Approach*, IRL Press at Oxford University Press (1993); *Biomanual Series* 8, *Gene Targeting, Preparation of Mutant Mice Using ES Cells*, Yodosha (1995); etc. The methods for selecting the desired homologous recombinant from the selected cell lines include Southern hybridization (*Molecular Cloning*, Second Edition) and PCR [*PCR Protocols*, Academic Press (1990)] with the genomic DNA.

(c) Preparation of the Host Cell for the High ADCC Activity Antibody-Producing Cell by the RDO Method The host cell used for the production of the high ADCC activity antibody-producing cell can be prepared by the RDO method targeting a gene encoding an enzyme relating to the synthesis of the intracellular sugar nucleotide, GDP-fucose or an enzyme relating to the modification of a sugar chain in which 1-position of fucose is bound to 6-position of N-acetyl-glucosamine in the reducing terminal through α-bond in a complex type N-glycoside-linked sugar chain, for example, in the following manner.

A cDNA or a genomic DNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain is prepared by the methods described in the above 1 (1) (a).

The nucleotide sequence of the prepared cDNA or genomic DNA is determined.

Based on the determined DNA sequence, an RDO construct of appropriate length which comprises a part encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, a part of its non-translated region or a part of introns is designed and synthesized.

The host cell of the present invention can be obtained by introducing the synthesized RDO into a host cell and then selecting a transformant in which a mutation occurred in the target enzyme, that is, the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1.

Introduction of the RDO into various host cells can be carried out by the methods suitable for introducing a recombinant vector into various host cells described in the above 1.

The cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain can be prepared by the methods for preparing a cDNA described in the above 2 (1) (a) or the like.

The genomic DNA encoding the enzyme relating to the synthesis of an intracellular sugar nucleotide, GDP-fucose or the enzyme relating to the modification of a sugar chain in which 1-position of fucose is bound to 6-position of N-acetyl-glucosamine in the reducing terminal through α-bond in a complex type N-glycoside-linked sugar chain can be prepared by the methods for preparing a genomic DNA described in the above 2 (1) (b) or the like.

After DNA is cleaved with appropriate restriction enzymes, the nucleotide sequence of the DNA can be determined by subcloning the DNA fragments into a plasmid such as pBluescript™ SK(−) (manufactured by Stratagene), subjecting the clones to the reaction generally used as a method for analyzing a nucleotide sequence such as the dideoxy method of Sanger et al. [*Proc. Natl. Acad. Sci., USA*, 74, 5463 (1977)] or the like, and then analyzing the clones by using an automatic nucleotide sequence analyzer such as ABI PRISM 377 DNA Sequencer™ (manufactured by Applied Biosystems) or the like.

The RDO can be prepared by conventional methods or by using a DNA synthesizer.

The methods for selecting a cell in which a mutation occurred by introducing the RDO into the host cell, in the gene encoding the enzyme, that is, the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain include the methods for directly detecting mutations in chromosomal genes described in *Molecular Cloning*, Second Edition, *Current Protocols in Molecular Biology*, and the like.

For the selection of the transformant, the following methods can also be employed: the method using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain described in the above 2 (1) (a); the method using, as an index, the sugar chain structure of a glycoprotein on the cell membrane described in 2 (5) below; and the method using, as an index, the sugar chain structure of a produced antibody molecule described in 4 or 5 below.

The RDO can be designed according to the descriptions in *Science*, 273, 1386 (1996); *Nature Medicine*, 4, 285 (1998); *Hepatology*, 25, 1462 (1997); *Gene Therapy*, 5, 1960 (1999); *Gene Therapy*, 5, 1960 (1999); *J. Mol. Med.*, 75, 829 (1997); *Proc. Natl. Acad. Sci. USA*, 96, 8774 (1999); *Proc. Natl. Acad. Sci. USA*, 96, 8768 (1999); *Nuc. Acids Res.*, 27, 1323 (1999); *Invest. Dermatol.*, 111, 1172 (1998); *Nature Biotech.*, 16, 1343 (1998); *Nature Biotech.*, 18, 43 (2000); *Nature Biotech.*, 18, 555 (2000); and the like.

(d) Preparation of the Host Cell for the Production of the High ADCC Activity Antibody-Producing Cell by the RNAi Method The host cell used for the production of the high ADCC activity antibody-producing cell can be prepared by the RNAi method targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain, for example, in the following manner.

A cDNA encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain is prepared by the methods described in the above 2 (1) (a).

The nucleotide sequence of the prepared cDNA is determined.

Based on the determined cDNA sequence, an RNAi gene of appropriate length is designed which comprises a part encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, or a part of non-translated regions.

In order to express the RNAi gene in a cell, a recombinant vector is prepared by inserting a fragment or full-length of the prepared cDNA into a site downstream of a promoter in an appropriate expression vector.

The recombinant vector is introduced into a host cell suited for the expression vector to obtain a transformant.

The host cell used for the preparation of the host cell can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, or the sugar chain structure of a produced antibody molecule or a glycoprotein on the cell membrane.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the designed RNAi gene. Examples of the expression vectors include those described in the above 1.

Introduction of a gene into various host cells can be carried out by the methods suitable for introducing a recombinant vector into various host cells described in the above 1.

The methods for selecting the transformant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex type N-glycoside-linked sugar chain include the methods described in the above 2 (1) (a).

The methods for selecting the transformant using, as an index, the sugar chain structure of a glycoprotein on the cell membrane include the method described in 2 (5). The methods for selecting the transformant using, as an index, the sugar chain structure of a produced antibody molecule include the methods described in 4 or 5 below.

The methods for preparing cDNA encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain include the methods for preparing a cDNA described in the above 2 (1) (a), and the like.

The host cell used for the production of the high CDC activity and high ADCC activity antibody-producing cell of the present invention can also be obtained, without using an expression vector, by directly introducing into a host cell the RNAi gene designed based on the nucleotide sequence encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain.

The RNAi gene can be prepared by known methods or by using a DNA synthesizer.

The RNAi gene construct can be designed according to the descriptions in *Nature*, 391, 806 (1998); *Proc. Natl. Acad. Sci. USA*, 95, 15502 (1998); *Nature*, 395, 854 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); and the like.

(e) Preparation of the Host Cell for the Production of the High ADCC Activity Antibody-Producing Cell by the Method Using a Transposon The host cell used for the production of the high ADCC activity antibody-producing cell can be prepared by using the transposon system described in *Nature Genet.*, 25, 35 (2000), and the like, and then selecting a mutant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex type N-glycoside-linked sugar chain, or the sugar chain structure of a produced antibody molecule or a glycoprotein on the cell membrane.

The transposon system is a system for inducing a mutation by random insertion of an exogenous gene into the chromosome, wherein usually an exogenous gene inserted into a transposon is used as a vector for inducing a mutation and a transposase expression vector for randomly inserting the gene into the chromosome is introduced into the cell at the same time.

Any transposase can be used so long as it is suitable for the sequence of the transposon to be used.

As the exogenous gene, any gene can be used so long as it can induce a mutation in the DNA of a host cell.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1. Introduction of the gene into various host cells can be carried out by the methods suitable for introducing a recombinant vector into various host cells described in the above 1.

The methods for selecting the mutant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain include the methods described in the above 2 (1) (a).

The methods for selecting the mutant using, as an index, the sugar chain structure of a glycoprotein on the cell membrane include the method described in 2 (5). The methods for selecting the mutant using, as an index, the sugar chain structure of a produced antibody molecule include the methods described in 4 or 5 below.

(2) Technique of Introducing a Dominant-Negative Mutant of a Gene Encoding an Enzyme The host cell used for the production of the high ADCC activity antibody-producing cell can be prepared by using the technique of introducing a dominant-negative mutant of a target gene, i.e., a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain. Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing terminal through α-bond in a complex type N-glycoside-linked sugar chain include a1,6-fucosyltransferase and α-L-fucosidase.

These enzymes have substrate specificity and catalyze specific reactions. By disrupting the active center of such enzymes having substrate specificity and catalytic activity, their dominant-negative mutants can be prepared. Preparation of a dominant-negative mutant is described in detail below, using GMD as an example among the target enzymes.

As a result of the analysis of the three-dimensional structure of GMD derived from *Escherichia coli*, it has been revealed that four amino acids (threonine at position 133, glutamic acid at position 135, tyrosine at position 157 and lysine at position 161) have an important function for the enzyme activity (*Structure*, 8, 2, 2000). That is, the mutants prepared by substituting the above four amino acids by other amino acids based on the three-dimensional structure information all showed significantly decreased enzyme activity. On the other hand, little change was observed in the ability of the mutants to bind to the GMD coenzyme NADP or the substrate GDP-mannose. Accordingly, a dominant-negative mutant can be prepared by substituting the four amino acids which are responsible for the enzyme activity of GMD. On the basis of the result of preparation of a dominant-negative mutant of GMD derived from *Escherichia coli*, dominant-negative mutants can be prepared by performing homology comparison and three-dimensional structure prediction using the amino acid sequence information. For example, in the case of GMD derived from CHO cell (SEQ ID NO:19), a dominant-negative mutant can be prepared by substituting threonine at position 155, glutamic acid at position 157, tyrosine at position 179 and lysine at position 183 bp other amino acids. Preparation of such a gene carrying introduced amino acid substitutions can be carried out by site-directed mutagenesis described in *Molecular Cloning*, Second Edition, *Current Protocols in Molecular Biology*, and the like.

The host cell used for the production of the high ADCC activity antibody-producing cell can be prepared according to the method of gene introduction described in *Molecular Cloning*, Second Edition, *Current Protocols in Molecular Biology, Manipulating the Mouse Embryo*, Second Edition, and the like using a gene encoding a dominant-negative mutant of a target enzyme (hereinafter abbreviated as dominant-negative mutant gene) prepared as above, for example, in the following manner.

A dominant-negative mutant gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain is prepared.

Based on the full-length DNA of the prepared dominant-negative mutant gene, a DNA fragment of appropriate length containing a region encoding the protein is prepared according to need.

A recombinant vector is prepared by inserting the DNA fragment or full-length DNA into a site downstream of a promoter in an appropriate expression vector.

The recombinant vector is introduced into a host cell suited for the expression vector to obtain a transformant.

The host cell used for the preparation of the high ADCC activity antibody-producing cell can be obtained by selecting a transformant using, as an index, the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain, or the sugar chain structure of a produced antibody molecule or a glycoprotein on the cell membrane.

As the host cell, any yeast, animal cell, insect cell, plant cell, or the like can be used so long as it has a gene encoding the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain. Examples of the host cells include those described in the above 1.

The expression vectors that can be employed are those capable of autonomous replication or integration into the chromosome in the above host cells and comprising a promoter at a position appropriate for the transcription of the DNA encoding the desired dominant-negative mutant. Examples of the expression vectors include those described in the above 1.

Introduction of a gene into various host cells can be carried out by the methods suitable for introducing a recombinant vector into various host cells described in the above 1.

The methods for selecting the transformant using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex type N-glycoside-linked sugar chain include the methods described in 2 (1) (a) below.

The methods for selecting the transformant using, as an index, the sugar chain structure of a glycoprotein on the cell membrane include the method described in 2 (5) below. The methods for selecting the transformant using, as an index, the sugar chain structure of a produced antibody molecule include the methods described in 4 or 5 below.

(3) Technique of Introducing a Mutation into an Enzyme

The host cell used for the high ADCC activity antibody-producing cell can be prepared by introducing a mutation into a gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain, and then selecting a desired cell line in which the mutation occurred in the enzyme.

Examples of the enzymes relating to the synthesis of the intracellular sugar nucleotide, GDP-fucose include GMD, Fx, and the like. Examples of the enzymes relating to the modification of a sugar chain in which 1-position of fucose is bound to 6-position of N-acetylglucosamine in the reducing terminal through α-bond in a complex type N-glycoside-linked sugar chain include α1,6-fucosyltransferase, α-L-fucosidase, and the like.

The methods for introducing a mutation into the enzyme include: 1) a method in which a desired cell line is selected from mutants obtained by subjecting a parent cell line to mutagenesis or by spontaneous mutation using, as an index, the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex type N-glycoside-linked sugar chain; 2) a method in which a desired cell line is selected from mutants obtained by subjecting a parent cell line to mutagenesis or by spontaneous mutation using, as an index, the sugar chain structure of a produced antibody molecule; and 3) a method in which a desired cell line is selected from mutants obtained by subjecting a parent cell line to mutagenesis or by spontaneous mutation using, as an index, the sugar chain structure of a glycoprotein on the cell membrane.

Mutagenesis may be carried out by any method capable of inducing a point mutation, a deletion mutation or a frameshift mutation in DNA of a cell of a parent cell line.

Suitable methods include treatment with ethyl nitrosourea, nitrosoguanidine, benzopyrene or an acridine dye and irradiation. Various alkylating agents and carcinogens are also useful as mutagens. A mutagen is allowed to act on a cell by the methods described in *Soshiki Baiyo no Gijutsu* (*Tissue Culture Techniques*), Third Edition (Asakura Shoten), edited by The Japanese Tissue Culture Association (1996); *Nature Genet.*, 24, 314 (2000); and the like.

Examples of the mutants generated by spontaneous mutation include spontaneous mutants obtained by continuing subculture under usual cell culture conditions without any particular treatment for mutagenesis.

The methods for measuring the activity of the enzyme relating to the synthesis of an intracellular sugar nucleotide, GDP-fucose or the enzyme relating to the modification of a sugar chain in which 1-position of fucose is bound to 6-position of N-acetylglucosamine in the reducing terminal through α-bond in a complex type N-glycoside-linked sugar chain include the methods described in the above 1 (1) (a). The methods for determining the sugar chain structure of a produced antibody molecule include the methods described in 4 or 5 below. The methods for determining the sugar chain structure of a glycoprotein on the cell membrane include the method described in the above 2 (5).

(4) Technique of Suppressing Transcription or Translation of a Gene Encoding an Enzyme The host cell used for the production of the high ADCC activity antibody-producing cell can be prepared by suppressing transcription or translation of a target gene, i.e., a target gene encoding an enzyme relating to the synthesis of the intracellular sugar nucleotide, GDP-fucose or an enzyme relating to the modification of a sugar chain in which 1-position of fucose is bound to 6-position of N-acetylglucosamine in the reducing terminal through α-bond in a complex type N-glycoside-linked sugar chain using the antisense RNA/DNA technique [*Bioscience and Industry*, 50, 322 (1992); *Chemistry*, 46, 681 (1991); *Biotechnology*, 9, 358 (1992); *Trends in Biotechnology*, 10, 87 (1992); *Trends in Biotechnology*, 10, 152 (1992); *Cell Technology*, 16, 1463 (1997)], the triple helix technique [*Trends in Biotechnology*, 10, 132 (1992)], and the like.

Examples of the enzymes relating to the synthesis of the intracellular sugar nucleotide, GDP-fucose include GMD, Fx, and the like. Examples of the enzymes relating to the modification of a sugar chain in which 1-position of fucose is bound to 6-position of N-acetylglucosamine in the reducing terminal through α-bond in a complex type N-glycoside-linked sugar chain include α1,6-fucosyltransferase, α-L-fucosidase, and the like.

The methods for measuring the activity of the enzyme relating to the synthesis of an intracellular sugar nucleotide, GDP-fucose or the activity of the enzyme relating to the modification of a sugar chain in which 1-position of fucose is bound to 6-position of N-acetylglucosamine in the reducing terminal through α-bond in a complex type N-glycoside-linked sugar chain include the methods described in the above 2 (1) (a).

The methods for determining the sugar chain structure of a glycoprotein on the cell membrane include the method described in the above 2 (5). The methods for determining the sugar chain structure of a produced antibody molecule include the methods described in 4 or 5 below.

(5) Technique of Selecting a Cell Line Resistant to a Lectin which Recognizes a Sugar Chain Structure in which 1-Position of Fucose is Bound to 6-Position of N-Acetylglucosamine in the Reducing Terminal Through α-Bond in a N-Glycoside-Linked Sugar Chain The host cell used for the production of the high ADCC activity antibody-producing cell can be prepared by selecting a cell line resistant to a lectin which recognizes a sugar chain structure in which 1-position of fucose is bound to 6-position of N-acetylglucosamine in the reducing terminal through α-bond in a N-glycoside-linked sugar chain.

Selection of a cell line resistant to a lectin which recognizes a sugar chain structure in which 1-position of fucose is bound to 6-position of N-acetylglucosamine in the reducing terminal through α-bond in a N-glycoside-linked sugar chain can be carried out, for example, by the method using a lectin described in *Somatic Cell Mol. Genet.*, 12, 51 (1986), and the like.

As the lectin, any lectin can be used so long as it recognizes a sugar chain structure in which 1-position of fucose is bound to 6-position of N-acetylglucosamine in the reducing terminal through α-bond in a N-glycoside-linked sugar chain. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

Specifically, the cell line resistant to a lectin which recognizes a sugar chain structure in which 1-position of fucose is bound to 6-position of N-acetylglucosamine in the reducing terminal through α-bond in a N-glycoside-linked sugar chain can be selected by culturing cells in a medium containing the above lectin at a concentration of 1 µg/ml to 1 mg/ml for one day to 2 weeks, preferably one day to one week, subculturing surviving cells or picking up a colony and transferring it into a culture vessel, and subsequently continuing the culturing using the medium containing the lectin.

3. Evaluation of the Activity of the Antibody Composition

The protein amount, antigen-binding activity or cytotoxic activity of the purified antibody composition can be measured using the known methods described in *Monoclonal Antibodies, Antibody Engineering*, or the like.

Specifically, when the antibody composition is a human chimeric antibody or a humanized antibody, the binding activity to an antigen or the binding activity to cultured cell line which is antigen-positive can be measured by ELISA, the fluorescent antibody technique [*Cancer Immunol. Immunother.*, 36, 373 (1993)], and the like. The cytotoxic activity to cultured cell line which is antigen-positive can be evaluated by measuring CDC activity, ADCC activity, or the like [*Cancer Immunol. Immunother.*, 36, 373 (1993)].

The method for measuring ADCC activity includes a method in which a target cell labeled with a radioisotope, a fluorescent substance, a dye or the like is allowed to contact with an antibody and an effector cell, and then the activity of the labeled substance released from the injured target cell is measured; a method in which a target cell is allowed to contact with an antibody and an effector cell, and then the biological activity of an enzyme released from the injured target cell is measured; and the like.

The method for measuring CDC activity includes a method in which a target cell labeled with a radioisotope, a fluorescent substance, a dye or the like is allowed to contact with an antibody and a biological specimen such as serum containing a complement component, and then the activity of the labeled substance released from the injured target cell is measured; a method in which a target cell is allowed to contact with an antibody and a biological specimen such as serum containing a complement component, and then the biological activity of an enzyme released from the injured target cell is measured; and the like.

The safety and therapeutic effect of the antibody composition in human can be evaluated using an appropriate animal model of a species relatively close to human, e.g., cynomolgus monkey.

4. Analysis of Sugar Chains in the Antibody Composition

The sugar chain structure of the antibody molecule expressed in various cells can be analyzed according to general methods of analyzing the sugar chain structure of glycoprotein. For example, a sugar chain bound to an IgG molecule consists of neutral sugars such as galactose, mannose and fucose, amino sugars such as N-acetylglucosamine, and acidic sugars such as sialic acid, and can be analyzed by techniques such as sugar composition analysis and sugar chain structure analysis using two-dimensional sugar chain mapping.

(1) Analysis of Neutral Sugar and Amino Sugar Compositions

The sugar chain composition of an antibody composition can be analyzed by carrying out acid hydrolysis of sugar chains with trifluoroacetic acid or the like to release neutral sugars or amino sugars and analyzing the composition ratio.

Specifically, the analysis can be carried out by a method using a carbohydrate analysis device manufactured by Dionex. BioLC is a device for analyzing the sugar composition by HPAEC-PAD (high performance anion-exchange chromatography-pulsed amperometric detection) [*J. Liq. Chromatogr.*, 6, 1577 (1983)].

The composition ratio can also be analyzed by the fluorescence labeling method using 2-aminopyridine. Specifically, the composition ratio can be calculated by fluorescence labeling an acid-hydrolyzed sample by 2-aminopyridylation according to a known method [*Agric. Biol. Chem.*, 55(1), 283-284 (1991)] and then analyzing the composition by HPLC.

(2) Analysis of Sugar Chain Structure

The sugar chain structure of an antibody composition can be analyzed by two-dimensional sugar chain mapping [*Anal. Biochem.*, 171, 73 (1988); *Seibutsukagaku Jikkenho (Biochemical Experimentation Methods) 23—Totanpakushitsu Tosa Kenkyuho (Methods of Studies on Glycoprotein Sugar Chains)*, Gakkai Shuppan Center, edited by Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, respectively, and comparing them with the results of known sugar chains.

Specifically, a sugar chain is released from an antibody by hydrazinolysis of the antibody and subjected to fluorescence labeling with 2-aminopyridine (hereinafter referred to as PA) [*J. Biochem.*, 95, 197 (1984)]. After being separated from an excess PA-treating reagent by gel filtration, the sugar chain is subjected to reversed phase chromatography. Then, each peak of the fractionated sugar chain is subjected to normal phase chromatography. The sugar chain structure can be deduced by plotting the obtained results on a two-dimensional sugar chain map and comparing them with the spots of a sugar chain standard (manufactured by Takara Shuzo Co., Ltd.) or those in the literature [*Anal. Biochem.*, 171, 73 (1988)].

The structure deduced by the two-dimensional sugar chain mapping can be confirmed by carrying out mass spectrometry, e.g., MALDI-TOF-MS, of each sugar chain.

5. Method for Determining the Sugar Chain Structure of an Antibody Molecule

An antibody composition comprises an antibody molecule having different sugar chain structures binding to the Fc region of antibody. Among the antibody compositions of the present invention, the antibody composition, in which the ratio of sugar chains in which fucose is not bound to the N-acetylglucosamine in the reducing terminal to the total complex type N-glycoside-linked sugar chains bound to the Fc region is 20% or more, shows high ADCC activity. Such an antibody composition can be determined using the method for analyzing the sugar chain structure of an antibody molecule described in the above 4. Further, it can also be determined by immunoassays using lectins.

Determination of the sugar chain structure of an antibody molecule by immunoassays using lectins can be made according to the immunoassays such as Western staining, RIA (radioimmunoassay), VIA (viroimmunoassay), EIA (enzymeimmunoassay), FIA (fluoroimmunoassay) and MIA (metalloimmunoassay) described in the literature [*Monoclonal Antibodies: Principles and Applications*, Wiley-Liss, Inc. (1995); *Enzyme Immunoassay*, 3rd Ed., Igaku Shoin (1987); *Enzyme Antibody Technique*, Revised Edition, Gakusai Kikaku (1985); and the like], for example, in the following manner.

A lectin recognizing the sugar chain structure of an antibody molecule constituting an antibody composition is labeled, and the labeled lectin is subjected to reaction with a sample antibody composition, followed by measurement of the amount of a complex of the labeled lectin with the antibody molecule.

Examples of lectins useful for determining the sugar chain structure of an antibody molecule include WGA (wheat-germ agglutinin derived from *T. vulgaris*), ConA (concanavalin A derived from *C. ensiformis*), RIC (toxin derived from *R. communis*), L-PHA (leukoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (Elderberry balk lectin), ECL (*Erythrina cristagalli* lectin), EEL (*Euonymus europaeus* lectin), GNL (*Galanthus nivalis* lectin), GSL (*Griffonia simplicifolia* lectin), HPA (*Helix pomatia* agglutinin), HHL (*Hippeastrum* hybrid lectin), Jacalin, LTL (*Lotus tetragonolobus* lectin), LEL (*Lycopersicon esculentum* lectin), MAL (*Maackia amurensis* lectin), MPL (*Madura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin).

It is preferred to use lectins specifically recognizing a sugar chain structure wherein fucose is bound to the N-acetylglucosamine in the reducing terminal in complex type N-glycoside-linked sugar chains. Examples of such lectins include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

6. Utilization of the Recombinant Antibody Composition of the Present Invention

Since the recombinant antibody composition of the present invention has higher CDC activity than an IgG1 antibody and an IgG3 antibody, it has more excellent property in therapeutic effects than conventional antibody compositions. Also, among the antibody compositions of the present invention, since the recombinant antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more has higher CDC activity and higher ADCC activity than an IgG1 antibody and an IgG3 antibody, it has more excellent property in therapeutic effects than conventional antibody compositions. Furthermore, among the recombinant antibody compositions of the present invention, the recombinant antibody composition comprising an antibody molecule having complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 100% is more preferred.

A medicament comprising the recombinant antibody composition of the present invention may be administered alone as a therapeutic agent. However, it is preferably mixed with one or more pharmaceutically acceptable carriers and provided as a pharmaceutical preparation produced by an arbitrary method well known in the technical field of pharmaceutics.

It is desirable to administer the medicament by the route that is most effective for the treatment. Suitable administration routes include oral administration and parenteral administration such as intraoral administration, intratracheal administration, intrarectal administration, subcutaneous administration, intramuscular administration and intravenous administration. In the case of an antibody preparation, intravenous administration is preferable.

The medicament may be in the form of spray, capsules, tablets, granules, syrup, emulsion, suppository, injection, ointment, tape, and the like.

The preparations suitable for oral administration include emulsions, syrups, capsules, tablets, powders and granules.

Liquid preparations such as emulsions and syrups can be prepared using, as additives, water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

Capsules, tablets, powders, granules, and the like can be prepared using, as additives, excipients (e.g., lactose, glucose, sucrose and mannitol), disintegrating agents (e.g., starch and sodium alginate), lubricants (e.g., magnesium stearate and talc), binders (e.g., polyvinyl alcohol, hydroxypropyl cellulose and gelatin), surfactants (e.g., fatty acid esters), plasticizers (e.g., glycerin), and the like.

The pharmaceutical preparations suitable for parenteral administration include injections, suppositories and sprays.

Injections can be prepared using carriers comprising a salt solution, a glucose solution, or a mixture thereof, etc. It is also possible to prepare powder injections by freeze-drying the antibody composition according to a conventional method and adding sodium chloride thereto.

Suppositories can be prepared using carriers such as cacao butter, hydrogenated fat and carboxylic acid.

The antibody composition may be administered as such in the form of spray, or sprays may be prepared using carriers which do not stimulate the oral or airway mucous membrane of a recipient and which can disperse the antibody composition as fine particles to facilitate absorption thereof.

Suitable carriers include lactose and glycerin. It is also possible to prepare aerosols, dry powders, and the like according to the properties of the antibody composition and the carriers used. In preparing these parenteral preparations, the above-mentioned additives for the oral preparations may also be added.

The dose and administration frequency will vary depending on the desired therapeutic effect, the administration route, the period of treatment, the patient's age, body weight, and the like. However, an appropriate dose of the active ingredient for an adult person is generally 10 µg/kg to 20 mg/kg per day.

The anti-tumor effect of the antibody composition against various tumor cells can be examined by in vitro tests such as CDC activity measurement and ADCC activity measurement and in vivo tests such as anti-tumor experiments using tumor systems in experimental animals (e.g., mice).

The CDC activity and ADCC activity measurements and anti-tumor experiments can be carried out according to the methods described in the literature [*Cancer Immunology Immunotherapy*, 36, 373 (1993); *Cancer Research*, 54, 1511 (1994); and the like].

The present invention is described below based on Examples; however, the present invention is not limited thereto.

Example 1

Preparation of Anti-CD20 Human IgG1 Chimeric Antibody, Anti-CD20 Human IgG3 Chimeric Antibody and Anti-CD20 Domain-Swapped Antibody Using Animal Cells 1. Production of Anti-CD20 Human IgG3 Chimeric Antibody Expression Vector cDNA was synthesized from human lymph node-derived poly A+ RNA (manufactured by BD Biosciences Clontech) using cDNA Synthesis Kit (manufactured by Amersham Pharmacia Biotech) in accordance with the instructions attached thereto. PCR was carried out using 100 ng of cDNA as the template, and using KOD plus (manufactured by TOYOBO) and human IgG constant region-specific synthetic DNA primers (manufactured by FASMAC) comprising the amino acid sequences represented by SEQ ID NOs:1 and 2 in accordance with the attached instructions of KOD plus. PCR was carried out using GeneAmp™ PCR System 9700 (manufactured by Applied Biosystems) after thermal denaturation at 94° C. for 1 minute, followed by 30 cycles consisting of reactions at 94° C. for 15 seconds, at 62° C. for 30 seconds and at 68° C. for 90 seconds. After further carrying out reaction at 68° C. for 7 minutes, 2.5 U of Taq DNA polymerase (manufactured by Takara Shuzo) was added thereto and allowed to react at 68° C. for 7 minutes in order to add adenine to the 3'-terminal. The reaction solution was subjected to electrophoresis using 1% agarose gel, and an amplified fragment of about 1.1 kbp considered to be a gene of the heavy chain constant region of IgG3 was recovered by using QIAquick™ Gel Extraction Kit (manufactured by Qiagen). A ligation reaction with a plasmid pCRII-TOPO vector (manufactured by Invitrogen) was carried out by adding Ligation High solution (manufactured by TOYOBO), and *Escherichia coli* DH5α (manufactured by TOYOBO) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700™ DNA Analyzer of the same company to confirm that this sequence is a nucleotide sequence encoding the same amino acid sequence of the heavy chain constant region of a conventionally known human IgG3 (GenBank accession No. AAH33178).

Figure 3:
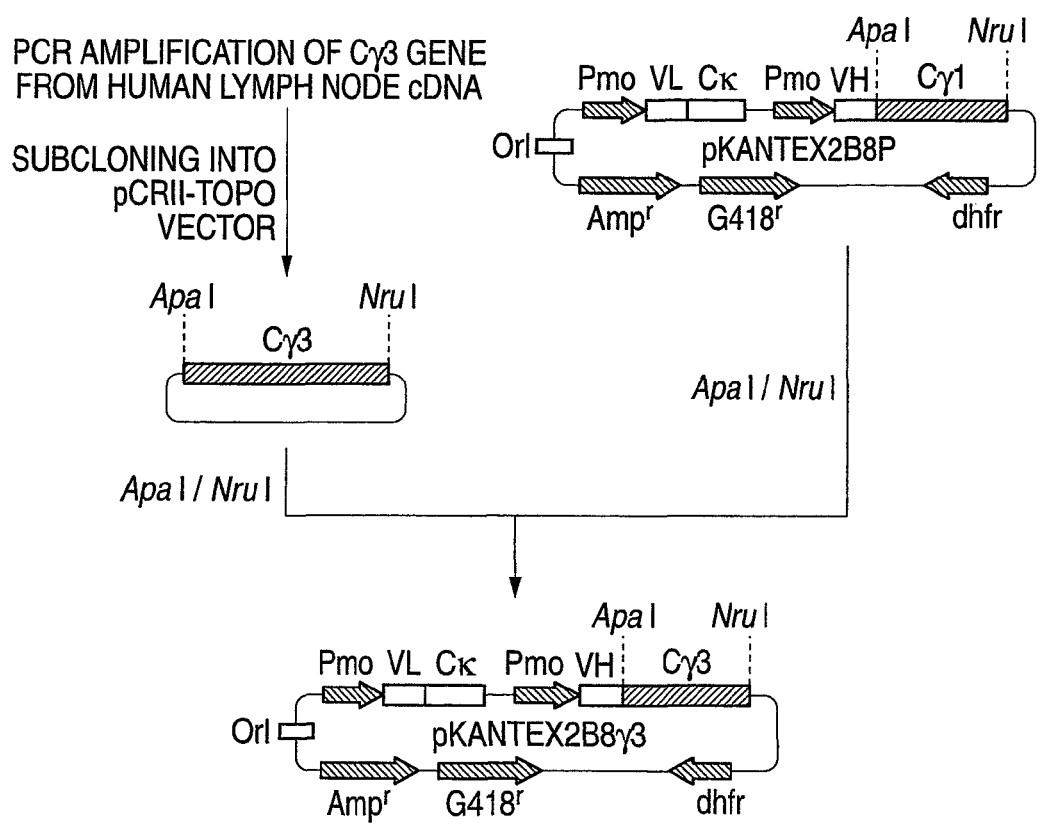
FIG. 3 shows construction steps of a plasmid pKANTEX2B8γ3.

A gene fragment of 1.13 kbp in the heavy chain constant region of IgG3 was purified from the above-described plasmid into which the gene of the heavy chain constant region of human IgG3 was inserted, by treatment with restriction enzymes ApaI and NruI (both manufactured by Takara Shuzo). Stable animal cell expression vector for anti-CD20 human IgG1 chimeric antibody (described in WO03/055993A1), pKANTEX2B8P, which comprises a variable region of an anti-CD20 human IgG1 chimeric antibody Rituxan™, human κ type light chain constant region and human IgG1 heavy chain constant region, was digested with ApaI and NruI. Expression vector for anti-CD20 human IgG3 chimeric antibody, pKANTEX2B8γ3 (FIG. 3) was constructed by cleaving the IgG1 constant region gene, purifying the remaining fragment of about 12.6 kbp and ligating it with the above-described IgG3 constant region gene fragment using the Ligation High solution. The amino acid sequences of the variable region and the light chain constant region of the anti-CD20 human IgG3 chimeric antibody encoded by pKANTEX2B8γ3 were identical to the amino acid sequences of the variable region and the light chain constant region of the anti-CD20 human IgG1 chimeric antibody encoded by pKANTEX2B8P.

2. Production of Anti-CD20 Domain-Swapped Antibody Expression Vector

A domain-swapped antibody which binds to CD20, wherein the amino acid sequences of the variable region and the light chain constant region are identical to the amino acid sequences of the variable region and the light chain constant region of the anti-CD20 human IgG1 chimeric antibody encoded by pKANTEX2B8P and the heavy chain constant region is constituted by the domain of a human IgG1 antibody or human IgG3 antibody, was prepared in accordance with the following procedure. The anti-CD20 chimeric antibody having a heavy chain constant region in which the CH1 and hinge are constituted by amino acid sequences from a human IgG1 antibody, and the Fc regions (CH2 and CH3) are constituted by amino acid sequences from a human IgG3 antibody, is called 1133-type anti-CD20 domain-swapped antibody, and the anti-CD20 chimeric antibody having a heavy chain constant region wherein the CH1 and hinge are constituted by amino acid sequences from a human IgG3 antibody, and the Fc regions are constituted by amino acid sequences from a human IgG1 antibody, is called 3311-type anti-CD20 domain-swapped antibody. As a result of search using amino acid sequence database, it was found that the amino acid sequences of heavy chain constant regions of these domain-swapped antibodies are novel amino acid sequences.

Figure 4:
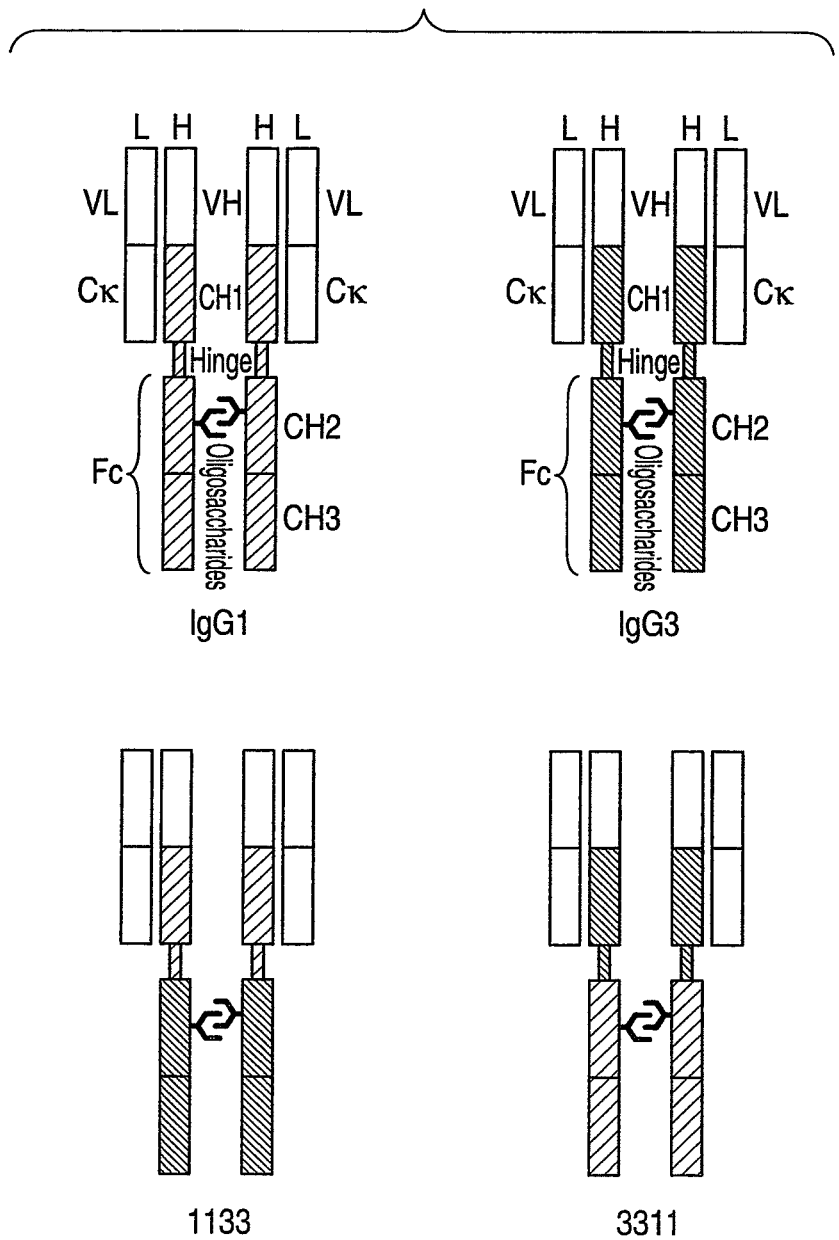
FIG. 4 is a schematic illustration showing an anti-CD20 domain-swapped antibody.

Subclasses from which each domain of the various designed anti-CD20 domain-swapped antibodies was derived, and corresponding amino acid sequences of heavy chain constant regions are shown in Table 1. Schematic illustration of each anti-CD20 domain-swapped antibody is shown in FIG. 4.

TABLE 1

| Structural name | CH1 | Hinge | CH2 | CH3 | Fc Amino acid sequence |
|---|---|---|---|---|---|
| 1133 | IgG1 | IgG1 | IgG3 | IgG3 | SEQ ID NO: 16 |
| 3311 | IgG3 | IgG3 | IgG1 | IgG1 | SEQ ID NO: 4 |

Figure 5:
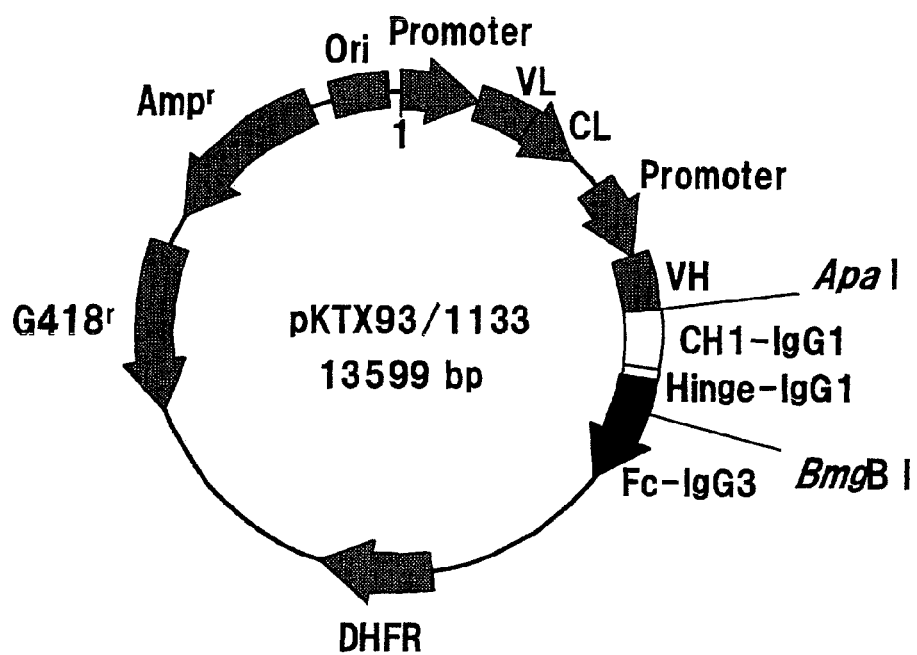
FIG. 5 shows a plasmid pKTX93/1133.

(1) Construction of Expression Vector Encoding the 1133-Type Anti-CD20 Domain-Swapped Antibody The expression vector encoding the 1133-type anti-CD20 domain-swapped antibody, shown in FIG. 5, was constructed in the following manner.

A DNA fragment of about 430 bp encoding CH1 domain, hinge domain and a part of the 5'-terminal side of Fc region (a part in which the amino acid sequence was identical between human IgG1 antibody and human IgG3 antibody) of the human IgG1 antibody was cleaved and purified from the expression vector for anti-CD20 human IgG1 chimeric antibody, pKANTEX2B8P using restriction enzymes ApaI (manufactured by Takara Shuzo) and BmgBI (manufactured by New England Biolabs). On the other hand, a DNA fragment of about 13 kbp was cleaved and purified from the expression vector for anti-CD20 human IgG3 chimeric antibody, pKANTEX2B8γ3 described in the item 1 of this Example by the similar treatment with restriction enzymes. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700™ DNA Analyzer of the same company to confirm that the plasmid pKTX93/1133 shown in FIG. 5 was obtained.

Figure 6:
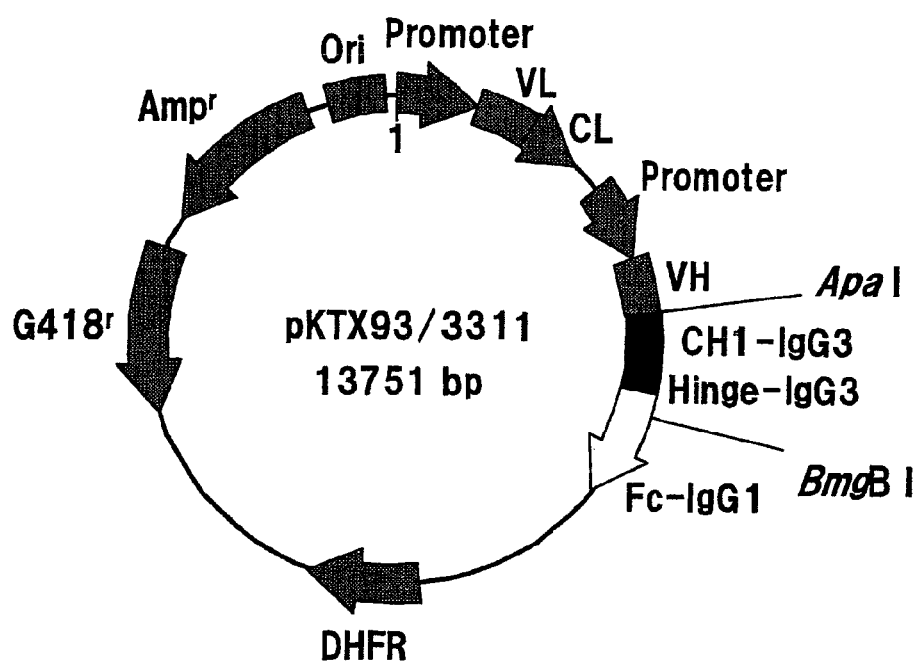
FIG. 6 shows a plasmid pKTX93/3311.

(2) Construction of Expression Vector Encoding the 3311-Type Anti-CD20 Domain-Swapped Antibody The expression vector encoding the 3311-type anti-CD20 domain-swapped antibody, shown in FIG. 6, was constructed in the following manner.

A DNA fragment of about 570 bp encoding CH1 domain, hinge domain and a part of the 5'-terminal side of Fc region (a part in which the amino acid sequence was identical between human IgG1 antibody and human IgG3 antibody) of the human IgG3 antibody was cleaved and purified from the human IgG3 chimeric antibody expression vector, pKANTEX2B8γ3 described in the item 1 of this Example using restriction enzymes ApaI (manufactured by Takara Shuzo) and BmgBI (manufactured by New England Biolabs). On the other hand, a DNA fragment of about 13 kbp was cleaved and purified from the expression vector for IgG1 anti-CD20 antibody, pKANTEX2B8P by the similar treatment with restriction enzymes. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into the plasmid was analyzed by a DNA sequencer ABI PRISM 3700™ DNA Analyzer of the same company to confirm that the plasmid pKTX93/3311 shown in FIG. 6 was obtained.

3. Stable Expression of Various Anti-CD20 Chimeric Antibodies and Various Anti-CD20 Domain-Swapped Antibodies in Animal Cells Cells for stably producing an anti-CD20 human IgG3 chimeric antibody or anti-CD20 domain-swapped antibody, in which the expression vector for anti-CD20 human IgG3 chimeric antibody, pKANTEX2B8γ3 and expression vectors for anti-CD20 domain-swapped antibody, pKTX93/1133 and pKTX93/3311 prepared in the items 1 and 2 of this Example, were introduced into a CHO/DG44 cell [*Somatic Cell Mol. Genet.*, 12, 555 (1986)] and the CHO/DG44 cell in which α1,6-fucosyltransferase gene was knocked out (hereinafter referred to as CHO/FUT8$^{-/-}$) [*Biotechnol. Bioeng.*, 87, 614 (2004)] as host cells were prepared in the following manner. The CHO/DG44 cell is a host cell widely used in the production of recombinant protein. The CHO/FUT8$^{-/-}$ is a host cell in which FUT8 of the CHO/DG44 cell is knocked out on the genome. In addition, the expression vector pKANTEX2B8P for anti-CD20 human IgG1 chimeric antibody was introduced into the CHO/FUT8$^{-/-}$ cell alone, and a cell capable of stably producing an anti-CD20 human IgG1 chimeric antibody was prepared in the same manner.

After introducing 8 μg of each expression vector plasmid into 1.6×10$^6$ cells of the CHO/DG44 cell or CHO/FUT8$^{-/-}$ cell by the electroporation method [*Cytotechnology*, 3, 133 (1990)], the cells were suspended in 40 ml of IMDM-(10) [IMDM medium (manufactured by GIBCO-BRL) containing 10% of dialyzed fetal bovine serum (dFBS)] and dispensed at 100 μl/well into a 96-well microplate (manufactured by Sumitomo Bakelite). After culturing at 37° C. for 24 hours in a 5% CO$_2$ incubator, the cells were cultured for 1 to 2 weeks in the IMDM-(10) containing G418 at concentration of 500 μg/ml. After the culturing, culture supernatant was recovered from each well, and the amount of the anti-CD20 domain-swapped antibody in the culture supernatant was measured by the ELISA which is described later in the item 4 of this Example. Regarding the transformants of wells in which expression of the anti-CD20 domain-swapped antibody was found in the culture supernatants, in order to increase the antibody expression amount using the dhfr gene amplification system, the cells were suspended in the IMDM-(10) medium containing G418 at concentration of 500 μg/ml and methotrexate at concentration of 50 nM (hereinafter referred to as MTX: manufactured by SIGMA) as an inhibitor of dihydrofolate reductase which was the dhfr gene product and cultured at 37° C. for about 1 week in a 5% CO$_2$ incubator to thereby obtain transformants having resistance to 50 nM of MTX. Subsequently, the MTX concentration was successively raised to 100 nM and then to 200 nM to finally obtain transformants which can proliferate in the IMDM-(10) medium containing G418 at concentration of 500 μg/ml and 200 nM MTX and also can express the antibodies encoded by the respective expression vectors at high level.

4. Measurement of Antibody Concentration in Culture Supernatant (ELISA)

Goat anti-human IgG (H & L) antibody (manufactured by American Qualex) was diluted to 1 µg/ml with phosphate buffered saline (hereinafter referred to as PBS; manufactured by Proliant Inc), dispensed at 50 µl/well into a 96-well plate for ELISA (manufactured by Greiner) and allowed to stand at room temperature for 1 hour for adsorption. After the reaction, the plate was washed with PBS, and 1% bovine serum albumin (hereinafter referred to as BSA)-containing PBS (hereinafter referred to as 1% BSA-PBS) was added thereto at 100 µl/well and allowed to react at room temperature for 1 hour to block the remaining active groups. After removing 1% BSA-PBS, culture supernatants to be measured were added at 50 µl/well and allowed to react at room temperature for 2 hours. After the reaction, each well was washed with 0.05% Tween 20-containing PBS (hereinafter referred to as Tween-PBS), and then a peroxidase-labeled goat anti-human IgG (Fc) antibody solution (manufactured by American Qualex) diluted 500-fold with PBS was added at 50 µl/well as the secondary antibody solution and allowed to react at room temperature for 1 hour. After washing with Tween-PBS, ABTS substrate solution [a solution prepared by dissolving 0.55 g of ammonium 2,2'-azino-bis(3-ethylbenzothiazoline-6-sulfonate) in 1 liter of 0.1 M citrate buffer (pH 4.2) and adding 1 µl/ml of hydrogen peroxide just before the use] was added at 50 µl/well for color development, and the absorbance at 415 nm (hereinafter referred to as OD415) was measured.

5. Purification of Various Anti-CD20 Chimeric Antibodies and Various Anti-CD20 Domain-Swapped Antibodies Each of the transformants capable of expressing various anti-CD20 antibodies obtained in the item 3 of this Example was suspended in IMDM-FCS(10) containing 200 nM of MTX to a density of $1 \times 10^5$ cells/ml, and then dispensed at 100 ml into triple flasks (manufactured by Nalgenunc) and cultured at 37° C. for 2 days in a 5% $CO_2$ incubator. Culture supernatant was removed from each flask, the inside of the flask was washed with 50 ml of PBS, and then 100 ml of EXCELL 301 medium (manufactured by JRH Biosciences) was added to the flask to continue the culturing at 37° C. for 5 days in the 5% $CO_2$ incubator. This culture supernatant was recovered, centrifuged at 3000 rpm and 4° C. for 5 minutes, and then the supernatant was recovered and subjected to filtration sterilization using a 0.22 µm PES Membrane (manufactured by Iwaki). The various anti-CD20 antibodies were purified from the thus sterilized culture supernatants using a column packed with Prosep-A™ (Protein-A: manufactured by Millipore) or Prosep-G™ (Protein-G: manufactured by Millipore) in accordance with the instructions attached thereto. The IgG1 anti-CD20 antibody was purified by protein A, but since the IgG3 anti-CD20 antibody was not purified by protein A, purification was carried out by using protein G. Regarding the domain-swapped antibodies, the 3311-type was purified by protein A. On the other hand, the 1133-type was purified with protein A, but could be purified by protein G.

The expression vector and host cell of each antibody, names of the purified antibody samples and corresponding heavy chain constant region of amino acid sequences are shown in Table 2. In this connection, in the table, the sample having (+F) at the end of the sample name indicates an antibody sample produced using CHO/DG44 as the host cell, and other samples indicate antibody samples produced from CHO/FUT8$^{-/-}$.

TABLE 2

| Expression vector | Host cell | Purified antibody (name) |
|---|---|---|
| pKANTEX2B8 | CHO/FUT8$^{-/-}$ | CD20-IgG1(−F) |
| pKANTEX2B8g3 | CHO/DG44 | CD20-IgG3(+F) |
| pKANTEX2B8g3 | CHO/FUT8$^{-/-}$ | CD20-IgG3(−F) |
| pKTX93/1133 | CHO/DG44 | 1133(+F) |
| pKTX93/1133 | CHO/FUT8$^{-/-}$ | 1133(−F) |
| pKTX93/3311 | CHO/DG44 | 3311(+F) |
| pKTX93/3311 | CHO/FUT8$^{-/-}$ | 3311(−F) |

In the table, +F indicates that fucose is bound to a sugar chain which binds to the Fc region, and −F indicates that fucose is not bound to a sugar chain which binds to the Fc region.

6. Evaluation of the Purification Degree of Various Anti-CD20 Chimeric Antibody Samples and Various Anti-CD20 Domain-Swapped Antibody Samples Purified by SDS-PAGE In order to evaluate the purification degree of the purified samples of various anti-CD20 antibodies obtained in the item 5 of this Example, SDS-polyacrylamide gel electrophoresis (hereinafter referred to as SDS-PAGE) was carried out in accordance with a conventionally known method [*Nature*, 227, 680 (1970)], using about 1 µg of each of the purified samples of various anti-CD20 antibodies. As a comparative control of the electrophoresis degree, the same operation was also carried out for an anti-CD20 human IgG1 chimeric antibody Rituxan™ (purchased from Genentech). Hereinafter, Rituxan™ is referred to as CD20-IgG1(+F).

As a result, 1133(+F) and 1133(−F) showed an electrophoresis pattern similar to that of the human IgG1 antibody CD20-IgG1(+F), and 3311(+F) and 3311(−F) showed an electrophoresis pattern similar to that of the human IgG3 antibody CD20-IgG3(+F). In the case of CD20-IgG1(+F), CD20-IgG1(−F), 1133(+F) and 1133(−F), the band of the H chain was found at about 50 kilodaltons (hereinafter referred to as kDa), and that of the L chain was found at about 24 kDa, and in the case of CD20-IgG3(+F), CD20-IgG3(−F), 3311(+F) and 3311(−F), the band of the H chain was found at about 54 kDa, and that of the L chain was found at about 24 kDa, so that it was confirmed that each of the prepared anti-CD20 antibodies is constituted by the desired H chain and L chain.

Based on the above results, it was confirmed that the various desired IgG molecules constituted by H chain and L chain are contained at a sufficient ratio in the purified samples of respective anti-CD20 antibodies obtained in the item 5 of this Example.

Example 2

Activity Evaluation of Various Anti-CD20 Chimeric Antibodies and Various Anti-CD20 Domain-Swapped Antibodies Comparison of various activities was carried out for the purified samples of various anti-CD20 antibodies obtained in the item 5 of Example 1 in the following manner.

1. Binding Activity of Various Anti-CD20 Antibodies to CD20-Positive Cell

Binding activity of the various anti-CD20 antibodies obtained in Example 1 to CD20-positive cells was measured in a competitive inhibition system with biotinylated Rituxan™, by fluorescent antibody technique using a flow cytometer. As negative controls, an anti-Her2 human IgG1 antibody Herceptin™ [*Proc. Natl. Acad. Sci. U.S.A.*, 89, 4285 (1992)] (purchased from Genentech) and an anti-CCR4 human IgG1 antibody KM3060 [*Cancer Res.*, 64, 2127 (2004)] were used.

A CD20-positive Burkitt lymphoma-derived cell line Daudi cell (ATCC: CCL-213) was dispensed at $5 \times 10^5$ cells per well into a 96-well U-plate (manufactured by Falcon), and then a buffer for FACS [0.2 mg/ml human IgG (manufactured by Sigma), 0.02% EDTA, 0.05% $NaN_3$, 1% BSA] containing 10 μg/ml or 1 μg/ml of the respective CD20 antibodies obtained in the item 5 of Example 1, or the negative controls anti-Her2 antibody Herceptin™ [*Proc. Nall. Acad. Sci. U.S.A.*, 89, 4285 (1992)] and anti-CCR4 antibody KM3060 (WO02/31140), and containing 0.5 μg/ml of biotin-labeled anti-CD20 chimeric antibody Rituxan™ [prepared by biotinylating Rituxan™ using EZ-Link™ Sulfo-NHS-LC-Biotin (manufactured by Pierce)], was added thereto at 50 μl/well. After reaction at 4° C. for 60 minutes under shade, the cells were washed twice with the buffer for FACS, and then the PE-labeled streptoavidin diluted 200-fold with the buffer for FACS was added thereto at 50 μl/well. After reaction at 4° C. for 60 minutes under shade, the cells were washed twice with the buffer for FACS and suspended in 1 ml of the buffer for FACS, and then the fluorescence intensity was measured with a flow cytometer EPICS-XL™ (manufactured by Coulter).

Figure 7:
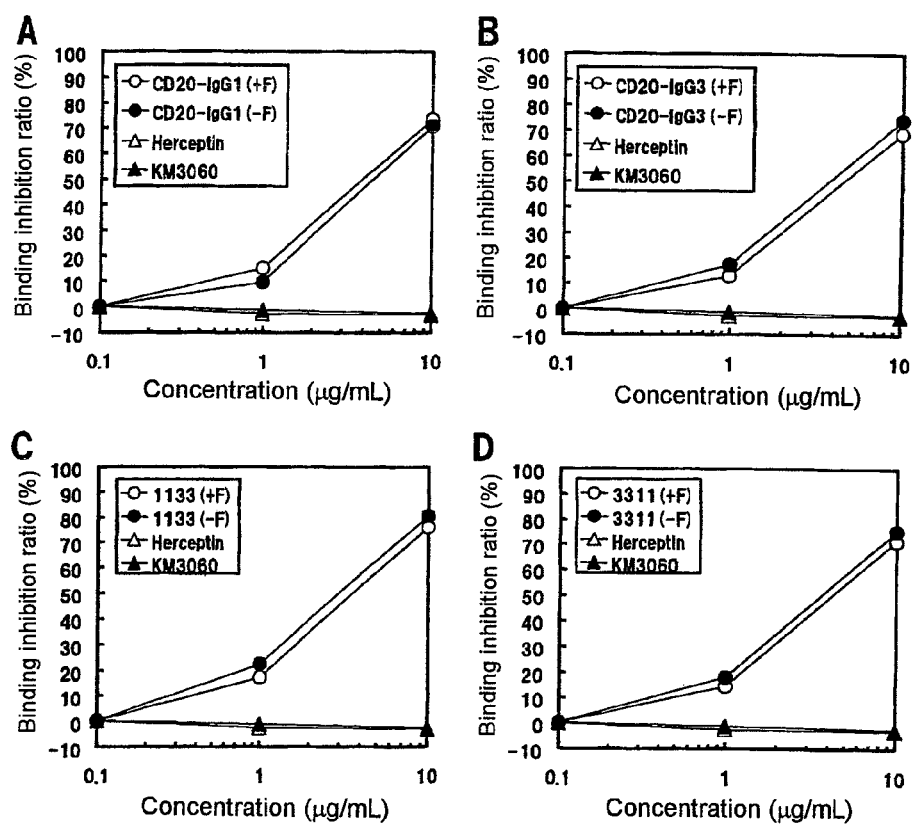
FIG. 7 shows binding activity of various CD20 domain-swapped antibodies, an anti-CD20 human IgG1 chimeric antibody and an anti-CD20 human IgG3 chimeric antibody with an anti-CD20 antibody CD20-IgG1(+F) in a competitive inhibition assay to Daudi cell. The abscissa shows sample concentration, and the ordinate shows binding inhibition ratio at each sample concentration. Δ and ▲ in the graphs are common to graphs A to D and show a negative control anti-Her2 antibody Herceptin™ (Δ) and an anti-CCR4 antibody KM3060 (▲). Regarding ○ and ● in the graphs, the corresponding sample is different in each graph, and graph A shows CD20-IgG1(+F) (○) and CD20-IgG1(−F) (●), graph B shows CD20-IgG3(+F) (○) and CD20-IgG3(−F) (●), graph C shows 1133(+F) (○) and 1133(−F) (●), and graph D shows 3311(+F) (○) and 3311(−F) (●).

The results are shown in FIG. 7. The negative controls anti-Her2 antibody Herceptin™ and anti-CCR4 antibody KM3060 did not inhibit binding of the biotin-labeled anti-CD20 chimeric antibody Rituxan™ to the CD20-positive cell Daudi, but all of the anti-CD20 domain-swapped antibodies, anti-CD20 human IgG1 chimeric antibodies and anti-CD20 human IgG3 chimeric antibodies concentration dependently inhibited the binding and the degree was almost the same. Based on these results, it was shown that antigen-binding of the anti-CD20 domain-swapped antibodies is CD20-specific and that the binding activity of the anti-CD20 domain-swapped antibodies is similar to that of the anti-CD20 human IgG1 chimeric antibody.

2. Measurement of CDC Activity of Various Anti-CD20 Antibodies to Daudi Cell

In vitro CDC activity of the purified samples of various anti-CD20 antibodies obtained in the item 5 of Example 1 was measured using a CD20-positive Daudi cell.

The reaction was carried out in a 96-well flat-bottomed plate (manufactured by Sumitomo Bakelite), and a human complement dilution medium [prepared by diluting a human complement (manufactured by SIGMA) 6-fold with RPMI 1640 medium (manufactured by GIBCO BRL) containing 10% FBS (manufactured by JRH)] containing $5 \times 10^4$ cells of the Daudi cell and containing 0.3 μg/ml of each anti-CD20 domain-swapped antibody, anti-CD20 human IgG1 chimeric antibody or anti-CD20 human IgG3 chimeric antibody was dispensed at 150 μl into respective reaction wells. In addition, a reaction well containing no anti-CD20 domain-swapped antibody (0% reaction well) was prepared as a control in case CDC was not induced, and a reaction well containing no Daudi cell (100% reaction well) as a control in case CDC was induced. After culturing at 37° C. for 2 hours in an atmosphere of 5% $CO_2$, WST-1 reagent (manufactured by ROCHE) was added at 15 μl into respective reaction wells and allowed to react at 37° C. for 4 hours in an atmosphere of 5% $CO_2$. After completion of the reaction, OD450 in each well was measured, and the CDC activity (%) was calculated from the absorbance of each well using the following formula:

CDC activity (%)=100×{1−(reaction well absorbance−100% reaction well absorbance)/(0% reaction well absorbance−100% reaction well absorbance)}

Figure 8:
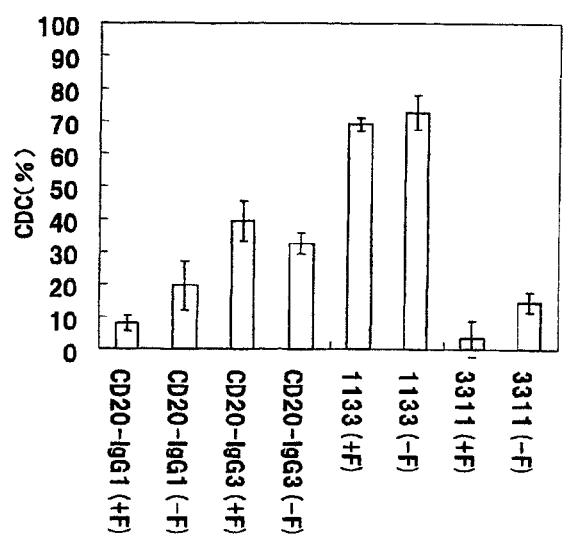
FIG. 8 shows CDC activity of anti-CD20 human IgG1 chimeric antibodies, anti-CD20 human IgG3 chimeric antibodies and anti-CD20 domain-swapped antibodies 1133 and 3311 to Daudi cell. The abscissa shows sample names, and the ordinate shows CDC activity. The graph shows CDC activity of each sample at a concentration of 0.3 μg/ml.

The results are shown in FIG. 8. As shown in FIG. 8, the CDC activity of anti-CD20 human IgG3 chimeric antibodies CD20-IgG3(+F) and CD20-IgG3(−F) was higher than that of anti-CD20 human IgG1 chimeric antibodies CD20-IgG1(+F) and CD20-IgG1(−F), so that it was confirmed that the CDC activity of IgG3 is higher than that of IgG1. However, 1133 (+F)-type and 1133(−F)-type anti-CD20 domain-swapped antibodies showed considerably higher CDC activity than the CDC activity of anti-CD20 human IgG3 chimeric antibodies. On the other hand, the CDC activity of anti-CD20 domain-swapped antibodies 3311(+F) and 3311(−F) was low. Also, in all of the anti-CD20 antibodies, the antibody samples produced using CHO/DG44 as the host cell and the antibody samples produced using CHO/FUT8$^{-/-}$ as the host cell showed almost the same CDC activity, and the activity of 1133-type was increased regardless of the fucose content of the sugar chain binding to the antibody. In addition, tendency of the amount of CDC activity of the above-described various antibodies did not change when the antibody concentration was increased to 1 μg/ml.

3. CDC Activity Measurement of 1133-Type Anti-CD20 Domain-Swapped Antibodies

In order to further fully evaluate CDC activity of the 1133 (+F)-type and 1133(−F)-type anti-CD20 domain-swapped antibodies which showed particularly high CDC activity in the item 2 of this Example, measurement of CDC activity was carried out in the same manner as in the item 2 of this Example using a CD20-positive Burkitt lymphoma-derived cell line ST 486 cell (ATCC: CRL-1647) or Burkitt lymphoma-derived cell line Raji cell (ATCC: CCL-86).

The results are shown in FIG. 9. As shown in FIG. 9, in each of the ST 486 cell line (FIG. 9A) and Raji cell line (FIG. 9B), the CDC activity of anti-CD20 human IgG3 chimeric antibodies CD20-IgG3(+F) and CD20-IgG3(−F) was slightly higher than the CDC activity of anti-CD20 human IgG1 chimeric antibodies CD20-IgG1(+F) and CD20-IgG1(−F), and 1133(+F)-type and 1133(−F)-type anti-CD20 domain-swapped antibodies showed remarkable CDC activity exceeding them. In addition, in all of these anti-CD20 antibodies, the antibody samples produced by CHO/DG44 as the host cell and the antibody samples produced by CHO/FUT8$^{-/-}$ as the host cell showed almost the same CDC activity.

5. Evaluation of ADCC Activity of Various Anti-CD20 Antibodies to CD20-Positive Cell Line In vitro ADCC activity of the purified samples of various anti-CD20 antibodies obtained in the item 5 of Example 1 was measured in the following manner using a CD20-positive Daudi cell as the target cell. Cytotox 96™ Kit (manufactured by Promega) was used in the measurement.

(1) Preparation of Human Effector Cell Suspension

From a healthy volunteer, 50 ml of peripheral blood was collected and gently mixed with 0.2 ml of heparin sodium (manufactured by Takeda Pharmaceutical). A monocyte fraction was separated from this using Lymphoprep (manufactured by Daiichi Pure Chemicals) in accordance with the instructions attached thereto and then washed by centrifugation once with RPMI 1640 medium and once with 10% FBS-RPMI 1640 medium, and the cell was used as the effector cell.

(2) Measurement of ADCC Activity

The reaction was carried out in a 96-well flat-bottomed plate (manufactured by Falcon), and 10% FBS-RPMI 1640 medium containing $2 \times 10^5$ cells of the effector cell and $1 \times 10^4$ cells of the Daudi cell or ST 486 cell and containing each CD20 antibody at varied concentration was dispensed at 200 μl into each reaction well. In addition, a medium well without the effector cell, target cell and antibody, an effector well containing the effector cell alone, a target well containing the target cell alone, an NK well containing the effector cell and target cell without antibody, a 100% reaction well containing the target cell alone and to which 20 μl of the Lysis buffer attached to the kit was added 3 hours and 15 minutes after commencement of the reaction, and a 100% reaction control well without the effector cell, target cell and antibody and to which 20 μl of the Lysis buffer attached to the kit was added 3 hours and 15 minutes after commencement of the reactions, were respectively prepared as subjective wells necessary for calculating ADCC activity. After carrying out reaction at 37° C. for 4 hours under an atmosphere of 5% $CO_2$ in each reaction well, the reaction plate was centrifuged to recover 50 μl of supernatant from each well. The supernatants of wells were respectively transferred to the wells of a 96-well U-bottom plate (manufactured by Sumitomo Bakelite), and a coloring substrate solution (prepared by dissolving one ampoule of the substrate attached to the kit in 12 ml of the assay buffer attached to the kit) was added at 50 μl into each well. The coloring reaction was carried out at 37° C. for 30 minutes, the reaction termination solution attached to the kit was added at 50 μl to each well, and then OD450 was measured to calculate the ADCC activity (%) from the absorbance of each well using the following formula.

$$\text{ADCC activity (\%)} = 100 \times (S-E-T)/(\text{Max}-T)$$

Figure 10:
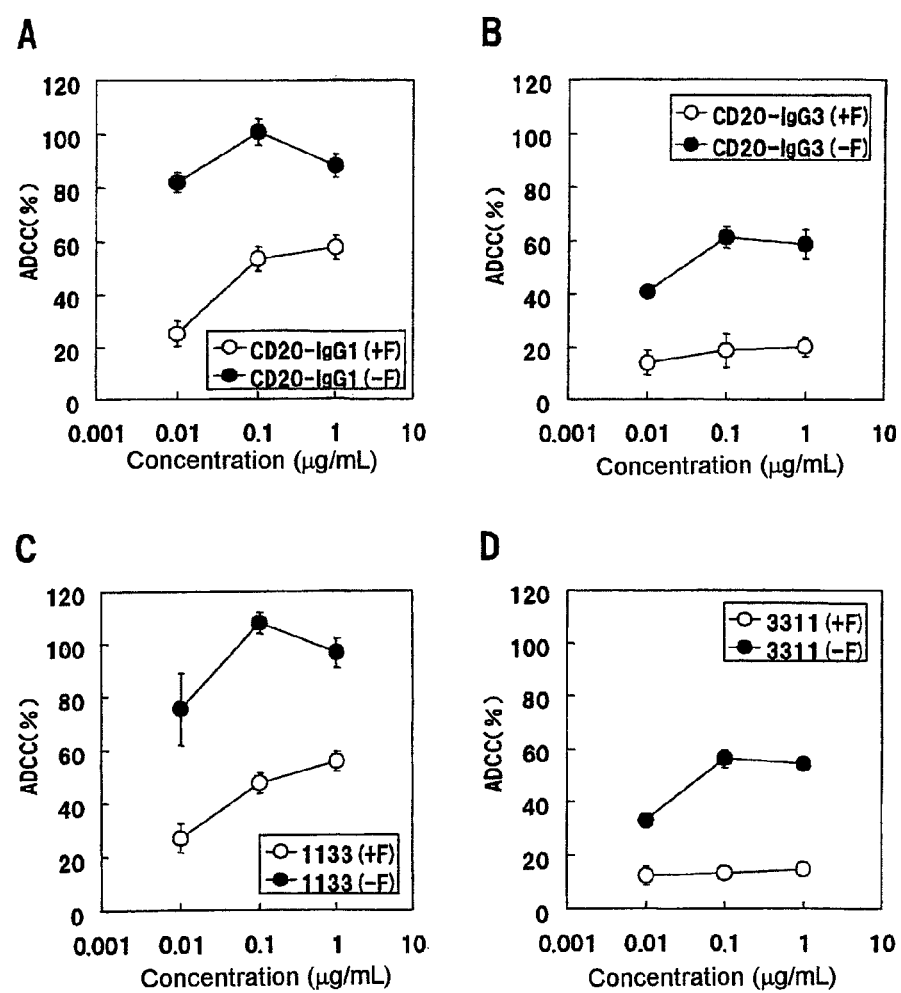
FIG. 10 shows ADCC activity of anti-CD20 human IgG1 chimeric antibodies, anti-CD20 human IgG3 chimeric antibodies, 1133-type anti-CD20 domain-swapped antibodies and 3311-type anti-CD20 domain-swapped antibodies to Daudi cell. The abscissa shows sample concentration, and the ordinate shows ADCC activity at each sample concentration. Regarding ○ and ● in the graphs, the corresponding sample is different in each graph, and graph A shows CD20-IgG1(+F) (○) and CD20-IgG1(−F) (●), graph B shows CD20-IgG3(+F) (○) and CD20-IgG3(−F) (●), graph C shows 1133(+F) (○) and 1133(−F) (●), and graph D shows 3311(+F) (○) and 3311(−F) (●).

S=sample reaction well absorbance−medium well absorbance
E=effector well absorbance−medium well absorbance
T=target well absorbance−medium well absorbance
Max=100% reaction well−100% reaction control well The results are shown in FIG. 10. As shown in FIG. 10, in all of the anti-CD20 antibodies, the antibody samples produced from CHO/FUT8$^{-/-}$ showed higher ADCC activity than the antibody samples produced from CHO/DG44. From this result, it was found that, also in the case of all of the anti-CD20 domain-swapped antibodies prepared in this Example, the ADCC activity is increased by the antibody composition in which fucose is not bound to the N-acetylglucosamine existing in the reducing terminal in the complex type N-glycoside-linked sugar chain bound to the Fc of the antibody, in comparison with the antibody composition in which fucose is bound to the N-acetylglucosamine existing in the reducing terminal of the complex type N-glycoside-linked sugar chain bound to the Fc of the antibody. Also, it was confirmed that the anti-CD20 human IgG1 chimeric antibodies show higher ADCC activity than that of the anti-CD20 human IgG3 chimeric antibodies, that is, ADCC activity of IgG is higher than that of IgG1. Also, the 1133-type anti-CD20 domain-swapped antibodies maintained high ADCC activity similar to the level of anti-CD20 human IgG1 chimeric antibodies. In addition, it was found that ADCC activity of the 3311-type anti-CD20 domain-swapped antibodies is low similarly to the case of anti-CD20 human IgG3 chimeric antibodies.

5. Measurement of the Binding Activity of Various Anti-CD20 Antibodies to Recombinant Fcγ Receptor IIIa (Hereinafter Referred to as FcγRIIIa)

In order to analyze the ADCC activity enhancing mechanism by anti-CD20 domain-swapped antibodies confirmed in the item 4 of this Example, the binding activity of anti-CD20 human IgG1 chimeric antibodies CD20-IgG1(−F) and CD20-IgG1(+F), anti-CD20 human IgG3 chimeric antibodies CD20-IgG3(−F) and CD20-IgG3(+F), and 1133-type anti-CD20 domain-swapped antibodies 1133(−F) and 1133(+F) to an Fc receptor family FcγRIIIa expressing on the surface of NK cell was measured in accordance with a conventionally known method [*Clin. Cancer Res.*, 10, 6248 (2004)].

Figure 11:
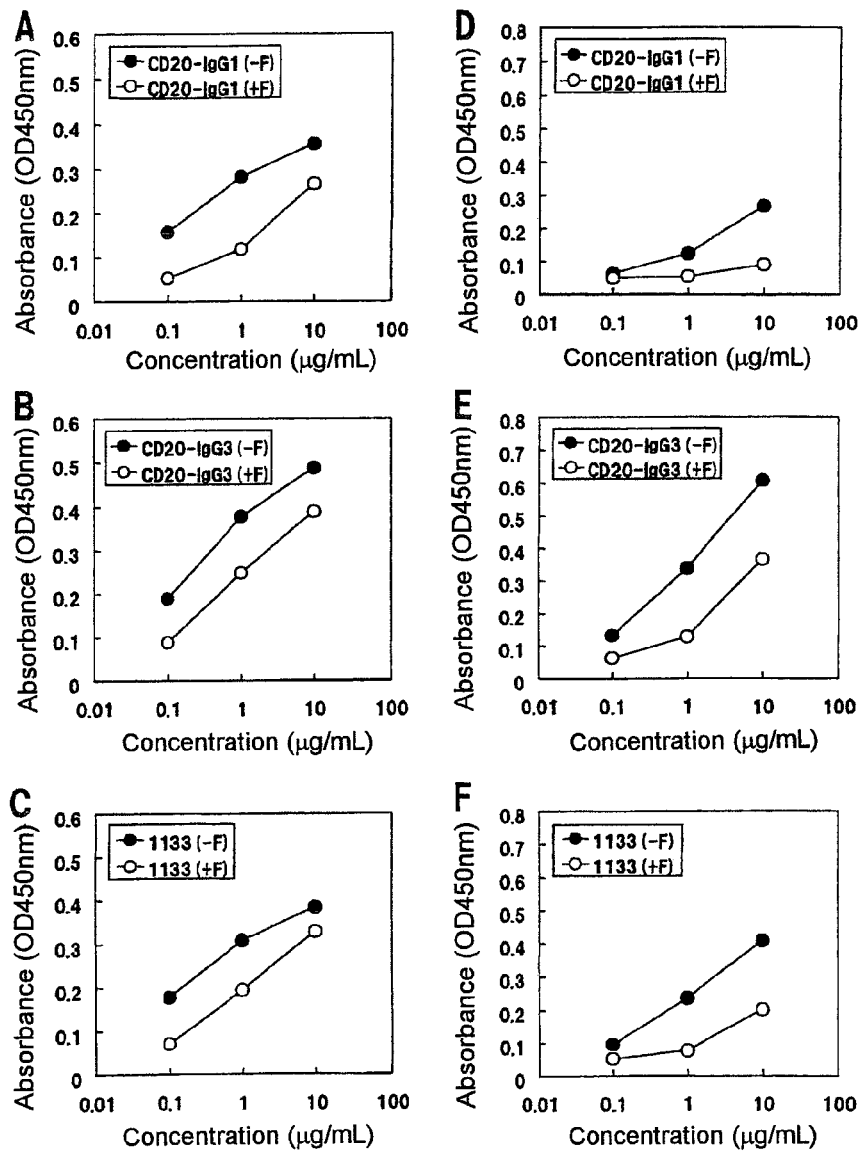
FIG. 11 shows binding activity of 1133-type anti-CD20 domain-swapped antibody, anti-CD20 human IgG1 chimeric antibody and anti-CD20 human IgG3 chimeric antibody to soluble human FcγRIIa (valine type) (A to C) or soluble human FcγRIIa (phenylalanine type) (D to F), in ELISA in the absence of the antigen CD20. The abscissa shows sample concentration, and the ordinate shows absorbance at each sample concentration. Graphs A and D show binding activity of CD20-IgG1(−F) (●) and CD20-IgG1(+F) (○), graphs B and E show that of CD20-IgG3(−F) (●) and CD20-IgG3(+F) (○), and graphs C and F show that of 1133(−F) (●) and 1133(+F) (○).

The results are shown in FIG. 11. As shown in FIG. 11, the antibody samples produced by CHO/FUT8$^{-/-}$ showed higher binding activity for FcγRIIIa than that of the antibody samples produced by CHO/DG44. Based on this result, it was confirmed that the increase of ADCC activity of antibody, due to the removal of the fucose binding to the N-acetylglucosamine existing in the reducing terminal of the complex type N-glycoside-linked sugar chain which is added to the Fc of 1133-type anti-CD20 domain-swapped antibodies, is caused by increasing the activity of the Fc region to the Fc receptor.

Based on the above, the 1133-type anti-CD20 domain-swapped antibodies having the same variable region as the anti-CD20 human IgG1 chimeric antibody Rituxan™, in which the CH1 domain and hinge domain of the H chain are the amino acid sequences of human IgG1 antibody and the Fc region is those of human IgG3 antibody, have CDC activity that exceeds anti-CD20 human IgG1 chimeric antibodies and anti-CD20 human IgG3 chimeric antibodies and also have ADCC activity substantially equivalent to that of the anti-CD20 human IgG1 chimeric antibodies. In addition, it was shown that the activity of binding Fc to Fc receptor is increased and the ADCC activity is improved similarly to the case of the anti-CD20 human IgG1 chimeric antibodies, by decreasing the content of fucose binding to the N-acetylglucosamine existing in the reducing terminal in the complex type N-glycoside-linked sugar chain bound to the Fc.

Relationship between structures and activities of each of the prepared respective antibody and domain-swapped antibodies is summarized in Table 3 based on the results obtained in the above. In the table, ADCC activity and CDC activity were expressed as ++++, +++, ++ and + in order of the grade of activities.

TABLE 3

| Purified antibody (name) | CH1 | Hinge | CH2 | CH3 | ADCC activity | CDC activity |
| --- | --- | --- | --- | --- | --- | --- |
| CD20-IgG1(+F)/ CD20-IgG1(−F) | IgG1 | IgG1 | IgG1 | IgG1 | ++/+++ | ++ |
| CD20-IgG3(+F)/ CD20-IgG3(−F) | IgG3 | IgG3 | IgG3 | IgG3 | +/++ | +++ |
| 1133(+F)/1133(−F) | IgG1 | IgG1 | IgG3 | IgG3 | ++/++ | ++++ |
| 3311(+F)/3311(−F) | IgG3 | IgG3 | IgG1 | IgG1 | +/+ | ++ |

Based on the above, it was shown that an antibody molecule having a heavy chain constant region in which the Fc region of the human IgG1 antibody was replaced by the Fc region of the human IgG3 antibody has CDC activity higher than that of the human IgG1 antibody and human IgG3 antibody and maintains high ADCC activity substantially equivalent to that of the human IgG1 antibody.

Example 3

Production of 1131-Type Anti-CD20 Domain-Swapped Antibody and 1113-Type Anti-CD20 Domain-Swapped Antibody Using Animal Cell 1. Production of Expression Vector for 1131-Type Anti-CD20 Domain-Swapped Antibody and Expression Vector for 1113-Type Anti-CD20 Domain-Swapped Antibody In Example 2, the 1133-type anti-CD20 domain-swapped antibody prepared by replacing the Fc region (CH2 and CH3) of the anti-CD20 human IgG1 chimeric antibody with the Fc region of the human IgG antibody showed CDC activity higher than that of anti-CD20 human IgG1 chimeric antibody. Next, in order to individually examine participation of the CH2 domain and CH3 domain which constitute the Fc region in the CDC activity, the following two anti-CD20 domain-swapped antibodies were prepared.

In the following Example, an anti-CD20 chimeric antibody having a heavy chain constant region in which the CH1, hinge and CH3 are constituted by the amino acid sequences from a human IgG1 antibody, and the CH2 is constituted by the amino acid sequences from a human IgG3 antibody, is called 1131-type anti-CD20 domain-swapped antibody, and an anti-CD20 chimeric antibody having a heavy chain constant region in which the CH1, hinge and CH2 are constituted by the amino acid sequences from a human IgG1 antibody, and the CH3 domain constituted by the amino acid sequences from a human IgG3 antibody, is called 1113-type anti-CD20 domain-swapped antibody. In each case, amino acid sequences of the variable region and light chain constant region are identical to the amino acid sequences of the variable region and light chain constant region of the anti-CD20 human IgG1 chimeric antibody encoded by pKANTEX2B8P.

Domain structures and amino acid sequences of the heavy chain constant regions of the 1131-type anti-CD20 domain-swapped antibody and 1113-type anti-CD20 domain-swapped antibody are shown in Table 4. Since no examples for preparing heavy chain constant regions of these anti-CD20 domain-swapped antibodies are unknown, both of them are novel structures. In addition, a schematic illustration of each domain-swapped antibody is shown in FIG. 12.

TABLE 4

| Structure name | CH1 | Hinge | CH2 | CH3 | Amino acid sequence |
|---|---|---|---|---|---|
| 1113-type | IgG1 | IgG1 | IgG1 | IgG3 | SEQ ID NO: 6 |
| 1131-type | IgG1 | IgG1 | IgG3 | IgG1 | SEQ ID NO: 31 |

(1) Construction of Expression Vector Comprising Nucleotide Sequence Encoding 1113-Type Anti-CD20 Domain-Swapped Antibody An expression vector encoding the 1113-type anti-CD20 chimeric antibody, wherein the amino acid sequences of the variable region and light chain constant region are identical to the amino acid sequences of the variable region and light chain constant region of the anti-CD20 human IgG1 chimeric antibody encoded by pKANTEX2B8P, and it has a heavy chain constant region wherein the CH1, hinge and CH2 are constituted by the amino acid sequences from a human IgG3 antibody, and the CH3 domain is constituted by the amino acid sequences from a human IgG1 antibody, was constructed in the following manner.

Figure 13:
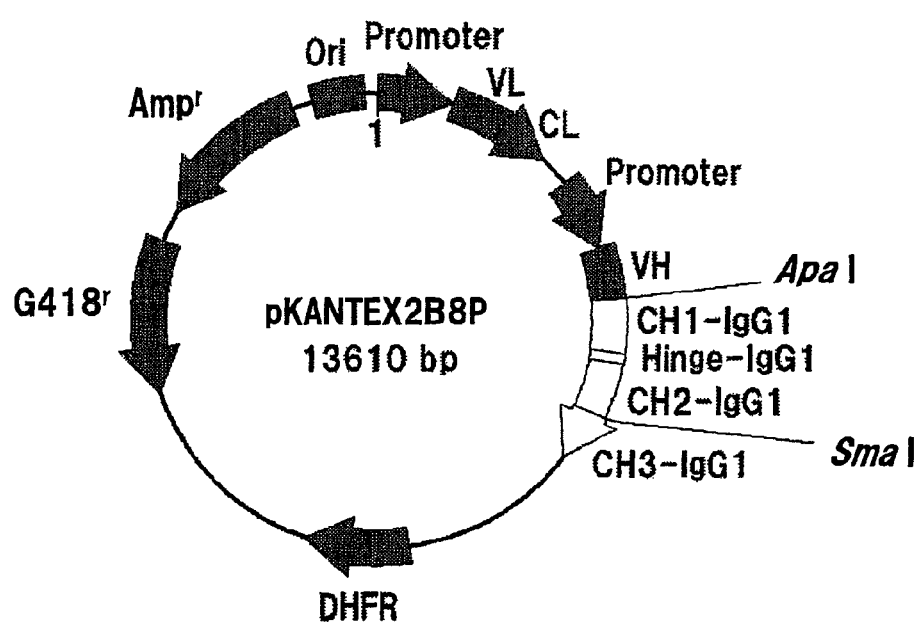
FIG. 13 shows a plasmid pKANTEX2B8P.

A DNA fragment of about 700 bp encoding the human IgG1 CH1 domain, hinge domain and CH2 domain was cleaved and purified from the expression vector for anti-CD20 human IgG1 chimeric antibody, pKANTEX2B8P shown in FIG. 13, using restriction enzymes ApaI (manufactured by Takara Shuzo) and SmaI (manufactured by Takara Shuzo). On the other hand, a DNA fragment of about 13 kbp was cleaved and purified by the same treatment with restriction enzymes on the expression vector for 1133-type anti-CD20 domain-swapped antibody, pKANTEX93/1133 described in the item 2(2) of Example 1 and shown in FIG. 14. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that the plasmid pKTX93/1113 shown in FIG. 15 was obtained.

(2) Construction of Expression Vector Comprising Nucleotide Sequence Encoding the Gene of 1131-Type Anti-CD20 Domain-Swapped Antibody 1131

Figure 16:
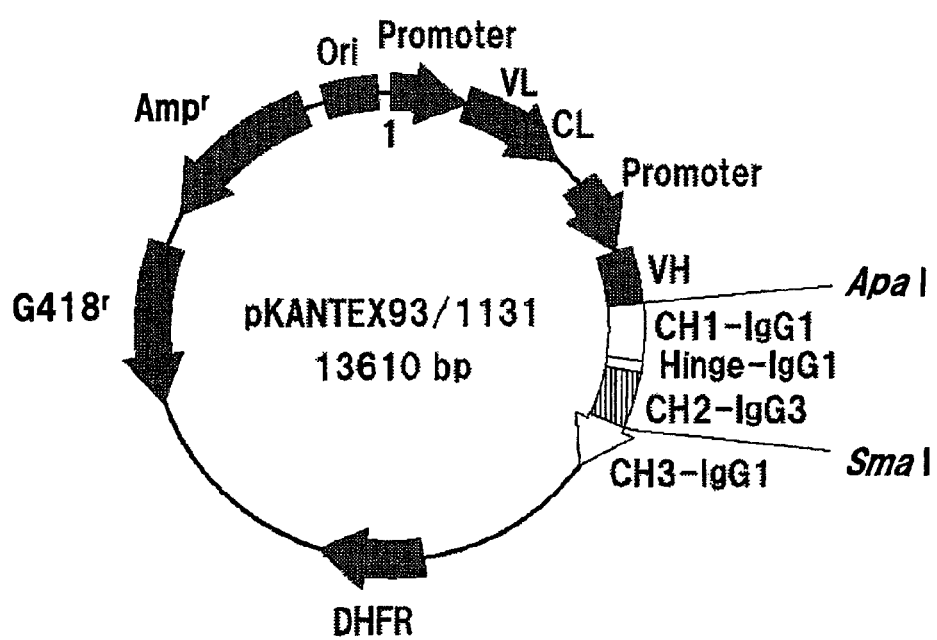
FIG. 16 shows a plasmid pKANTEX93/1131.

An expression vector encoding the 1113-type domain-swapped antibody shown in FIG. 16 which specifically reacts with human CD20, wherein the CH2 domain of CH is the amino acid sequence of human IgG3 and the CH1 domain, hinge domain and CH3 domain are the amino acid sequences of human IgG1, was constructed in the following manner.

Figure 14:
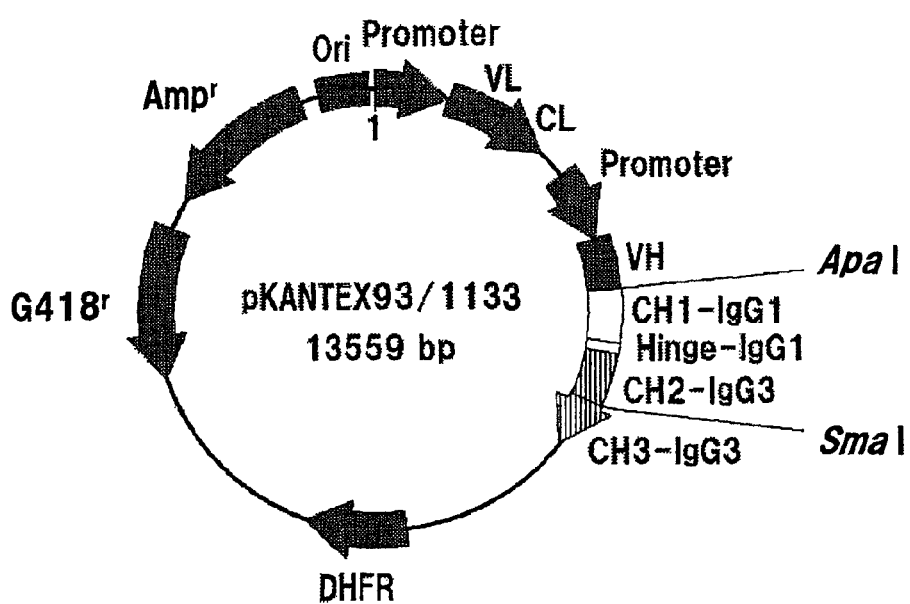
FIG. 14 shows positions of the restriction enzyme recognition sites ApaI and SmaI of a plasmid pKANTEX93/1133.
Figure 15:
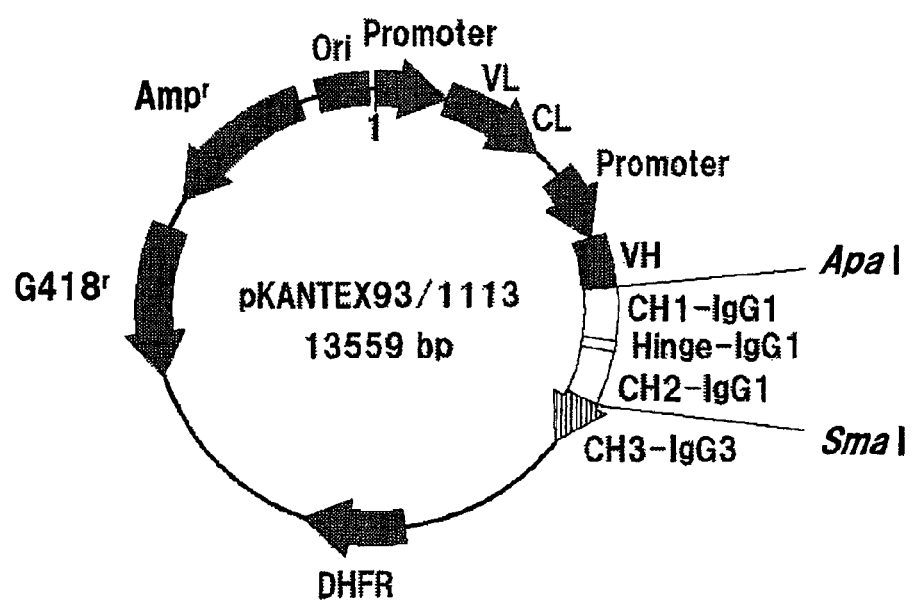
FIG. 15 shows a plasmid pKANTEX93/1113.

A DNA fragment of about 700 bp encoding the human IgG1 CH1 domain and hinge domain and the human IgG3 CH2 domain was cleaved and purified from the expression vector for 1133-type anti-CD20 domain-swapped antibody, pKANTEX93/1133 described in the item 2(2) of Example 1 and shown in FIG. 14, using restriction enzymes ApaI (manufactured by Takara Shuzo) and SmaI (manufactured by Takara Shuzo). On the other hand, a DNA fragment of about 13 kbp was cleaved and purified by carrying out the same restriction enzyme treatment on the expression vector for anti-CD20 human IgG1 chimeric antibody, pKANTEX2B8P shown in FIG. 13. After mixing these purified DNA preparations, a ligation reaction was carried out using Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that the plasmid pKTX93/1131 shown in FIG. 16 was obtained.

2. Stable Expression of 1113-Type and 1131-Type Anti-CD20 Domain-Swapped Antibodies in Animal Cell A cell which stably produces the anti-CD20 antibody domain-swapped antibody was prepared in the same manner as in the item 3 of Example 1. The expression vector for anti-CD20 domain-swapped antibody prepared in the item 1 of this Example was introduced into the CHO/FUT8$^{-/-}$ described in the item 3 of Example 1 as the host cell.

3. Purification of Anti-CD20 Domain-Swapped Antibody

The transformant obtained in the item 2 of this Example capable of expressing the 1113-type anti-CD20 domain-swapped antibody or 1131-type anti-CD20 domain-swapped antibody was cultured and purified in the same manner as in the item 5 of Example 1. The 1113-type anti-CD20 domain-swapped antibody and 1131-type anti-CD20 domain-swapped antibody were purified using the Prosep-G column. In addition, when the 1133-type anti-CD20 domain-swapped antibody, 1113-type anti-CD20 domain-swapped antibody and 1131-type anti-CD20 domain-swapped antibody were purified using Prosep-A column, only the 1131-type anti-CD20 domain-swapped antibody was capable of being purified.

The expression vector and host cell of each domain-swapped antibody and name of the purified antibody are shown in Table 5.

TABLE 5

| Expression vector | Host cell | Purified antibody (name) |
|---|---|---|
| pKTX93/1113 | CHO/FUT8$^{-/-}$ | 1113(–F) |
| pKTX93/1131 | CHO/FUT8$^{-/-}$ | 1131(–F) |

4. Evaluation of Purification Degree of Purified Anti-CD20 Domain-Swapped Antibodies by SDS-PAGE In order to measure purification degree of the purified samples of various anti-CD20 domain-swapped antibodies obtained in the item 3 of this Example, SDS-PAGE was carried out in the same manner as in the item 6 of Example 1. As comparative controls of electrophoresis, the same operation was also carried out for the respective purified samples of CD20-IgG1-type, CD20-IgG3-type and 1133-type prepared in the item 5 of Example 1.

Figure 17:
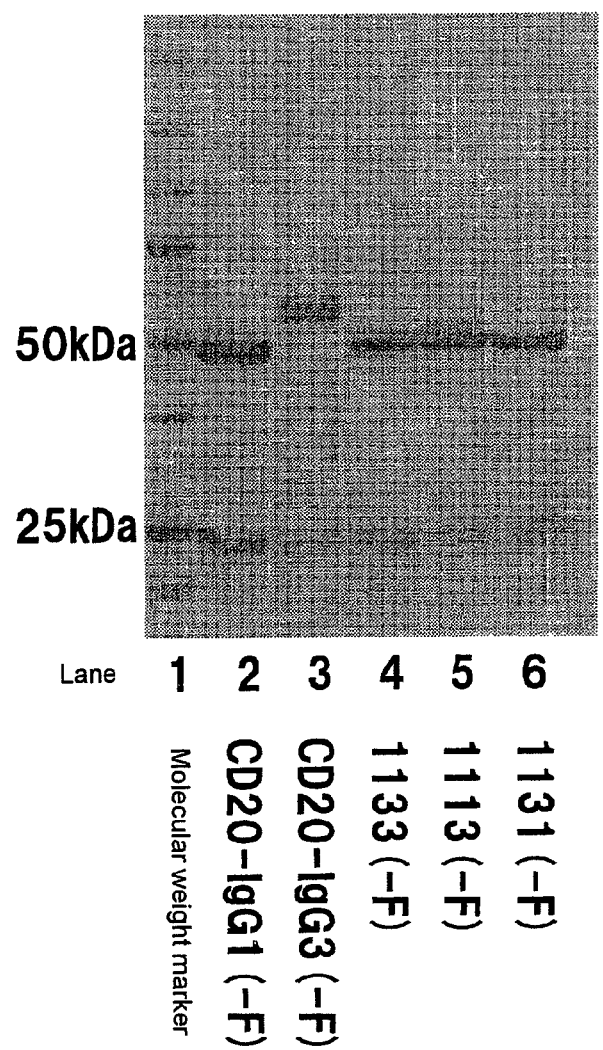
FIG. 17 shows SDS-PAGE electrophoresis patterns of purified 1133-type anti-CD20 domain-swapped antibody, 1113-type anti-CD20 domain-swapped antibody, 1131-type anti-CD20 domain-swapped antibody, anti-CD20 human IgG1 chimeric antibody CD20-IgG1 and anti-CD20 human IgG3 chimeric antibody CD20-IgG3. Staining of protein was carried out with Coomassie Brilliant Blue (CBB). Lane 1 corresponds to CD20-IgG1, lane 2 corresponds to CD20-IgG3, lane 3 corresponds to 1133 and lane 4 corresponds to 1113.

The results are shown in FIG. 17. The 1113-type and 1131-type showed electrophoresis patterns similar to the CD20-IgG1-type and 1133-type, respectively. The molecular weights deduced from the amino acid sequences of H chain and L chain constituting the 1113-type and 1131-type are similar to each other, and the H chain is about 50 kDa and the L chain is about 24 kDa. Since these molecular weights are similar to the H chain and L chain molecular weights of the CD20-IgG1-type and 1133-type, and the electrophoresis patterns are also similar thereto, it was confirmed that the 1113-type and 1131-type are constituted by the desired H chain and L chain. In addition, the molecular weight deduced from the amino acid sequence of L chain constituting the CD20-IgG3-type was about 24 kDa which is similar to that of the CD20-IgG1-type, but the H chain constituting the CD20-IgG3-type was about 54 kDa which is larger than that of the H chain of the CD20-IgG1-type, so that L chain of the CD20-IgG3-type appeared at a position similar to that of the L chain of the CD20-IgG1-type, but the bond of H chain of the CD20-IgG3-type was positioned at a high molecular weight side than that of H chain of the CD20-IgG1-type.

From the above results, it was confirmed that the desired IgG molecules respectively constituted by H chain and L chain are contained at a sufficient ratio in the purified samples of various anti-CD20 domain-swapped antibodies obtained in the item 3 of this Example.

Example 4

Activity Evaluation of 1131-Type and 1113-Type Anti-CD20 Domain-Swapped Antibodies Comparison of various activities was carried out in the following manner, on the purified samples of the various anti-CD20 domain-swapped antibodies obtained in the item 3 of Example 3.

1. CDC Activity of 1113-Type and 1131-Type Anti-CD20 Domain-Swapped Antibodies

In order to evaluate in vitro CDC activity of the CD20-IgG1-type anti-CD20 human IgG1 chimeric antibody, CD20-IgG3-type anti-CD20 human IgG3 chimeric antibody and 1133-type anti-CD20 domain-swapped antibody obtained in the item 5 of Example 1 and the 1113-type anti-CD20 domain-swapped antibody and 1131-type anti-CD20 domain-swapped antibody obtained in the item 3 of Example 3, in a CD20-positive cell line, the test was carried out in the same manner as in the item 2 of Example 2 using a CD20-positive ST 486 cell or Raji cell.

The results are shown in FIG. 18. As shown in FIG. 18, the CDC activity of CD20-IgG3(–F) was higher than the CDC activity of CD20-IgG1(–F) in each of the ST 486 cell line (FIG. 18A) and the Raji cell line (FIG. 18B), and the CDC activity of 1133(–F) was higher than the CDC activity of CD20-IgG3(–F). In addition to this, the CDC activity of 1113(–F) and 1131(–F) was higher than the CDC activity of CD20-IgG3(–F). Also, the CDC activity of 1131(–F) was higher than the CDC activity of 1113(–F). From these results, it was found that both of the CH2 domain and CH3 domain from IgG3 are contributing to the increase of CDC activity effected by the replacement of the Fc of IgG1 with the Fc of IgG3. In addition, it was found also from the above-described results that contribution of the CH2 domain is larger between the CH2 domain and CH3 domain.

2. Evaluation of ADCC Activity for CD20-Positive Cell Line

In vitro ADCC activity of the anti-CD20 human IgG1 chimeric antibody CD20-IgG1, anti-CD20 human IgG3 chimeric antibody CD20-IgG3 and 1133-type anti-CD20 domain-swapped antibody obtained in the item 5 of Example 1 and the 1113-type anti-CD20 domain-swapped antibody and 1131-type anti-CD20 domain-swapped antibody obtained in the item 3 of Example 3 was measured using a CD-positive Daudi cell as the target cell in accordance with the same procedure of the item 5 of Example 2. Cytotox 96™ Kit (manufactured by Promega) was used in the measurement.

Figure 19:
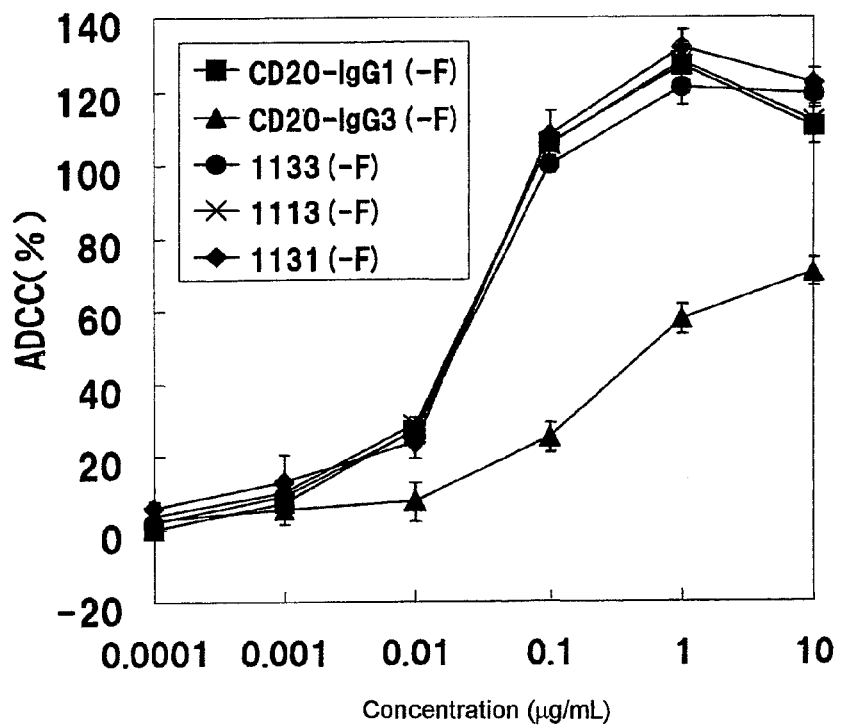
FIG. 19 shows ADCC activity of 1133-type anti-CD20 domain-swapped antibody, 1113-type anti-CD20 domain-swapped antibody, 1131-type anti-CD20 domain-swapped antibody, anti-CD20 human IgG1 chimeric antibody CD20-IgG1 and anti-CD20 human IgG3 chimeric antibody CD20-IgG3 to Daudi cell. The abscissa shows sample concentration, and the ordinate shows ratio of cytotoxicity at each sample concentration. In the graph, ■ shows CD20-IgG1, ▲ shows CD20-IgG3, ● shows 1133, × shows 1113 and ♦ shows 1131.

The results are shown in FIG. 19. As shown in FIG. 19, 1113(–F) and 1131(–F) also show ADCC activity equivalent to CD20-IgG1(–F) and 1133(–F), and these results show that the ADCC activity is substantially equal to that of IgG1, even when the CH2 domain and/or CH3 domain of the anti-CD20 human IgG1 chimeric antibody is subjected to the domain-swap for human IgG3.

Based on the above, it was confirmed that the 1113-type anti-CD20 domain-swapped antibody and 1131-type anti-CD20 domain-swapped antibody having the same variable region of the anti-CD20 human IgG1 chimeric antibody, wherein only the CH2 domain or CH3 domain of the heavy chain constant region contains the amino acid sequence from a human IgG3 antibody and other domains contain the amino acid sequences from a human IgG1 antibody, have CDC activity exceeding that of the anti-CD20 human IgG3 chimeric antibody and ADCC activity equivalent to that of the anti-CD20 human IgG1 chimeric antibody.

Based on the results obtained in the above, relationship between structures and activities of each of the prepared antibody and domain-swapped antibodies is summarized in Table 6. In the table, ADCC activity and CDC activity were expressed as ++++, +++, ++ and + in order of the height of activities. In addition, regarding the binding activity to protein A, those having binding activity to protein A was shown by +, and having no activity as –.

TABLE 6

| Structure name | CH1 | Hinge | CH2 | CH3 | ADCC activity | CDC activity | Protein A binding |
|---|---|---|---|---|---|---|---|
| IgG1(–F) | IgG1 | IgG1 | IgG1 | IgG1 | +++ | + | + |
| IgG3(–F) | IgG3 | IgG3 | IgG3 | IgG3 | ++ | ++ | – |
| 1133(+F)/ 1133(–F) | IgG1 | IgG1 | IgG3 | IgG3 | ++/+++ | +++++ | – |
| 1113(–F) | IgG1 | IgG1 | IgG1 | IgG3 | +++ | +++ | – |
| 1131(–F) | IgG1 | IgG1 | IgG3 | IgG1 | +++ | ++++ | + |

Based on the above, it was found that the greater part of the high CDC activity of an antibody molecule (1133-type domain-swapped antibody) having a heavy chain constant region in which the CH2 domain and the CH3 domain in the human IgG1 antibody heavy chain constant region were swapped for the amino acid sequence from a human IgG3 antibody is also maintained in an antibody molecule (1131-type domain-swapped antibody) having a heavy chain constant region in which only the CH2 domain in the human IgG1 antibody heavy chain constant region was swapped for the amino acid sequence from a human IgG3 antibody. In addition, it was shown that the antibody molecule (1131-type domain-swapped antibody) having a heavy chain constant region in which only the CH2 domain in the human IgG1 antibody heavy chain constant region was replaced by the amino acid sequence from a human IgG3 antibody maintains high ADCC activity equivalent to the human IgG1 antibody, and that the ADCC activity is further enhanced when the fucose bound to the N-acetylglucosamine existing in the reducing terminal in the complex type N-glycoside-linked sugar chain bound to the Fc is removed.

Example 5

Measurement of Binding Activity of Anti-CD20 Domain-Swapped Antibodies to Various Recombinant Fcγ Receptors Binding activity of the anti-CD20 human IgG1 chimeric antibodies CD20-IgG1(−F) and CD20-IgG1(+F) and 1133-type anti-CD20 domain-swapped antibodies 1133(−F) and 1133(+F) to Fc receptor family FcγRI and FcγRIIa was measured in accordance with a conventionally known method [*Clin. Cancer Res.*, 10, 6248 (2004)].

Figure 20:
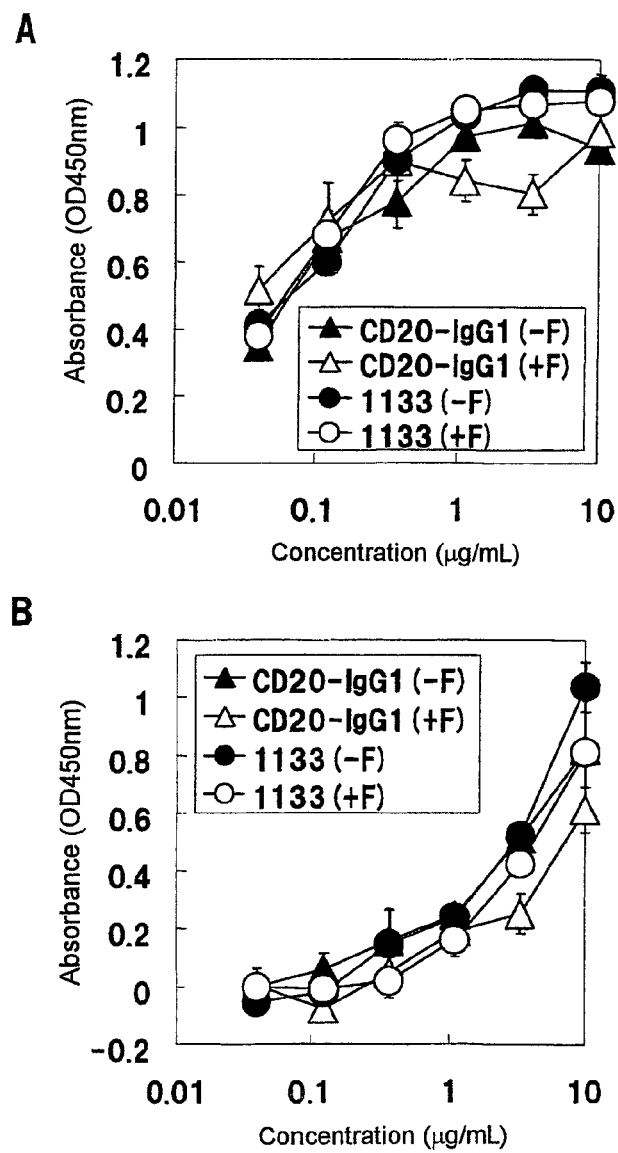
FIG. 20 shows a result of the measurement by ELISA assay, of the binding activity of anti-CD20 human IgG1 chimeric antibodies CD20-IgG1(−F) and CD20-IgG1(+F) and 1133-type anti-CD20 domain-swapped antibody 1133(−F) and 1133(+F) to an Fc receptor family FcγRI (A) or FcγRIIa (B). The abscissa shows sample concentration, and the ordinate shows absorbance at each sample concentration. Graph A shows binding activities of CD20-IgG1(−F) (▲), CD20-IgG1(+F) (Δ), 1133(−F) (●) and 1133(+F) (○) to FcRI, and group B shows those to FcγRIIa.

The results are shown in FIG. 20. As shown in FIG. 20, the 1133-type anti-CD20 domain-swapped antibodies showed their binding activity to FcγRI and also to FcγRIIa at similar level to that of the IgG1 anti-CD20 antibodies. This result shows that replacement of CH2 and CH3 of the IgG1 antibodies by the amino acid sequence of the IgG3 antibodies does not influence on their binding activity to the Fc receptor family FcγRI and FcγRIIa.

In addition, as shown in FIG. 20, regardless of the presence or absence of the fucose bound to the N-acetylglucosamine existing in the reducing terminal in the complex type N-glycoside-linked sugar chain bound to the Fc, each antibody of the 1133-type anti-CD20 domain-swapped antibodies and IgG1 anti-CD20 antibodies showed similar binding activity. The above results show that the presence or absence of the fucose bound to the N-acetylglucosamine existing in the reducing terminal in the complex type N-glycoside-linked sugar chain bound to the Fc does not influence on the binding activity to the Fc receptor family FcγRI and FcγRIIa, and the activity is equivalent to that of the IgG1.

Example 6

Production of Various Anti-CD20 Domain-Swapped Antibodies in which a Polypeptide Containing the Human IgG1 Antibody CH2 Domain is Replaced by a Polypeptide which Corresponds to the Human IgG3 Antibody Indicated by the EU Index, Using Animal Cell 1. Construction of Expression Vectors of Various Anti-CD20 Domain-Swapped Antibodies in which the Entire CH2 Domain and a Part of CH3 Domain were Replaced by Amino Acid Sequences from Human IgG3 Antibody As seen in the item 1 of Example 4, it was found that replacement of both of the CH2 domain and the CH3 domain by the amino acid sequences from an IgG3 antibody greatly contributes to the enhancement of CDC activity of the human IgG1 antibody.

On the other hand, as seen in the item 5 of Example 1, the 1133-type anti-CD20 domain-swapped antibody and 1113-type anti-CD20 domain-swapped antibody do not bind to protein A similarly to the case of the human IgG3 antibody, but the 1131-type anti-CD20 domain-swapped antibody binds to protein A similarly to the case of the human IgG1 antibody, and this fact suggests that the CH3 domain containing the amino acid sequence from a human IgG1 antibody contributes to the binding to protein A.

When an antibody is produced as a medicament, it is important that the antibody has binding activity to protein A in view of purifying the antibody easily. Accordingly, domain-swapped antibodies which have CDC activity equivalent to the 1133-type and also have binding activity to protein A were purified by completely replacing the CH2 domain from a human IgG1 with the CH2 domain from a human IgG3 antibody and partially replacing the CH3 domain of IgG1 with the CH3 domain from a human IgG3 antibody.

Figure 21:
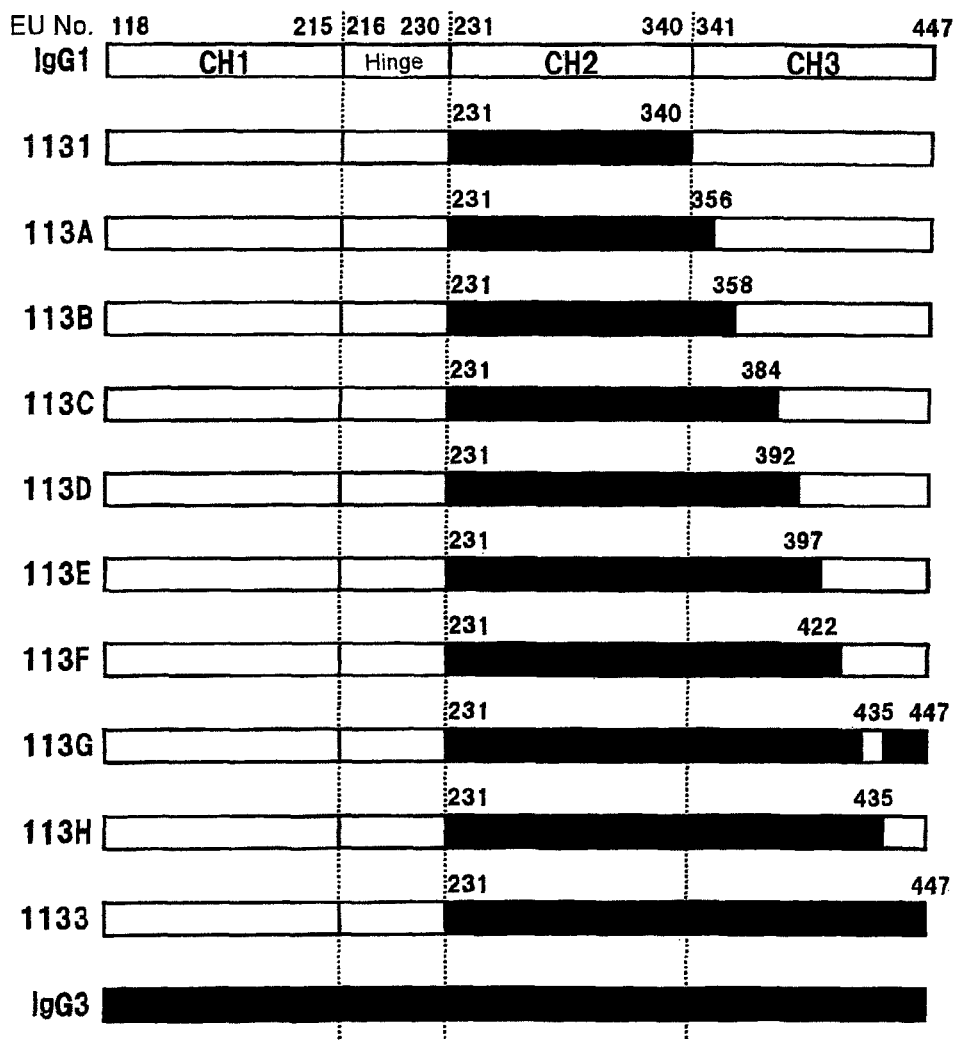
FIG. 21 is a schematic illustration showing domain structures of antibodies 113A, 113B, 113C, 113D, 113E, 113F, 113G and 113H prepared by partially replacing the CH3 domain of 1133-type anti-CD20 domain-swapped antibody with a human IgG1 sequence. In the drawing, the region represented by □ shows amino acid sequence of IgG1, and the region represented by ■ shows amino acid sequence of IgG3, and the numerals shown on the upper side of both terminals of the IgG3 region are EU indexes which correspond to the positions of the IgG3 amino acid residues positioned on both terminals.

A schematic illustration of heavy chain constant regions of various anti-CD20 domain-swapped antibodies designed in this Example is shown in FIG. 21. Since amino acid sequences of the heavy chain constant regions of these domain-swapped antibodies are unknown, each of them is a novel structure. The CH2 domain of the IgG antibody contains the amino acid residues at positions 231 to 340 indicated by the EU index, and the CH3 domain thereof contains the amino acid residues at positions 341 to 447 indicated by the EU index.

The 113A-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 356 of a human IgG3 antibody indicated by the EU index.

The 113B-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 358 of a human IgG3 antibody indicated by the EU index.

The 113C-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 384 of a human IgG3 antibody indicated by the EU index.

The 113D-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 392 of a human IgG3 antibody indicated by the EU index.

The 113E-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 397 of a human IgG3 antibody indicated by the EU index.

The 113F-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 422 of a human IgG3 antibody indicated by the EU index.

The 113G-type anti-CD20 domain-swapped antibody is a domain-swapped antibody in which a polypeptide comprising the CH2 domain in the heavy chain constant region of the anti-CD20 human IgG1 chimeric antibody is replaced by polypeptides corresponding to positions 231 to 434 and positions 436 to 447 of a human IgG3 antibody indicated by the EU index.

The 113H-type anti-CD20 domain-swapped antibody is a domain-swapped antibody in which a polypeptide comprising the CH2 domain in the heavy chain constant region of the anti-CD20 human IgG1 chimeric antibody is replaced by a polypeptide corresponding to positions 231 to 435 of a human IgG3 antibody indicated by the EU index.

These various anti-CD20 domain-swapped antibodies were prepared by the following procedure.

Each of these anti-CD20 domain-swapped antibodies can be produced by preparing a DNA fragment encoding the amino acid sequence of the CH3 domain of each domain-swapped antibody, and replacing it with a nucleotide sequence of the expression vector for 1133-type anti-CD20 domain-swapped antibody, pKTX93/1133 prepared in the item 2 of Example 2, encoding the amino acid sequence of the CH3 domain thereof. Replacement of the nucleotide sequence encoding the heavy chain CH3 domain can be carried out using a restriction enzyme recognition sequence Bsp1407I positioned at the 5'-terminal side in the nucleotide sequence encoding the heavy chain CH3 domain and a restriction enzyme recognition sequence NruI positioned at the 3'-terminal side in the nucleotide sequence encoding the heavy chain CH3 domain.

Figure 22:
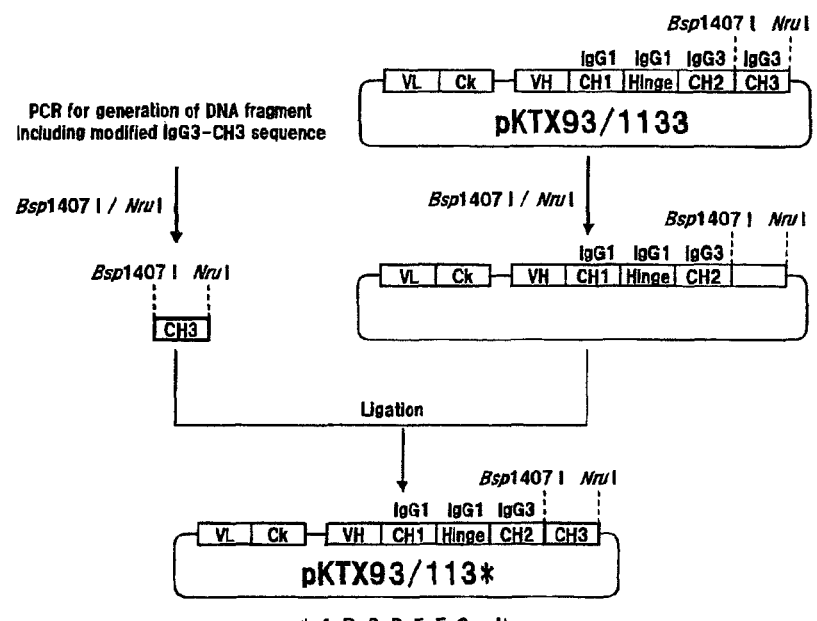
FIG. 22 shows construction steps of expression vector plasmid of various antibodies in which the CH3 domain of 1133-type anti-CD20 domain-swapped antibody was partially replaced by a human IgG1 sequence.

(1) Construction of Expression Vector Comprising the Nucleotide Sequence Encoding 113A-Type Anti-CD20 Domain-Swapped Antibody An expression vector comprising the nucleotide sequence of the 113A-type domain-swapped antibody in which a polypeptide comprising the CH2 domain in the heavy chain constant region of anti-CD20 human IgG1 chimeric antibody was replaced by a polypeptide corresponding to positions 231 to 356 of a human IgG3 antibody indicated by the EU index was constructed by the procedure shown below (FIG. 22). The amino acid sequence of the heavy chain constant region of 113A-type anti-CD20 domain-swapped antibody is shown in SEQ ID NO:33.

Firstly, the nucleotide sequence represented by SEQ ID NO:34 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 356 indicated by the EU index was based on the amino acid sequence from a human IgG3 antibody, and the amino acid sequence at positions 357 to 447 indicated by the EU index was based on the amino acid sequence from a human IgG1 antibody. Next, each of the nucleotide sequences represented by SEQ ID NOs:35 and 36 was designed. The nucleotide sequences represented by SEQ ID NOs:35 and 36 are the nucleotide sequences of a sense primer and an antisense primer, respectively, for amplifying a DNA fragment consisting of the nucleotide sequence represented by SEQ ID NO:34 by PCR.

Each of synthetic oligo DNAs of the nucleotide sequences represented by SEQ ID NOs:35 and 36 was prepared (manufactured by FASMAC), and PCR was carried out using, as the template, the expression vector plasmid of 1133-type anti-CD20 domain-swapped antibody prepared in the item 2 of Example 2. By preparing a reaction solution for PCR [0.05 unit/μl KOD DNA Polymerase (manufactured by TOYOBO), 0.2 mM dNTPs, 1 mM magnesium chloride, 1/10 volume of 10-fold concentrated PCR Buffer #2 (manufactured by TOYOBO, attached to the KOD DNA Polymerase)] in such a manner that each of the two synthetic oligo DNA become the final concentration of 0.5 μM, and PCR was carried out using a DNA thermal cycler GeneAmp PCR System 9700™ (manufactured by Applied Biosystems) by heating at 94° C. for 4 minutes, followed by 25 cycles consisting of 3 steps of reactions at 94° C. for 30 seconds, at 55° C. for 30 seconds and at 74° C. for 60 seconds. After completion of the PCR, the reaction solution was subjected to agarose gel electrophoresis, and a PCR product of about 300 bp was recovered using QIAquick™ Gel Extraction Kit (manufactured by QIAGEN). The thus recovered PCR product was digested with a restriction enzyme Bsp1407I (manufactured by Takara Shuzo) and a restriction enzyme NruI (manufactured by Takara Shuzo), and then the reaction solution was subjected to agarose gel electrophoresis, and a DNA fragment of about 300 bp was cleaved and purified using QIAquick™ Gel Extraction Kit (manufactured by QIAGEN). On the other hand, a DNA fragment of about 13 kbp was cleaved and purified by the same treatment with restriction enzymes on the expression vector plasmid of 1133-type anti-CD20 domain-swapped antibody prepared in the item 2 of Example 2. After mixing these purified DNA fragments, a ligation reaction was carried out by adding Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that expression vector plasmid for 113A-type anti-CD20 domain-swapped antibody, pKTX93/113A was obtained.

(2) Construction of Expression Vector Comprising the Nucleotide Sequence Encoding 113B-Type Anti-CD20 Domain-Swapped Antibody An expression vector comprising the nucleotide sequence of the 113B-type domain-swapped antibody in which a polypeptide containing the CH2 domain in the heavy chain constant region of anti-CD20 human IgG1 chimeric antibody was replaced by a polypeptide corresponding to positions 231 to 358 of a human IgG3 antibody indicated by the EU index was constructed by the procedure shown below (FIG. 22). The amino acid sequence of the heavy chain constant region of 113B-type anti-CD20 domain-swapped antibody is shown in SEQ ID NO:37.

Firstly, the nucleotide sequence represented by SEQ ID NO:38 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 358 indicated by the EU index was based on the amino acid sequence from a human IgG3 antibody, and the amino acid sequence at positions 359 to 447 indicated by the EU index was based on the amino acid sequence from a human IgG1 antibody. Next, the nucleotide sequence represented by SEQ ID NO:39 was designed. The nucleotide sequence represented by SEQ ID NO:39 is the nucleotide sequence of a sense primer for use in the amplification of a DNA fragment containing the nucleotide sequence represented by SEQ ID NO:38 by PCR, and was used in combination with an antisense primer containing the nucleotide sequence represented by SEQ ID NO:36. Each of synthetic oligo DNAs of the nucleotide sequences represented by SEQ ID NOs:39 and 36 was prepared (manufactured by FASMAC), and PCR was carried out using, as the template, the expression vector plasmid for 1133-type anti-CD20 domain-swapped antibody prepared in the item 2 of Example 2. Thereafter, expression vector plasmid for 113B-type anti-CD20 domain-swapped antibody, pKTX93/113B was prepared in the same manner as in the (1) of this item.

(3) Construction of Expression Vector Comprising the Nucleotide Sequence Encoding 113C-Type Anti-CD20 Domain-Swapped Antibody An expression vector comprising the nucleotide sequence of the 113C-type domain-swapped antibody in which a polypeptide comprising the CH2 domain in the heavy chain constant region of anti-CD20 human IgG1 chimeric antibody was replaced by a polypeptide corresponding to positions 231 to 384 of a human IgG3 antibody indicated by the EU index was constructed by the procedure shown below (FIG. 22). The amino acid sequence of the heavy chain constant region of 113C-type anti-CD20 domain-swapped antibody is shown in SEQ ID NO:40.

Firstly, the nucleotide sequence represented by SEQ ID NO:41 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 384 indicated by the EU index was based on the amino acid sequence from a human IgG3 antibody, and the amino acid sequence at positions 385 to 447 indicated by the EU index was based on the amino acid sequence from a human IgG1 antibody. Next, each of the nucleotide sequences represented by SEQ ID NOs:42 and 43 was designed. The nucleotide sequences represented by SEQ ID NOs:42 and 43 are nucleotide sequences of synthetic oligo DNA for amplifying a DNA fragment containing the nucleotide sequence represented by SEQ ID NO:41 by PCR. The 3'-terminal side of the nucleotide sequence represented by SEQ ID NO:42 and the 5'-terminal side of the nucleotide sequence represented by SEQ ID NO:43 were designed in such a manner that approximately 20 bps thereof were mutually overlapped like a complementary sequence so that annealing was caused when PCR was carried out. Each of synthetic oligo DNAs of the nucleotide sequences represented by SEQ ID NOs:42 and 43 was prepared (manufactured by FASMAC), and PCR was carried out. By preparing a reaction solution for PCR [0.02 unit/µl KOD+DNA Polymerase (manufactured by TOYOBO), 0.2 mM dNTPs, 1 mM magnesium chloride, 1/10 volume of 10-fold concentrated PCR Buffer (manufactured by TOYOBO), attached to the KOD+DNA Polymerase)] in such a manner that each of the two synthetic oligo DNAs become the final concentration of 0.2 µM, and PCR was carried out using a DNA thermal cycler GeneAmp PCR System 9700 (manufactured by Applied Biosystems) by heating at 94° C. for 4 minutes, followed by 25 cycles of 3 steps of reactions at 94° C. for 30 seconds, at 55° C. for 30 seconds and 68° C. for 60 seconds. Thereafter, expression vector plasmid for 113C-type anti-CD20 domain-swapped antibody, pKTX93/113C was prepared in the same manner as in the (1) of this item.

(4) Construction of Expression Vector Comprising the Nucleotide Sequence Encoding 113D-Type Anti-CD20 Domain-Swapped Antibody An expression vector comprising the nucleotide sequence of 113D-type domain-swapped antibody in which a polypeptide comprising the CH2 domain in the heavy chain constant region of anti-CD20 human IgG1 chimeric antibody was replaced by a polypeptide corresponding to positions 231 to 392 of a human IgG3 antibody indicated by the EU index was constructed by the procedure shown below (FIG. 22). The amino acid sequence of the heavy chain constant region of 113D-type anti-CD20 domain-swapped antibody is shown in SEQ ID NO:44.

Firstly, the nucleotide sequence represented by SEQ ID NO:45 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 392 indicated by the EU index was based on the amino acid sequence from a human IgG3 antibody, and the amino acid sequence at positions 393 to 447 indicated by the EU index was based on the amino acid sequence from a human IgG1 antibody. Next, the nucleotide sequence represented by SEQ ID NO:46 was designed. The nucleotide sequence represented by SEQ ID NO:46 is the nucleotide sequence of a synthetic oligo DNA for use in the amplification of a DNA fragment containing the nucleotide sequence represented by SEQ ID NO:45 by PCR, which is used in combination with a synthetic oligo DNA containing the nucleotide sequence represented by SEQ ID NO:43. The 3'-terminal side of the nucleotide sequence represented by SEQ ID NO:46 and the 5'-terminal side of the nucleotide sequence represented by SEQ ID NO:43 were designed in such a manner that approximately 20 bps thereof were mutually overlapped so that annealing was caused when PCR was carried out. Each of synthetic oligo DNAs of the nucleotide sequences represented by SEQ ID NOs:46 and 43 was prepared (manufactured by FASMAC), and PCR was carried out. Thereafter, expression vector plasmid for 113D-type anti-CD20 domain-swapped antibody, pKTX93/113D was prepared in the same manner as in (3) of this item.

(5) Construction of Expression Vector Comprising the Nucleotide Sequence Encoding 113E-Type Anti-CD20 Domain-Swapped Antibody An expression vector comprising the nucleotide sequence of the domain-swapped antibody 113E-type in which a polypeptide comprising the CH2 domain in the heavy chain constant region of anti-CD20 human IgG1 chimeric antibody was replaced by a polypeptide corresponding to positions 231 to 397 of a human IgG3 antibody indicated by the EU index was constructed by the procedure shown below (FIG. 22). The amino acid sequence of the heavy chain constant region of 113E-type anti-CD20 domain-swapped antibody is shown in SEQ ID NO:47.

Firstly, the nucleotide sequence represented by SEQ ID NO:48 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 397 indicated by the EU index was based on the amino acid sequence from a human IgG3 antibody, and the amino acid sequence at positions 398 to 447 indicated by the EU index was based on the amino acid sequence from a human IgG1 antibody. Next, the nucleotide sequences represented by SEQ ID NO:49 was designed. The nucleotide sequence represented by SEQ ID NO:49 is the nucleotide sequence of a synthetic oligo DNA for use in the amplification of a DNA fragment containing the nucleotide sequence represented by SEQ ID NO:48 by PCR, which is used in combination with a synthetic oligo DNA containing the nucleotide sequence represented by SEQ ID NO:43. The 3'-terminal side of the nucleotide sequence represented by SEQ ID NO:49 and the 5'-terminal side of the nucleotide sequence represented by SEQ ID NO:43 were designed in such a manner that approximately 20 bps thereof were mutually overlapped so that annealing was caused when PCR was carried out. Each of synthetic oligo DNAs of the nucleotide sequences represented by SEQ ID NOs:49 and 43 was prepared (manufactured by FASMAC), and PCR was carried out. Thereafter, expression vector plasmid for 113E-type anti-CD20 domain-swapped antibody, pKTX93/113E was prepared in the same manner as in (3) of this item.

(6) Construction of Expression Vector Comprising the Nucleotide Sequence Encoding 113F-Type Anti-CD20 Domain-Swapped Antibody An expression vector comprising the nucleotide sequence of the 113F-type domain-swapped antibody in which a polypeptide comprising the CH2 domain in the heavy chain constant region of anti-CD20 human IgG1 chimeric antibody was replaced by a polypeptide corresponding to positions 231 to 422 of a human IgG3 antibody indicated by the EU index was constructed by the procedure shown below (FIG. 22). The amino acid sequence of the heavy chain constant region of 113F-type anti-CD20 domain-swapped antibody is shown in SEQ ID NO:50.

Firstly, the nucleotide sequence represented by SEQ ID NO:51 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 422 indicated by the EU index was based on the amino acid sequence from a human IgG3 antibody, and the amino acid sequence at positions 423 to 447 indicated by the EU index was based on the amino acid sequence from a human IgG1 antibody. Each of synthetic oligo DNAs of the nucleotide sequences represented by SEQ ID NOs:39 and 36 was prepared (manufactured by FASMAC), and PCR was carried out using, as the template, the expression vector plasmid for anti-CD20 human IgG3 chimeric antibody, pKANTEX2B8γ3 prepared in the item 1 of Example 1. Thereafter, expression vector plasmid for 113F-type anti-CD20 domain-swapped antibody, pKTX93/113F was prepared in the same manner as in (1) of this item.

(7) Construction of Expression Vector Comprising the Nucleotide Sequence Encoding 113H-Type Anti-CD20 Domain-Swapped Antibody An expression vector comprising the nucleotide sequence of the 113H-type domain-swapped antibody in which a polypeptide comprising the CH2 domain in the heavy chain constant region of anti-CD20 human IgG1 chimeric antibody was replaced by a polypeptide corresponding to positions 231 to 435 of a human IgG3 antibody indicated by the EU index was constructed by the procedure shown below (FIG. 22). The amino acid sequence of the heavy chain constant region of 113H-type anti-CD20 domain-swapped antibody is shown in SEQ ID NO:52.

Firstly, the nucleotide sequence represented by SEQ ID NO:53 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 435 indicated by the EU index was based on the amino acid sequence from a human IgG3 antibody, and the amino acid sequence at positions 436 to 447 indicated by the EU index was based on the amino acid sequence from a human IgG1 antibody. Next, the nucleotide sequence represented by SEQ ID NO:54 was designed. The nucleotide sequence represented by SEQ ID NO:54 is a nucleotide sequence of the antisense primer to be used in the amplification of a DNA fragment containing the nucleotide sequence represented by SEQ ID NO:53 by PCR, which is used in combination with the sense primer containing the nucleotide sequence represented by SEQ ID NO:39. Each of synthetic oligo DNAs of the nucleotide sequences represented by SEQ ID NOs:39 and 54 was prepared (manufactured by FASMAC), and PCR was carried out using, as the template, the expression vector plasmid for anti-CD20 human IgG3 chimeric antibody, pKANTEX2B8γ3 prepared in the item 1 of Example 1. Thereafter, expression vector plasmid for 113H-type anti-CD20 domain-swapped antibody, pKTX93/113H was prepared in the same manner as in (1) of this item.

(8) Construction of Expression Vector Comprising the Nucleotide Sequence Encoding 113G-Type Anti-CD20 Domain-Swapped Antibody An expression vector comprising the nucleotide sequence of the 113G-type domain-swapped antibody in which a polypeptide containing the CH2 domain in the heavy chain constant region of anti-CD20 human IgG1 chimeric antibody was replaced by a polypeptide corresponding to positions 231 to 434 of a human IgG3 antibody indicated by the EU index was constructed by the procedure shown below (FIG. 22).

The amino acid sequence of the heavy chain constant region of 113G-type anti-CD20 domain-swapped antibody is shown in SEQ ID NO:55.

Firstly, the nucleotide sequence represented by SEQ ID NO:56 was designed. The sequence was designed based on the sequence of a restriction enzyme recognition sequence Bsp1407I positioned at the 5'-terminal side in the nucleotide sequence encoding the heavy chain CH3 domain to a restriction enzyme recognition sequence NruI positioned at the 3'-terminal side in the nucleotide sequence encoding the heavy chain CH3 domain, on the expression vector for 1133-type anti-CD20 domain-swapped antibody prepared in the item 2 of Example 2, and among the amino acid sequences encoded by the nucleotide sequences, the amino acid sequence of the N-terminal side to position 434 indicated by the EU index was based on the amino acid sequence from a human IgG3 antibody, the amino acid sequence at position 435 indicated by the EU index was based on the amino acid sequence from a human IgG1 antibody, and the amino acid sequence at positions 436 to 447 indicated by the EU index was based on the amino acid sequence from a human IgG3 antibody. Next, the nucleotide sequence represented by SEQ ID NO:57 was designed. The nucleotide sequence represented by SEQ ID NO:57 is a nucleotide sequence of the antisense primer to be used in the amplification of a DNA fragment containing the nucleotide sequence represented by SEQ ID NO:56 by PCR, which is used in combination with the sense primer containing the nucleotide sequence represented by SEQ ID NO:39. Each of synthetic oligo DNAs of the nucleotide sequences represented by SEQ ID NOs:39 and 56 was prepared (manufactured by FASMAC), and PCR was carried out using, as the template, the expression vector plasmid for anti-CD20 human IgG3 chimeric antibody, pKANTEX2B8γ3 prepared in the item 1 of Example 1. Thereafter, expression vector plasmid for 113G-type anti-CD20 domain-swapped antibody, pKTX93/113G was prepared in the same manner as in (1) of this item.

2. Stable Expression of Various Anti-CD20 Domain-Swapped Antibodies in which the Entire CH2 Domain and a Part of CH3 Domain were Replaced by the Amino Acid Sequences from a Human IgG3 Antibody, in Animal Cell A cell capable of stably producing each of various anti-CD20 domain-swapped antibodies in which the entire CH2 domain and a part of CH3 domain were replaced by the amino acid sequences from a human IgG3 antibody was prepared in the same manner as in the item 3 of Example 1, by introducing each of the expression vectors of anti-CD20 domain-swapped antibodies in which the entire CH2 domain and a part of CH3 domain were replaced by the amino acid sequences from a human IgG3 antibody, prepared in the item 1 of this Example, into the host cell CHO/FUT8$^{-/-}$ described in the item 3 of Example 1.

3. Purification of Various Anti-CD20 Domain-Swapped Antibodies in which the Entire CH2 Domain and a Part of the CH3 Domain were Replaced by the Amino Acid Sequence from a Human IgG3 Antibody:

Each of the transformants obtained in the item 2 of this Example capable of expressing various anti-CD20 domain-swapped antibodies in which the entire CH2 domain and a part of the CH3 domain were replaced by the amino acid sequences from a human IgG3 antibody was cultured and purified in the same manner as in the item 5 of Example 1. Prosep-G column was used in the purification. Corresponding expression vector, host cell, name of the purified antibody and amino acid sequence of heavy chain constant region of each of the modified antibodies are shown in Table 7.

TABLE 7

| Expression vector | Host cell | Purified antibody (name) | Amino acid sequence |
|---|---|---|---|
| PKTX93/113A | Ms705 | 113A(-F) | SEQ ID NO: 33 |
| PKTX93/113B | Ms705 | 113B(-F) | SEQ ID NO: 37 |
| PKTX93/113C | Ms705 | 113C(-F) | SEQ ID NO: 40 |
| PKTX93/113D | Ms705 | 113D(-F) | SEQ ID NO: 44 |
| PKTX93/113E | Ms705 | 113E(-F) | SEQ ID NO: 47 |
| PKTX93/113F | Ms705 | 113F(-F) | SEQ ID NO: 50 |
| PKTX93/113G | Ms705 | 113G(-F) | SEQ ID NO: 55 |
| PKTX93/113H | Ms705 | 113H(-F) | SEQ ID NO: 52 |

4. Evaluation of the Purification Degree of Various Anti-CD20 Domain-Swapped Antibodies by SDS-PAGE In order to evaluate purification degree of the purified samples of various anti-CD20 domain-swapped antibodies obtained in the item 3 of this Example, SDS-PAGE was carried out in the same manner as in the item 6 of Example 1. As comparative controls of the electrophoresis, the same operation was carried out also on the purified samples CD20-IgG1(-F) and 1133(-F) prepared in the item 5 of Example 1.

Figure 23:
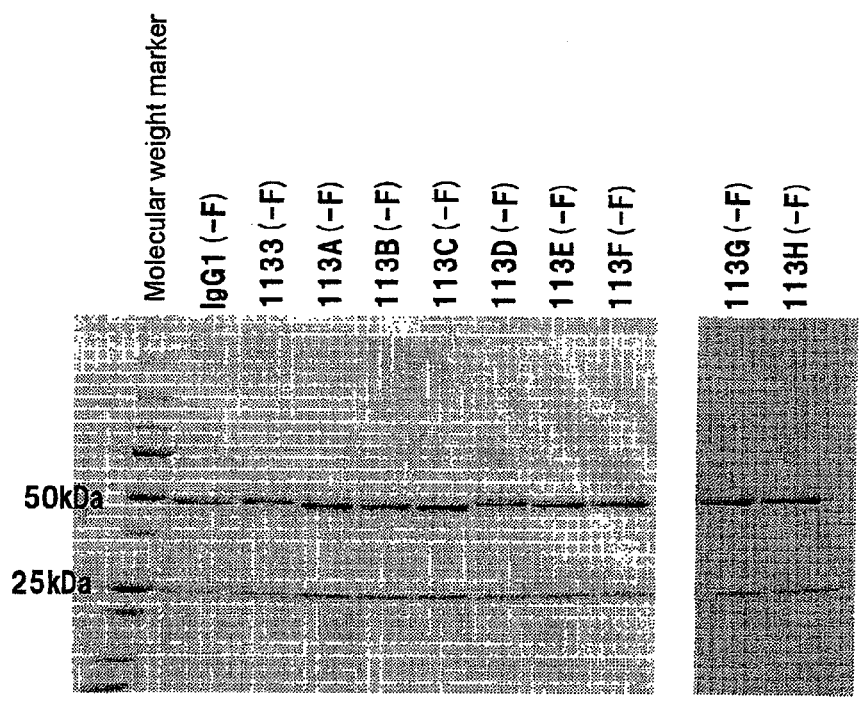
FIG. 23 shows SDS-PAGE electrophoresis patterns of purified samples in which the CH3 domain of 1133-type anti-CD20 domain-swapped antibody was partially replaced by a human IgG1 sequence. Staining of protein was carried out with Coomassie Brilliant Blue (CBB). Starting from the left side, the lanes corresponds to molecular weight markers, CD20-IgG1(−F), 1133(−F), 113A(−F), 113B(−F), 113C(−F), 113D(−F), 113E(−F), 113F(−F), 113G(−F), and 113H(−F).

The results are shown in FIG. 23. Each of purified samples of the anti-CD20 domain-swapped antibodies obtained in the item 3 of this Example showed similar electrophoresis patterns of the CD20-IgG1(-F) and 1133(-F). The molecular weights deduced from the amino acid sequences of H chain and L chain constituting each of the various anti-CD20 domain-swapped antibodies was similar to each other, namely the H chain was about 50 kilodaltons (hereinafter referred to as kDa) and the L chain was about 24 kDa. Since these molecular weights are similar to the molecular weights of the H chain and L chain of CD20-IgG1(-F) and 1133(-F) and their electrophoresis patterns are also similar thereto, it was confirmed that each of the various anti-CD20 domain-swapped antibody is constituted by the desired H chain and L chain.

Based on the above results, it was confirmed that the desired IgG molecules respectively constituted by the H chain and L chain are contained at a sufficient ratio in the purified samples of various anti-CD20 domain-swapped antibodies obtained in the item 3 of this Example.

Example 7

Activity Evaluation of Various Anti-CD20 Domain-Swapped Antibodies in which the Entire CH2 Domain and a Part of CH3 Domain were Replaced by Amino Acid Sequences from Human IgG3 Antibody Comparison of various activities was carried out for the purified samples of various anti-CD20 domain-swapped antibodies obtained in the item 3 of Example 6 in the following manner.

1. Measurement of the CDC Activity of Various Anti-CD20 Domain-Swapped Antibodies in which the Entire CH2 Domain and a Part of CH3 Domain were Replaced by Amino Acid Sequences from Human IgG3 Antibody The in vitro CDC activity in a human CD20 gene-introduced cell line CD20/EL4-A [Clin. Cancer Res., 11, 2327 (2005)] was measured for the purified samples of various anti-CD20 domain-swapped antibodies obtained in the item 3 of Example 6, the 1133-type anti-CD20 domain-swapped antibody obtained in the item 5 of Example 1 and the 1131-type anti-CD20 domain-swapped antibody obtained in the item 3 of Example 3. The reaction was carried out in a 96-well flat-bottomed plate (manufactured by Sumitomo Bakelite), and a human complement dilution medium containing 5×10⁴ cells of the target cell and containing each anti-CD20 domain-swapped antibody at varied concentrations (0.1 µg/ml to 30 µg/ml) was dispensed at 150 µl into each reaction well. Thereafter, the test was carried out in the same manner as in the item 2 of Example 2.

Figure 24:
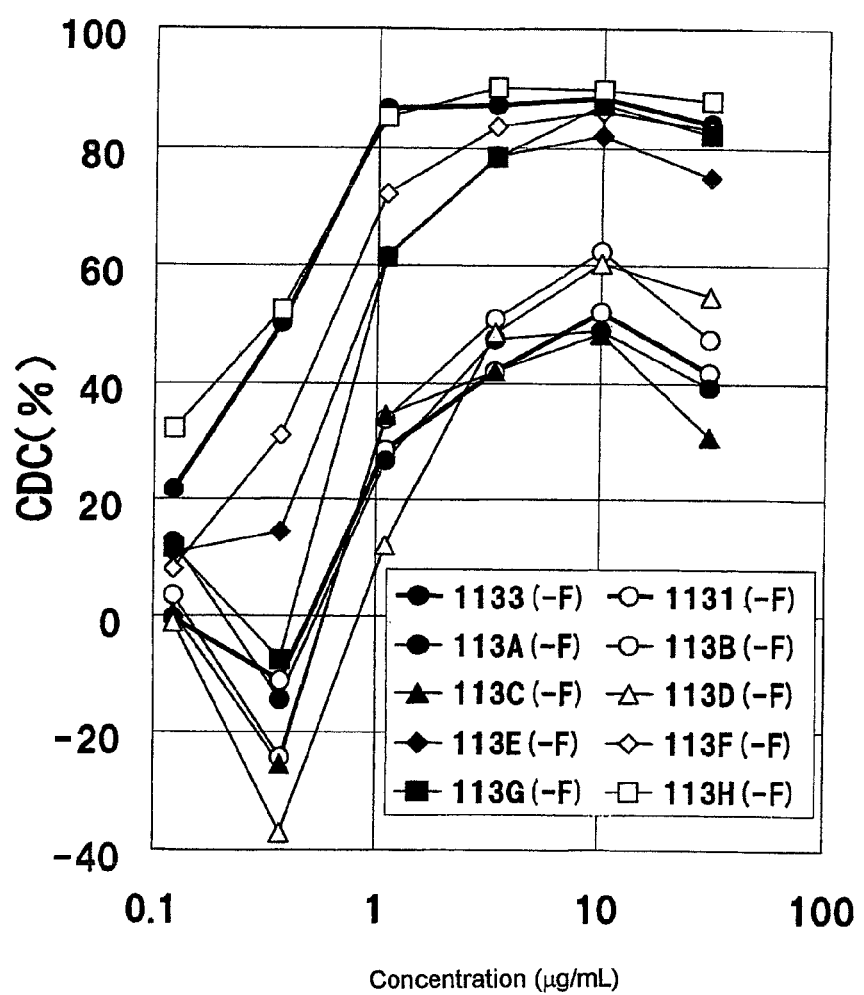
FIG. 24 shows CDC activity of various antibodies in which the CH3 domain of 1133-type anti-CD20 domain-swapped antibody was partially replaced by a human IgG1 sequence, 1133-type anti-CD20 domain-swapped antibody and 1131-type anti-CD20 domain-swapped antibody to CD20-positive cells. The abscissa shows sample concentration, and the ordinate shows CDC activity at each sample concentration. In the drawings, ● (thick line) shows 1133(−F), ○ (thick line) shows 1131(−F), ● (thin line) shows 113A(−F), ○ (thin line) shows 113B(–F), ▲ shows 113C(–F), ∆ shows 113D(–F), ◆ shows 113E(–F), ◇ shows 113F(–F), ■ shows 113G(–F) and ☐ shows 113H(–F).

The results are shown in FIG. 24. All of the various anti-CD20 domain-swapped antibodies showed CDC activity of similar to or higher than that of the 1131(–F), particularly, the 113E(–F), 113F(–F), 113G(–F) and 113H(–F) showed strongly higher CDC activity than that of the 1131(–F).

2. Measurement of the Binding Activity to Protein A of Various Anti-CD20 Domain-Swapped Antibodies in which the Entire CH2 Domain and a Part of CH3 Domain were Replaced by Amino Acid Sequences from Human IgG3 Antibody The binding activity to protein A was measured by the procedure described below of the purified samples of various anti-CD20 domain-swapped antibodies obtained in the item 3 of Example 6, the CD20-IgG1(–F), CD20-IgG3(–F) and 113 (–F) obtained in the item 5 of Example 1 and the 1131(–F) and 1113(–F) obtained in the item 3 of Example 3.

A goat anti-human kappa chain antibody (manufactured by Sigma-Aldrich) was diluted with PBS to a concentration of 5 µg/ml, dispensed at 50 µl/well into a 96-well plate for ELISA (manufactured by Greiner) and then allowed to stand at room temperature for 1 hour for adsorption. After the reaction and subsequent washing with PBS, 1% BSA-PBS was added thereto at 100 µl/well and allowed to react at room temperature for 1 hour for blocking the remaining active groups. After removing the 1% BSA-PBS, each antibody to be measured was added thereto at 50 µl/well at varied concentrations (0.01 µg/ml to 10 µg/ml) and allowed to react at room temperature for 2 hours. After the reaction and subsequent washing of each well with Tween-PBS, a peroxidase-labeled protein A solution (manufactured by Amersham Bioscience) diluted 5,000-fold with PBS was added at 50 µl/well and allowed to react at 37° C. for 2 hours. After washing with Tween-PBS, the ABTS substrate solution was added at 50 µl/well for color development, and then OD415 was measured.

Figure 25:
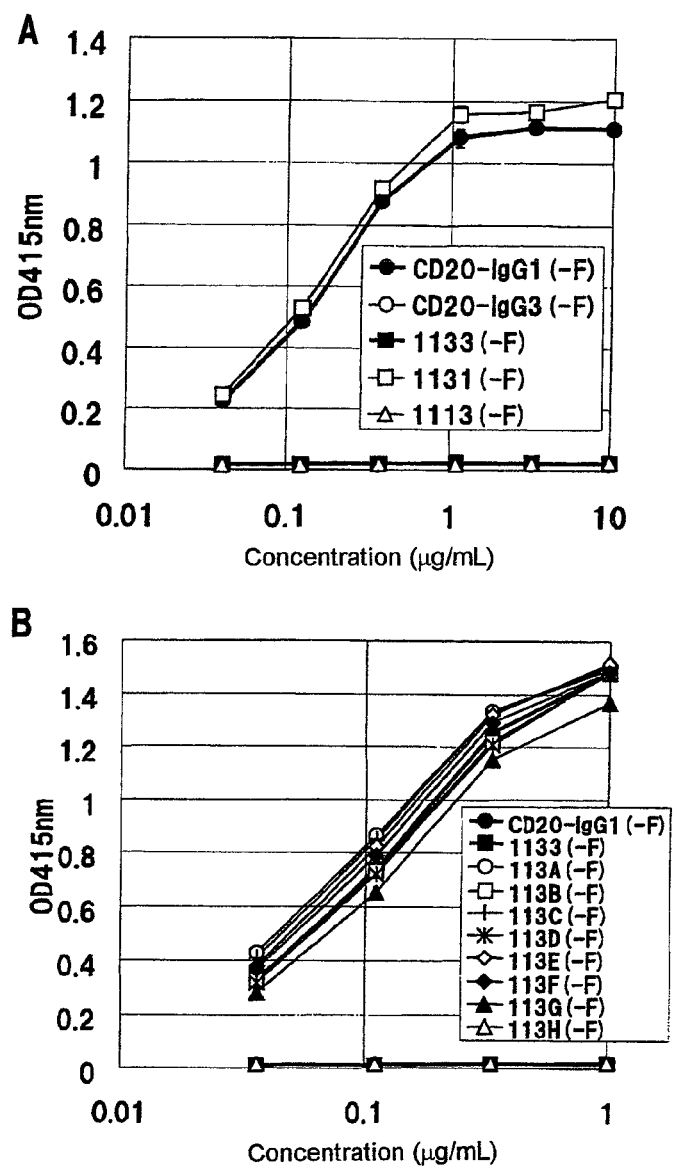
FIG. 25 shows a result of the measurement, by ELISA system, of the binding activity of various antibodies in which the CH3 domain of 1133-type anti-CD20 domain-swapped antibody was partially replaced by a human IgG1 sequence, an anti-CD20 human IgG1 chimeric antibody CD20-IgG1, an anti-CD20 human IgG3 chimeric antibody CD20-IgG3 and 1133-type, 1131-type and 1113-type anti-CD20 domain-swapped antibodies to protein A. The abscissa shows sample concentration, and the ordinate shows absorbance at each sample concentration.

The results are shown in FIG. 25. Firstly, the binding activity to protein A was compared with CD20-IgG1(–F), CD20-IgG3(–F), 1133(–F), 1131(–F) and 1113(–F) (FIG. 25A). As shown in FIG. 25A, both of CD20-IgG1(–F) and 1131(–F) showed binding activity to protein A depending on concentration, and the activity levels are equivalent to each other. In the case of CD20-IgG3(–F), 1133(–F) and 1113(–F), on the other hand, the binding activity to protein A was not found within the measured concentration range (10 µg/ml or less).

Next, the binding activity to protein A of various anti-CD20 domain-swapped antibodies was compared with that of CD20-IgG1(–F) and 1131(–F). As shown in FIG. 25B, 1133 (–F) and 113H(–F) did not show binding activity to protein A, but 113A(–F), 113B(–F), 113C(–F), 113D(–F), 113E(–F), 113F(–F) and 113G(–F) showed binding activity to protein A of equivalent to that of IgG1.

Grades of the CDC activity and protein A binding activity of various anti-CD20 domain-swapped antibodies are shown in Table 8.

TABLE 8

| Antibody | CDC activity | Binding activity to protein A |
|---|---|---|
| CD20-IgG1(–F) | + | + |
| 1131(–F) | ++ | + |
| 113A(–F) | ++ | + |

TABLE 8-continued

| Antibody | CDC activity | Binding activity to protein A |
|---|---|---|
| 113B(–F) | ++ | + |
| 113C(–F) | ++ | + |
| 113D(–F) | ++ | + |
| 113E(–F) | +++ | + |
| 113F(–F) | ++++ | + |
| 113G(–F) | +++ | + |
| 113H(–F) | ++++ | – |
| 1133(–F) | ++++ | – |

In the 1133-type domain-swapped antibody in which CH2 and CH3 of IgG1 antibody were replaced by the amino acid sequences of IgG3, its CDC activity was enhanced, but the binding activity to protein A was deleted. On the other hand, in the 1131-type antibody in which CH2 of IgG1 antibody alone was replaced by the amino acid sequence of IgG3, it maintained the binding activity to protein A but the CDC activity enhancing ratio was reduced. Regarding the various anti-CD20 domain-swapped antibodies prepared in this Example, in which the entire CH2 domain and a part of CH3 domain were replaced by the corresponding amino acid sequences from a human IgG3 antibody, all of them excluding 113H(–F) have CDC activity and binding activity to protein A which were higher than those of IgG1. In addition, 113E(–F), 113F(–F) and 113G(–F) having a relatively high ratio of the amino acid sequence from a human IgG3 antibody occupying the whole CH3 domain showed higher CDC activity than that of 1131(–F) and had binding activity to protein A similar to that of the human IgG1 antibody. Among the anti-CD20 domain-swapped antibodies having similar binding activity to protein A to that of the human IgG1 antibody, 113F(–F) showed particularly high CDC activity.

Based on the above, it was found that, in the antibodies in which the entire CH2 domain of IgG1 antibody was replaced by the CH2 domain from an IgG3 antibody and a part of the CH3 domain was replaced by the CH3 domain from an IgG3 antibody, the CDC activity was enhanced to a level greater than that of the antibodies in which the CH2 domain from an IgG1 antibody alone was replaced by the CH2 domain derived from an IgG3 antibody, and they can maintain the binding activity to protein A similar to that of the human IgG1 antibody.

Example 8

Evaluation of the CDC Activity of Various Anti-CD20 Domain-Swapped Antibodies for Chronic Lymphocytic Leukemia (CLL) Cells Using the CD20-IgG1(–F) obtained in the item 5 of Example 1, 1133(–F) obtained in the item 5 of Example 1, 1131(–F) obtained in the item 3 of Example 3 and 113F(–F) obtained in the item 3 of Example 6, in vitro CDC activity for CD20-positive CLL cell lines MEC-1 (DSMZ: ACC 497), MEC-2 (DSMZ: ACC 500) and EHEB (human, peripheral blood, leukemia, chronic, B cell) (DSMZ: ACC 67) was measured. The reaction was carried out in a 96-well flat-bottomed plate (manufactured by Sumitomo Bakelite), and a human complement dilution medium containing 5×10⁴ cells of the target cell and containing each anti-CD20 antibody at varied concentrations (from 0.04 µg/ml to 100 µg/ml) was dispensed at 150 µl into each reaction well. Thereafter, the test was carried out in the same manner as in the item 2 of Example 2.

Figure 26:
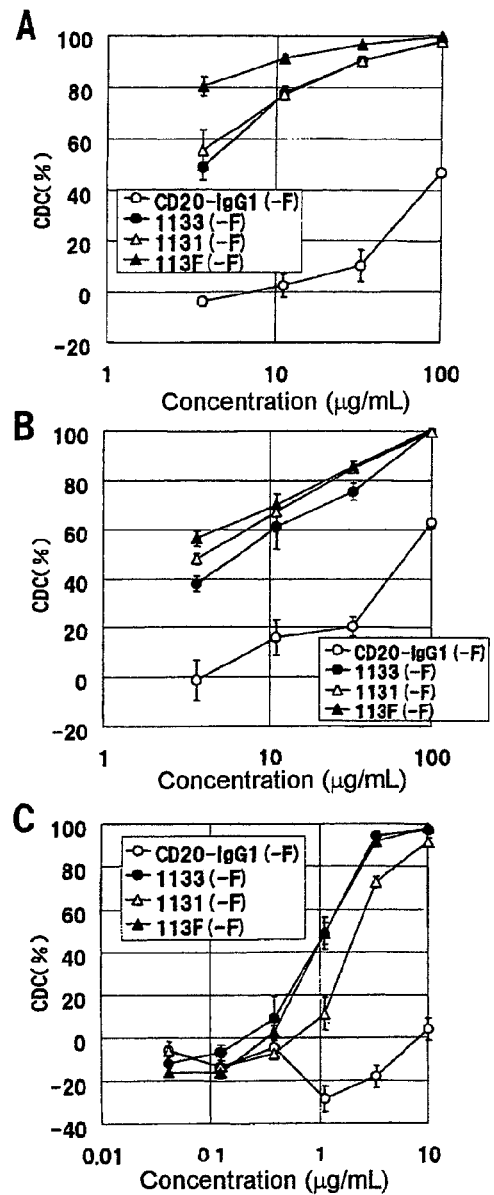
FIG. 26 shows CDC activity of an anti-CD20 human IgG1 chimeric antibody CD20-IgG1 and 1133-type, 1131-type and 113F-type anti-CD20 domain-swapped antibodies to a CD20-positive CLL cell line MEC-1 (A), MEC-2 (B) or EHEB (C). The abscissa shows sample concentration, and the ordinate shows CDC activity at each sample concentration. In the drawing, ○ shows CD20-IgG1, ● shows 1133, ∆ shows 1131 and ▲ shows 113F, respectively.

The results are shown in FIG. 26. In comparison with the CD20-IgG1, CDC activity of 1133(–F), 1131(–F) and 113F (-F) was significantly enhanced for all of the CD20-positive CLL cell lines MEC-1 (FIG. 26A), MEC-2 (FIG. 26B) and EHEB (FIG. 26C). The above results suggest that medicaments containing each of these antibodies as an active ingredient are effective for the treatment of CLL.

Example 9

Preparation of Anti-Campath Human IgG1 Antibody, 1133-Type Anti-Campath Domain-Swapped Antibody and 1131-Type Anti-Campath Domain-Swapped Antibody 1. Construction of Expression Vectors of Anti-Campath Human IgG1 Antibody, 1133-Type Anti-Campath Domain-Swapped Antibody and 1131-Type Anti-Campath Domain-Swapped Antibody In the comparison of the CDC activity of anti-CD20 domain-swapped antibodies 1131(-F) and 1113(-F) carried out in the item 1 of Example 4, both of the 1131(-F) and 1113(-F) showed higher CDC activity than that of the IgG1, and particularly, the 1131(-F) showed higher CDC activity than that of the 1113(-F), and it was found that when the CH2 domain was IgG3, it greatly contributes to the enhancement of CDC activity. In order to confirm that similar CDC activity enhancement can also be found in the antibodies for other antigen, human IgG1, 1133-type and 1131-type of the humanized anti-Campath antibody Campath-1H were prepared to compare their CDC activity.

Figure 27:
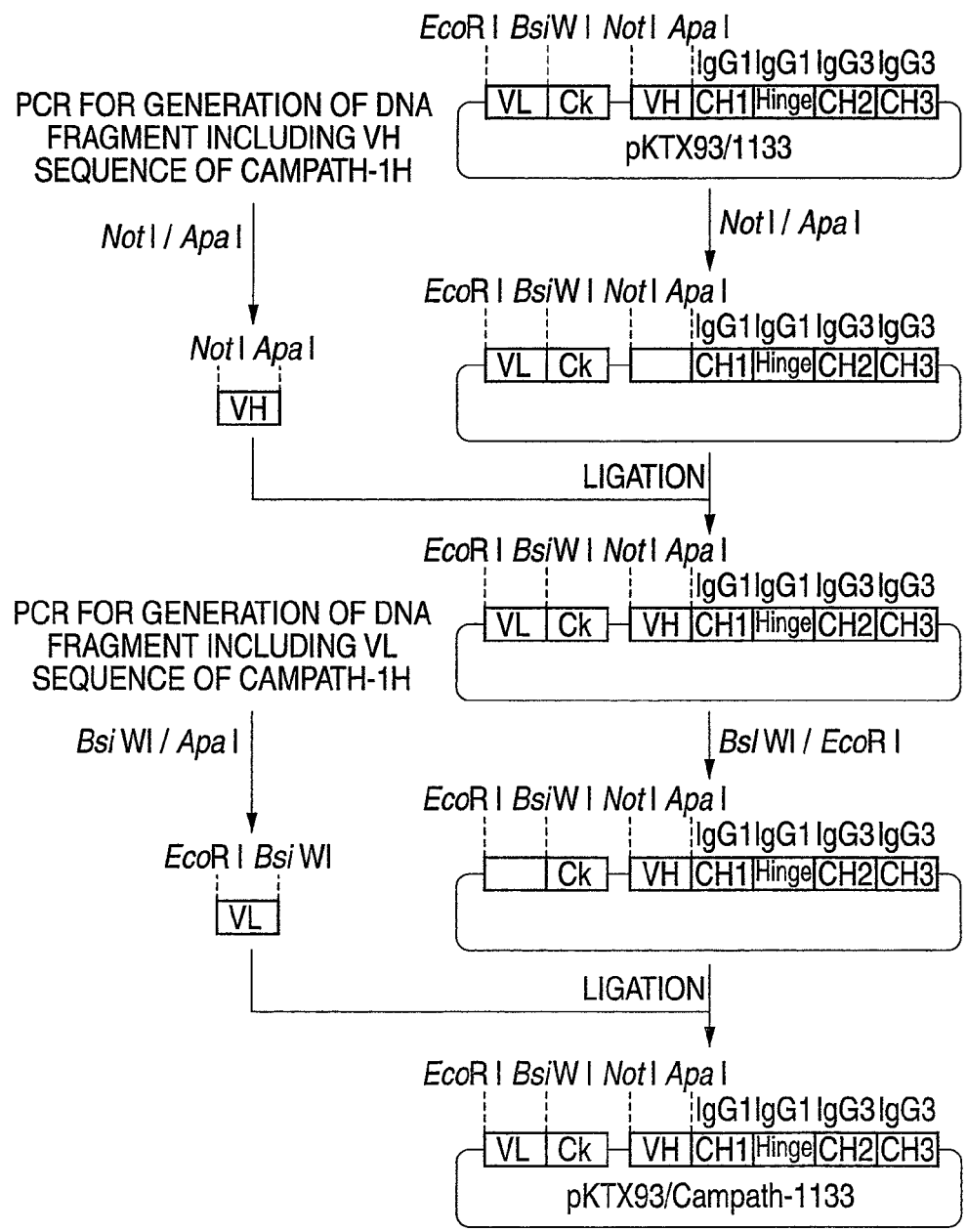
FIG. 27 shows construction steps of an expression vector plasmid of 1133-type anti-Campath domain-swapped antibody.

(1) Construction of Expression Vector Comprising the Nucleotide Sequence Encoding 1133-Type Anti-Campath Domain-Swapped Antibody An expression vector comprising the nucleotide sequence of a 1133-type anti-Campath domain-swapped antibody which specifically recognizes human Campath antigen (CD52), wherein among the amino acid sequences of the heavy chain constant region, CH1 and hinge are amino acid sequences of human IgG1, and CH2 and CH3 are amino acid sequences of human IgG3, was constructed by the procedure shown below (FIG. 27).

Firstly, the amino acid sequences and the nucleotide sequences of the heavy chain variable region (Accession: 579311) and the light chain variable region (Accession: S79307) of the humanized anti-Campath antibody Campath-1H were obtained from the data base of National Center of Biotechnology Information (NCBI). The amino acid sequence of the heavy chain variable region of the humanized anti-Campath antibody Campath-1H and the nucleotide sequence thereof are shown in SEQ ID NOs:58 and 59, respectively, and the amino acid sequence of the light chain variable region of the humanized anti-Campath antibody Campath-1H and the nucleotide sequence thereof are shown in SEQ ID NOs:60 and 61, respectively. Based on the sequence information, the amino acid sequence of the heavy chain of the 1133-type anti-Campath domain-swapped antibody represented by SEQ ID NO:62 containing sequences of the heavy chain variable region of the humanized anti-Campath antibody Campath-1H and the 1133-type heavy chain constant region, and the amino acid sequence of the light chain of the anti-Campath antibody represented by SEQ ID NO:63 containing sequences of the light chain variable region of the humanized anti-Campath antibody Campath-1H and the light chain constant region of the humanized antibody were designed.

Next, the nucleotide sequence represented by SEQ ID NO:64 was designed. The sequence is a nucleotide sequence in which a restriction enzyme NotI recognition sequence was added to the 5'-terminal side of the nucleotide sequence of the heavy chain variable region in the humanized anti-Campath antibody Campath-1H, represented by SEQ ID NO:59, and a restriction enzyme ApaI recognition sequence to the 3'-terminal side thereof. In addition, the nucleotide sequences represented by SEQ ID NOs:65, 66, 67 and 68 were designed based on the nucleotide sequence represented by SEQ ID NO:64. These sequences are nucleotide sequences designed by dividing the nucleotide sequence represented by SEQ ID NO:64 into four parts, in such a manner that mutually adjoining sequences have an overlapping sequence of approximately 20 bp and the sense chain and antisense chain are reciprocated.

In fact, each of synthetic oligo DNAs of the nucleotide sequences represented by SEQ ID NOs:65, 66, 67 and 68 was prepared (manufactured by FASMAC), and PCR was carried out using them. By preparing a reaction solution for PCR [0.02 unit/μl KOD+DNA Polymerase (manufactured by TOYOBO), 0.2 mM dNTPs, 1 mM magnesium chloride, 1/10 volume of 10-fold concentrated PCR Buffer (manufactured by TOYOBO, attached to the KOD DNA Polymerase)] in such a manner that the two synthetic oligo DNAs positioned at both terminals respectively became a final concentration of 0.5 μM and the other two synthetic oligo DNAs positioned inside thereof respectively became a final concentration of 0.1 μM, and PCR was carried out using a DNA thermal cycler GeneAmp PCR System 9700 (manufactured by Applied Biosystems) by heating at 94° C. for 4 minutes, followed by 25 cycles of 3 steps of reactions at 94° C. for 30 seconds, at 50° C. for 30 seconds and at 68° C. for 60 seconds. After completion of the PCR, the reaction solution was subjected to agarose gel electrophoresis, and a PCR product of about 480 bp was recovered using QIAquick™ Gel Extraction Kit (manufactured by QIAGEN). The thus recovered PCR product was digested with restriction enzymes NotI (manufactured by Takara Shuzo) and ApaI (manufactured by Takara Shuzo), and then the reaction solution was subjected to agarose gel electrophoresis, and a DNA fragment of about 450 bp was cleaved and purified using QIAquick™ Gel Extraction Kit (manufactured by QIAGEN). On the other hand, a DNA fragment of about 13 kbp was cleaved and purified by carrying out the same restriction enzyme treatment on the expression vector plasmid of 1133-type anti-CD20 domain-swapped antibody prepared in the item 2 of Example 2. After mixing these purified DNA fragments, a ligation reaction was carried out by adding Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that a 1133-type expression vector plasmid in which the heavy chain variable region was replaced by a nucleotide sequence encoding the heavy chain variable region of the humanized anti-Campath antibody Campath-1H was obtained.

Next, the nucleotide sequence represented by SEQ ID NO:69 was designed. The sequence is a nucleotide sequence in which a recognition sequence restricted by a restriction enzyme EcoRI was added to the 5'-terminal region of the nucleotide sequence of the light chain variable region in the humanized anti-Campath antibody Campath-1H represented by SEQ ID NO:61, and a recognition sequence restricted by a restriction enzyme BsiWI to the 3'-terminal region thereof. In addition, each of the nucleotide sequences represented by SEQ ID NOs:70, 71, 72 and 73 was designed based on the nucleotide sequence represented by SEQ ID NO:69. These sequences were nucleotide sequences designed by dividing the nucleotide sequence represented by SEQ ID NO:69 into four parts, in such a manner that mutually adjoining sequences have an overlapping sequence of approximately 20 bps and the sense chain and antisense chain were reciprocated. By carrying out PCR using four synthetic oligo DNA fragments represented by these nucleotide sequences, they were ligated via the overlapping sequence of mutually adjoining sequences to amplify a DNA fragment having the nucleotide sequence represented by SEQ ID NO:69.

In fact, each of synthetic oligo DNA fragments of the nucleotide sequences represented by SEQ ID NOs:70, 71, 72 and 73 were prepared (manufactured by FASMAC), and PCR was carried out using them. By preparing a reaction solution for PCR [0.02 unit/μl KOD+DNA Polymerase (manufactured by TOYOBO), 0.2 mM dNTPs, 1 mM magnesium chloride, 1/10 volume of 10-fold concentrated PCR Buffer (manufactured by TOYOBO, attached to the KOD DNA Polymerase)] in such a manner that the two synthetic oligo DNAs positioned at both terminals respectively became a final concentration of 0.5 μM and the other two synthetic oligo DNAs positioned inside thereof respectively became a final concentration of 0.1 μM, and PCR was carried out using a DNA thermal cycler GeneAmp PCR System 9700™ (manufactured by Applied Biosystems) by heating at 94° C. for 4 minutes, followed by 25 cycles of 3 steps of reactions at 94° C. for 30 seconds, at 50° C. for 30 seconds and at 68° C. for 60 seconds. After completion of the PCR reaction, the reaction solution was subjected to agarose gel electrophoresis, and a PCR product of about 420 bp was recovered using QIAquick™ Gel Extraction Kit (manufactured by QIAGEN). The thus recovered PCR product was digested with restriction enzymes EcoRI (manufactured by Takara Shuzo) and BsiWI (manufactured by TOYOBO), and then the reaction solution was subjected to agarose gel electrophoresis, and a DNA fragment of about 400 bp was cleaved and purified using QIAquick™ Gel Extraction Kit (manufactured by QIAGEN). On the other hand, a DNA fragment of about 13 kbp was cleaved and purified by carrying out the same restriction enzyme treatment on the 1133-type expression vector plasmid in which the heavy chain variable region was replaced by a nucleotide sequence encoding the heavy chain variable region of the humanized anti-Campath antibody Campath-1H, prepared in this item. After mixing these purified DNA fragments, a ligation reaction was carried out by adding Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that expression vector plasmid for 1133-type anti-Campath antibody, pKTX93/Campath1H-1133 was obtained.

Figure 28:
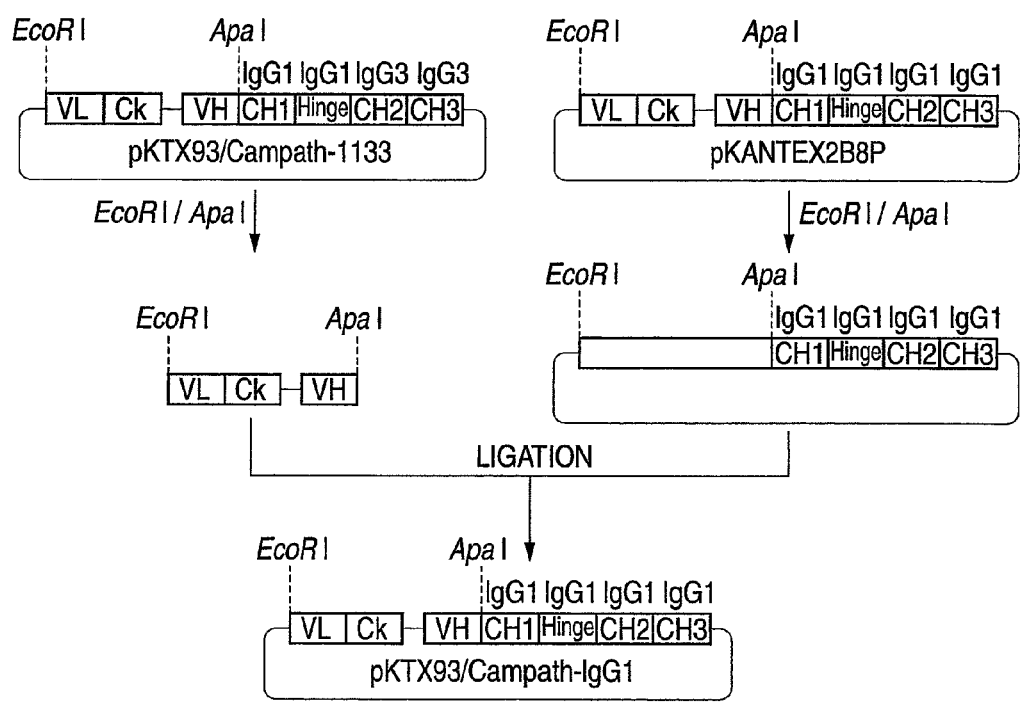
FIG. 28 shows construction steps of an expression vector plasmid of anti-Campath human IgG1 antibody.

(2) Construction of Expression Vector Comprising the Nucleotide Sequence Encoding Human IgG Anti-Campath Antibody An expression vector comprising the nucleotide sequence of an anti-Campath human IgG1 antibody which specifically recognizes a human Campath antigen (CD52), wherein the heavy chain constant region was the amino acid sequence of human IgG1, was constructed by the procedure shown bellow (FIG. 28).

The expression vector plasmid for 1133-type anti-Campath antibody, pKTX93/Campath1H-1133 prepared in this item was digested with restriction enzymes EcoRI (manufactured by Takara Shuzo) and ApaI (manufactured by Takara Shuzo), and then the reaction solution was subjected to agarose gel electrophoresis, and a DNA fragment of about 3,300 bp was cleaved and purified using QIAquick™ Gel Extraction Kit (manufactured by QIAGEN). On the other hand, a DNA fragment of about 10 kbp was cleaved and purified by carrying out the same restriction enzyme treatment on the expression vector plasmid for anti-CD20 human IgG1 chimeric antibody, pKANTEX2B8P. After mixing these purified DNA fragments, a ligation reaction was carried out by adding Ligation High solution (manufactured by TOYOBO), and *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that expression vector plasmid for anti-Campath human IgG1 antibody, pKTX93/Campath1H-IgG1 was obtained.

Figure 29:
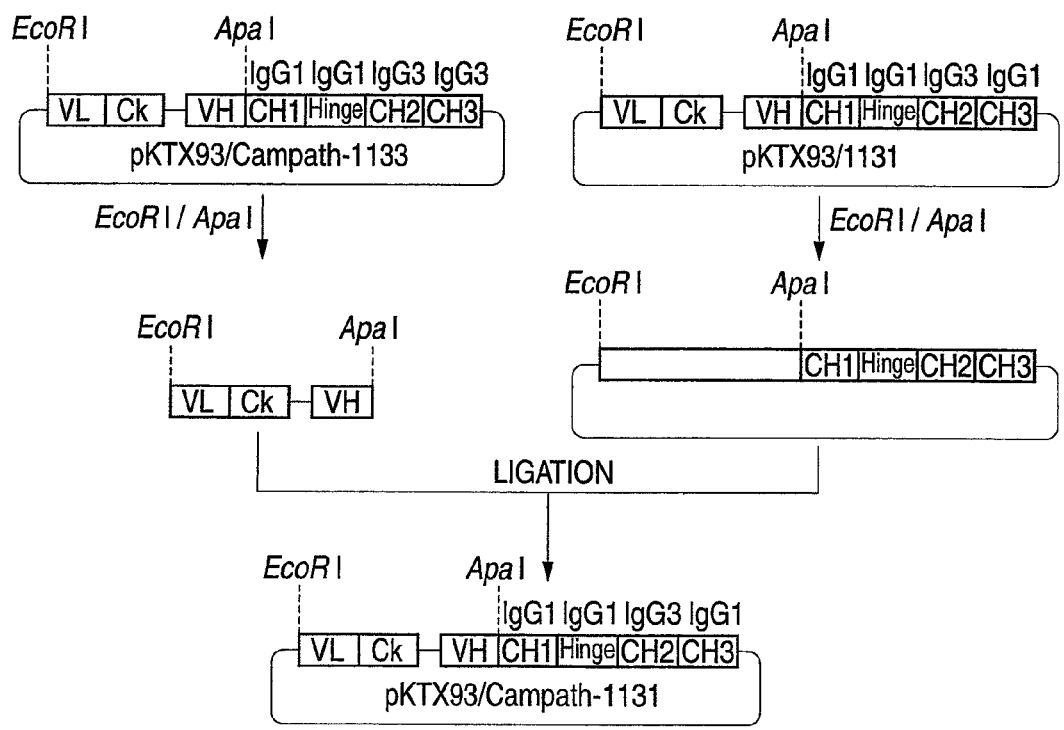
FIG. 29 shows construction steps of an expression vector plasmid of 1131-type anti-Campath domain-swapped antibody.

(3) Construction of Expression Vector Comprising the Nucleotide Sequence Encoding 1133-Type Anti-Campath Antibody An expression vector comprising the nucleotide sequence of a human 1133-type anti-Campath antibody which specifically recognizes a human Campath antigen (CD52), wherein among the amino acid sequences of the heavy chain constant region, CH1 and hinge are the amino acid sequences of human IgG1, CH2 is the amino acid sequence of human IgG3 and CH3 is the amino acid sequence of human IgG1, was constructed by the procedure shown bellow (FIG. 29).

The expression vector plasmid for 1133-type anti-Campath antibody, pKTX93/Campath1H-1133 prepared in this item was digested with restriction enzymes EcoRI (manufactured by Takara Shuzo) and ApaI (manufactured by Takara Shuzo), and then the reaction solution was subjected to agarose gel electrophoresis, and a DNA fragment of about 3,300 bp was cleaved and purified using QIAquick™ Gel Extraction Kit (manufactured by QIAGEN). On the other hand, a DNA fragment of about 10 kbp was cleaved and purified by carrying out the same restriction enzyme treatment on the expression vector plasmid for 1131-type anti-CD20 antibody, pKTX93/1131 prepared in the item 1 of Example 3. After mixing these purified DNA fragments, a ligation reaction was carried out by adding Ligation High solution (manufactured by TOYOBO), and the *Escherichia coli* XL1-BLUE MRF' (manufactured by Stratagene) was transformed using the reaction solution. Each plasmid DNA was prepared from the thus obtained transformant clones and allowed to react using Big Dye Terminator Cycle™ Sequencing Kit v3.1 (manufactured by Applied Biosystems) in accordance with the instructions attached thereto, and then the nucleotide sequence of the DNA inserted into each plasmid was analyzed by a DNA sequencer ABI PRISM 3700™ DNA Analyzer of the same company to confirm that expression vector plasmid for 1131-type anti-Campath domain-swapped antibody, pKTX93/Campath1H-1131 was obtained.

2. Stable Expression of Anti-Campath Human IgG1 Antibody, 1133-Type Anti-Campath Domain-Swapped Antibody and 1131-Type Anti-Campath Domain-Swapped Antibody in Animal Cell Each of the expression vectors for the anti-Campath human IgG1 antibody, the 1133-type anti-Campath domain-swapped antibody and the 1131-type anti-Campath domain-swapped antibody prepared in the item 1 of this Example was introduced into the host cell CHO/FUT8$^{-/-}$ described in the item 3 of Example 1, and a cell capable of stably producing the anti-Campath human IgG1 antibody, the 1133-type anti-Campath domain-swapped antibody or the 1131-type anti-Campath domain-swapped antibody was prepared in the same manner as in the item 3 of Example 1.

3. Purification of Anti-Campath Human IgG1 Antibody, 1133-Type Anti-Campath Domain-Swapped Antibody and 1131-Type Anti-Campath Domain-Swapped Antibody Each of the transformants capable of expressing the anti-Campath human IgG1 antibody, the 1133-type anti-Campath domain-swapped antibody or the 1131-type anti-Campath domain-swapped antibody, obtained in the item 2 of this Example, was cultured and purified in the same manner as in the item 5 of Example 1. Corresponding expression vectors, host cells and names of the purified antibodies of each of the modified antibodies are shown in Table 9.

TABLE 9

| Expression vector | Host cell | Purified antibody (name) |
| --- | --- | --- |
| pKTX93/Campath1H-IgG1 | Ms705 | Campath1H-IgG1 |
| pKTX93/Campath1H-1133 | Ms705 | Campath1H-1133 |
| pKTX93/Campath1H-1131 | Ms705 | Campath1H-1131 |

4. Evaluation of the Purification Degree of Various Anti-Campath Antibodies by SDS-PAGE In order to evaluate purification degree of the purified samples of the various modified antibodies obtained in the item 3 of this Example, SDS-PAGE was carried out in the same manner as in the item 6 of Example 1 to thereby confirm that the desired IgG molecule constituted by the respective H chain and L chain was contained at a sufficient ratio in each of the purified modified antibody samples obtained in the item 3 of this Example.

Example 10

Measurement of the CDC Activity of Anti-Campath Human IgG1 Antibody, 1133-Type Anti-Campath Domain-Swapped Antibody and 1131-Type Anti-Campath Domain-Swapped Antibody Using the purified samples of the various anti-Campath antibodies Campath1H-IgG1, Campath1H-1133 and Campath1H-1131 obtained in the item 3 of Example 9, their in vitro CDC activity to the Campath antigen-positive CLL cell lines MEC-1, MEC-2 and EHEB was measured. When the test was carried out in the same manner as in Example 8, Campath1H-1133 and Campath1H-1131 showed higher CDC activity than that of Campath1H-IgG for all of the cell lines MEC-1, MEC-2 and EHEB.

The present invention provides a recombinant antibody composition having higher complement-dependent cytotoxic activity than a human IgG1 antibody and a human IgG3 antibody, wherein a polypeptide comprising a CH2 domain in the Fc region of a human IgG1 antibody is replaced by a polypeptide comprising an amino acid sequence which corresponds to the same position of a human IgG3 antibody indicated by the EU index as in Kabat, et al., a DNA encoding an antibody molecule contained in the recombinant composition or a heavy chain constant region of the antibody molecule; a transformant obtainable by introducing the DNA into a host cell; a process for producing the recombinant antibody composition using the transformant; and a medicament comprising the recombinant antibody composition as an active ingredient While the invention has been described in detail and with reference to specific embodiments thereof, it will be apparent to one skill in the art that various changes and modifications can be made therein without departing from the spirit and scope thereof.

What is claimed is:

1. A recombinant antibody composition comprising recombinant antibodies, said recombinant antibodies having greater complement-dependent cytotoxic activity than human IgG1 and human IgG3 antibodies of the same binding specificity under the same conditions, said recombinant antibodies comprising a region containing a CH1, a hinge, a CH2 and a CH3 domain, said region comprising the amino acid sequence of SEQ ID NO: 76 in which at least the first 110 amino acids commencing at residue 114 of SEQ ID NO: 76 are replaced with the corresponding residues from SEQ ID NO: 78, and in which residues 1-113 of SEQ ID NO: 76 in said region are not replaced with the corresponding residues from SEQ ID NO: 78.

2. The recombinant antibody composition according to claim 1, wherein said recombinant antibodies have complex type N-glycoside-linked sugar chains in the Fc region, wherein the ratio of sugar chains in which fucose is not bound to N-acetylglucosamine in the reducing terminal of the sugar chains among the total complex type N-glycoside-linked sugar chains which bind to the Fc region contained in the composition is 20% or more.

3. The recombinant antibody composition according to claim 1, wherein said recombinant antibodies have complex type N-glycoside-linked sugar chains in the Fc region, wherein the complex type N-glycoside-linked sugar chains bound to the Fc region of the antibody are sugar chains in which fucose is not bound to N-acetylglucosamine in the reducing terminal in the sugar chains.

4. A medicament comprising the recombinant antibody composition described in claim 1 as an active ingredient.

5. A recombinant antibody composition comprising recombinant antibodies, said recombinant antibodies having greater complement-dependent cytotoxic activity than human IgG1 and human IgG3 antibodies of the same binding specificity under the same conditions, said recombinant antibodies comprising a region containing a CH1, a hinge, a CH2 and a CH3 domain, said region comprising the amino acid sequence of SEQ ID NO: 76 in which residues selected from the following (1)-(8) are replaced with the corresponding residues from SEQ ID NO: 78:

(1) residues 114-223 of SEQ ID NO: 76;
(2) residues 114-239 of SEQ ID NO: 76;
(3) residues 114-241 of SEQ ID NO: 76;
(4) residues 114-267 of SEQ ID NO: 76;
(5) residues 114-275 of SEQ ID NO: 76;
(6) residues 114-280 of SEQ ID NO: 76;
(7) residues 114-305 of SEQ ID NO: 76; and
(8) residues 114-317 and residues 319-330 of SEQ ID NO: 76.

6. The recombinant antibody composition of claim 1 or 5, wherein said recombinant antibodies have an activity of binding protein A substantially equal to the binding of protein A to IgG1.

* * * * *

SEQUENCE LISTING

```
<160> NUMBER OF SEQ ID NOS: 91

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
caaaggtacc caagggccca tcggtcttcc                                      30

<210> SEQ ID NO 2
<211> LENGTH: 45
<212> TYPE: DNA
<213> ORGANISM: Artificial Sequence
<220> FEATURE:
<223> OTHER INFORMATION: Synthetic DNA

<400> SEQUENCE: 2
gtttggatcc tcgcgagtcg cactcattta cccggagaca gggag                     45

<210> SEQ ID NO 3
```

<211> LENGTH: 1130
<212> TYPE: DNA
<213> ORGANISM: Homo sapiens

<400> SEQUENCE: 3

```
cttccaccaa gggcccatcg gtcttccccc tggcgccctg ctccaggagc acctctgggg    60
gcacagcggc cctgggctgc ctggtcaagg actacttccc cgaaccggtg acggtgtcgt   120
ggaactcagg cgccctgacc agcggcgtgc acaccttccc ggctgtccta cagtcctcag   180
gactctactc cctcagcagc gtggtgaccg tgccctccag cagcttgggc acccagacct   240
acacctgcaa cgtgaatcac aagcccagca acaccaaggt ggacaagaga gttgagctca   300
aaaccccact tggtgacaca actcacacat gcccacggtg cccagagccc aaatcttgtg   360
acacacctcc cccgtgccca cggtgcccag agcccaaatc ttgtgacaca cctcccccat   420
gcccacggtg cccagagccc aaatcttgtg acacacctcc cccatgccca cggtgcccag   480
cacctgaact cctgggagga ccgtcagtct cctcttcccc cccaaaaccc aaggataccc   540
ttatgatttc ccggacccct gaggtcacgt gcgtggtggt ggacgtgagc cacgaagacc   600
ccgaggtcca gttcaagtgg tacgtggacg gcgtggaggt gcataatgcc aagacaaagc   660
cgcgggagga gcagttcaac agcacgttcc gtgtggtcag cgtcctcacc gtcctgcacc   720
aggactggct gaacggcaag gagtacaagt gcaaggtctc caacaaagcc ctcccagccc   780
ccatcgagaa aaccatctcc aaaaccaaag gacagccccg agaaccacag gtgtacaccc   840
tgcccccatc ccgggaggag atgaccaaga accaggtcag cctgacctgc ctggtcaaag   900
gcttctaccc cagcgacatc gccgtggagt gggagagcaa cgggcagccg gagaacaact   960
acaacaccac gcctcccatg ctggactccg acggctcctt cttcctctac agcaagctca  1020
ccgtggacaa gagcaggtgg cagcagggga acatcttctc atgctccgtg atgcatgagg  1080
ctctgcacaa ccgcttcacg cagaagagcc tctccctgtc tccgggtaaa             1130
```

<210> SEQ ID NO 4
<211> LENGTH: 454
<212> TYPE: DNA
<213> ORGANISM: Artificial Sequence
<220> FEATURE:
<223> OTHER INFORMATION: Synthetic DNA

<400> SEQUENCE: 4

```
gggggtaccg ggcccatcgg tcttccccct ggcgccctgc tccaggagca cctctggggg    60
cacagcggcc ctgggctgcc tggtcaagga ctacttcccc gaaccggtga cggtgtcgtg   120
gaactcaggc gccctgacca gcggcgtgca caccttcccg gctgtcctac agtcctcagg   180
actctactcc ctcagcagcg tggtgaccgt gccctccagc agcttgggca cccagaccta   240
cacctgcaac gtgaatcaca agcccagcaa caccaaggtg gacaagaaag ttgagcccaa   300
atcttgtgac aaaactcaca catgcccacc gtgcccagca cctgaactcc tggggggacc   360
gtcagtcttc ctcttccccc caaaacccaa ggacaccctc atgatctccc ggacccctga   420
ggtcacatgc gtggtggtgg acgtgaagct tggg                               454
```

<210> SEQ ID NO 5
<211> LENGTH: 129
<212> TYPE: DNA
<213> ORGANISM: Artificial Sequence
<220> FEATURE:
<223> OTHER INFORMATION: Synthetic DNA

<400> SEQUENCE: 5 ggggtaccg ggcccatcgg tcttccccct ggcgccctgc tccaggagca cctctggggg      60
cacagcggcc ctgggctgcc tggtcaagga ctacttcccc gaaccggtga cggtgtcgtg     120
gaactcagg                                                             129

<210> SEQ ID NO 6
<211> LENGTH: 127
<212> TYPE: DNA
<213> ORGANISM: Artificial Sequence
<220> FEATURE:
<223> OTHER INFORMATION: Synthetic DNA

<400> SEQUENCE: 6
ggtctgggtg cccaagctgc tggagggcac ggtcaccacg ctgctgaggg agtagagtcc      60
tgaggactgt aggacagccg ggaaggtgtg cacgccgctg gtcagggcgc ctgagttcca     120
cgacacc                                                               127

<210> SEQ ID NO 7
<211> LENGTH: 121
<212> TYPE: DNA
<213> ORGANISM: Artificial Sequence
<220> FEATURE:
<223> OTHER INFORMATION: Synthetic DNA

<400> SEQUENCE: 7
gcttgggcac ccagacctac acctgcaacg tgaatcacaa gcccagcaac accaaggtgg      60
acaagaaagt tgagcccaaa tcttgtgaca aaactcacac atgcccaccg tgcccagcac     120
c                                                                     121

<210> SEQ ID NO 8
<211> LENGTH: 129
<212> TYPE: DNA
<213> ORGANISM: Artificial Sequence
<220> FEATURE:
<223> OTHER INFORMATION: Synthetic DNA

<400> SEQUENCE: 8
cccaagcttc acgtccacca ccacgcatgt gacctcaggg gtccgggaga tcatgagggt      60
gtccttgggt tttgggggga agaggaagac tgacggtccc cccaggagtt caggtgctgg     120
gcacggtgg                                                             129

<210> SEQ ID NO 9
<211> LENGTH: 595
<212> TYPE: DNA
<213> ORGANISM: Artificial Sequence
<220> FEATURE:
<223> OTHER INFORMATION: Synthetic DNA

<400> SEQUENCE: 9 ggggtaccg ggcccatcgg tcttccccct ggcaccctcc tccaagagca cctctggggg      60
cacagcggcc ctgggctgcc tggtcaagga ctacttcccc gaaccggtga cggtgtcgtg     120
gaactcaggc gccctgacca gcggcgtgca caccttcccg gctgtcctac agtcctcagg    180
actctactcc ctcagcagcg tggtgaccgt gccctccagc agcttgggca cccagaccta    240
catctgcaac gtgaatcaca agcccagcaa caccaaggtg gacaagagag ttgagctcaa    300
aacacctctc ggagacacca cacatacttg tcctagatgc ccagagccca atcttgtga    360 cacacctccc ccgtgcccac ggtgcccaga gcccaaatct tgtgacacac ctccccccatg    420

```
cccacggtgc ccagagccca atcttgtga cacacctcca ccctgtccca gatgtcctgc      480
acctgagctc ctgggaggac cgtcagtctt cctcttcccc ccaaaaccca aggatacccct    540 tatgatttcc cggacccctg aggtcacgtg cgtggtggtg gacgtgaagc ttggg          595
```

```
<210> SEQ ID NO 10
<211> LENGTH: 19
<212> TYPE: DNA
<213> ORGANISM: Artificial Sequence
<220> FEATURE:
<223> OTHER INFORMATION: Synthetic DNA

<400> SEQUENCE: 10
gggggtaccg ggcccatcg                                                   19
```

```
<210> SEQ ID NO 11
<211> LENGTH: 139
<212> TYPE: DNA
<213> ORGANISM: Artificial Sequence
<220> FEATURE:
<223> OTHER INFORMATION: Synthetic DNA

<400> SEQUENCE: 11
ggtcagggcg cctgagttcc acgacaccgt caccggttcg gggaagtagt ccttgaccag      60
gcagcccagg gccgctgtgc ccccagaggt gctcttggag gagggtgcca gggggaagac    120
cgatgggccc ggtaccccc                                                  139
```

```
<210> SEQ ID NO 12
<211> LENGTH: 119
<212> TYPE: DNA
<213> ORGANISM: Artificial Sequence
<220> FEATURE:
<223> OTHER INFORMATION: Synthetic DNA

<400> SEQUENCE: 12
ggaactcagg cgccctgacc agcggcgtgc acaccttccc ggctgtccta cagtcctcag      60
gactctactc cctcagcagc gtggtgaccg tgccctccag cagcttgggc acccagacc      119
```

```
<210> SEQ ID NO 13
<211> LENGTH: 122
<212> TYPE: DNA
<213> ORGANISM: Artificial Sequence
<220> FEATURE:
<223> OTHER INFORMATION: Synthetic DNA

<400> SEQUENCE: 13
gcatctagga caagtatgtg tggtgtctcc gagaggtgtt ttgagctcaa ctctcttgtc      60
caccttggtg ttgctgggct tgtgattcac gttgcagatg taggtctggg tgcccaagct    120
gc                                                                    122
```

```
<210> SEQ ID NO 14
<211> LENGTH: 171
<212> TYPE: DNA
<213> ORGANISM: Artificial Sequence
<220> FEATURE:
<223> OTHER INFORMATION: Synthetic DNA

<400> SEQUENCE: 14
ccacacatac ttgtcctaga tgcccagagc ccaaatcttg tgacacacct cccccgtgcc      60
cacggtgccc agagcccaaa tcttgtgaca cacctccccc atgcccacgg tgcccagagc    120
ccaaatcttg tgacacacct ccaccctgtc ccagatgtcc tgcacctgag c              171
```

<210> SEQ ID NO 15
<211> LENGTH: 128
<212> TYPE: DNA
<213> ORGANISM: Artificial Sequence
<220> FEATURE:
<223> OTHER INFORMATION: Synthetic DNA

<400> SEQUENCE: 15

```
cccaagcttc acgtccacca ccacgcacgt gacctcaggg gtccgggaaa tcataagggt     60
atccttgggt tttgggggga agaggaagac tgacggtcct cccaggagct caggtgcagg    120
acatctgg                                                             128
```

<210> SEQ ID NO 16
<211> LENGTH: 330
<212> TYPE: PRT
<213> ORGANISM: Artificial Sequence
<220> FEATURE:
<223> OTHER INFORMATION: Synthetic Peptide

<400> SEQUENCE: 16

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
```

```
                   275                 280                 285
Leu Tyr Ser Lys Leu Thr Val Asp Lys Ser Arg Trp Gln Gln Gly Asn
            290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 17
<211> LENGTH: 990
<212> TYPE: DNA
<213> ORGANISM: Artificial Sequence
<220> FEATURE:
<223> OTHER INFORMATION: Synthetic DNA

<400> SEQUENCE: 17
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ccgaggtcca gttcaagtgg     480
tacgtggacg gcgtggaggt gcataatgcc aagacaaagc cgcgggagga gcagttcaac     540
agcacgttcc gtgtggtcag cgtcctcacc gtcctgcacc aggactggct gaacggcaag     600
gagtacaagt gcaaggtctc caacaaagcc ctcccagccc ccatcgagaa aaccatctcc     660
aaaaccaaag gacagccccg agaaccacag gtgtacaccc tgcccccatc ccgggaggag     720
atgaccaaga accaggtcag cctgacctgc ctggtcaaag gcttctaccc cagcgacatc     780
gccgtggagt gggagagcag cgggcagccg gagaacaact acaacaccac gcctcccatg     840
ctggactccg acggctcctt cttcctctac agcaagctca ccgtggacaa gagcaggtgg     900
cagcagggga acatcttctc atgctccgtg atgcatgagg ctctgcacaa ccgcttcacg     960
cagaagagcc tctccctgtc tccgggtaaa                                      990

<210> SEQ ID NO 18
<211> LENGTH: 1504
<212> TYPE: DNA
<213> ORGANISM: Cricetulus griseus
<220> FEATURE:
<221> NAME/KEY: CDS
<222> LOCATION: (1)..(1119)

<400> SEQUENCE: 18 atg gct cac gct ccc gct agc tgc ccg agc tcc agg aac tct ggg gac        48
Met Ala His Ala Pro Ala Ser Cys Pro Ser Ser Arg Asn Ser Gly Asp
  1               5                  10                  15 ggc gat aag ggc aag ccc agg aag gtg gcg ctc atc acg ggc atc acc        96
Gly Asp Lys Gly Lys Pro Arg Lys Val Ala Leu Ile Thr Gly Ile Thr
             20                  25                  30 ggc cag gat ggc tca tac ttg gca gaa ttc ctg ctg gag aaa gga tac       144
Gly Gln Asp Gly Ser Tyr Leu Ala Glu Phe Leu Leu Glu Lys Gly Tyr
         35                  40                  45 gag gtt cat gga att gta cgg cga tcc agt tca ttt aat aca ggt cga       192
```

```
                Glu Val His Gly Ile Val Arg Arg Ser Ser Ser Phe Asn Thr Gly Arg
                 50                  55                  60 att gaa cat tta tat aag aat cca cag gct cat att gaa gga aac atg        240
Ile Glu His Leu Tyr Lys Asn Pro Gln Ala His Ile Glu Gly Asn Met
 65                  70                  75                  80 aag ttg cac tat ggt gac ctc acc gac agc acc tgc cta gta aaa atc        288
Lys Leu His Tyr Gly Asp Leu Thr Asp Ser Thr Cys Leu Val Lys Ile
                     85                  90                  95 atc aat gaa gtc aaa cct aca gag atc tac aat ctt ggt gcc cag agc        336
Ile Asn Glu Val Lys Pro Thr Glu Ile Tyr Asn Leu Gly Ala Gln Ser
                100                 105                 110 cat gtc aag att tcc ttt gac tta gca gag tac act gca gat gtt gat        384
His Val Lys Ile Ser Phe Asp Leu Ala Glu Tyr Thr Ala Asp Val Asp
            115                 120                 125 gga gtt ggc acc ttg cgg ctt ctg gat gca att aag act tgt ggc ctt        432
Gly Val Gly Thr Leu Arg Leu Leu Asp Ala Ile Lys Thr Cys Gly Leu
        130                 135                 140 ata aat tct gtg aag ttc tac cag gcc tca act agt gaa ctg tat gga        480
Ile Asn Ser Val Lys Phe Tyr Gln Ala Ser Thr Ser Glu Leu Tyr Gly
145                 150                 155                 160 aaa gtg caa gaa ata ccc cag aaa gag acc acc cct ttc tat cca agg        528
Lys Val Gln Glu Ile Pro Gln Lys Glu Thr Thr Pro Phe Tyr Pro Arg
                165                 170                 175 tcg ccc tat gga gca gcc aaa ctt tat gcc tat tgg att gta gtg aac        576
Ser Pro Tyr Gly Ala Ala Lys Leu Tyr Ala Tyr Trp Ile Val Val Asn
                180                 185                 190 ttt cga gag gct tat aat ctc ttt gcg gtg aac ggc att ctc ttc aat        624
Phe Arg Glu Ala Tyr Asn Leu Phe Ala Val Asn Gly Ile Leu Phe Asn
            195                 200                 205 cat gag agt cct aga aga gga gct aat ttt gtt act cga aaa att agc        672
His Glu Ser Pro Arg Arg Gly Ala Asn Phe Val Thr Arg Lys Ile Ser
        210                 215                 220 cgg tca gta gct aag att tac ctt gga caa ctg gaa tgt ttc agt ttg        720
Arg Ser Val Ala Lys Ile Tyr Leu Gly Gln Leu Glu Cys Phe Ser Leu
225                 230                 235                 240 gga aat ctg gac gcc aaa cga gac tgg ggc cat gcc aag gac tat gtc        768
Gly Asn Leu Asp Ala Lys Arg Asp Trp Gly His Ala Lys Asp Tyr Val
                245                 250                 255 gag gct atg tgg ctg atg tta caa aat gat gaa cca gag gac ttt gtc        816
Glu Ala Met Trp Leu Met Leu Gln Asn Asp Glu Pro Glu Asp Phe Val
                260                 265                 270 ata gct act ggg gaa gtt cat agt gtc cgt gaa ttt gtt gag aaa tca        864
Ile Ala Thr Gly Glu Val His Ser Val Arg Glu Phe Val Glu Lys Ser
            275                 280                 285 ttc atg cac att gga aag acc att gtg tgg gaa gga aag aat gaa aat        912
Phe Met His Ile Gly Lys Thr Ile Val Trp Glu Gly Lys Asn Glu Asn
        290                 295                 300 gaa gtg ggc aga tgt aaa gag acc ggc aaa att cat gtg act gtg gat        960
Glu Val Gly Arg Cys Lys Glu Thr Gly Lys Ile His Val Thr Val Asp
305                 310                 315                 320 ctg aaa tac tac cga cca act gaa gtg gac ttc ctg cag gga gac tgc       1008
Leu Lys Tyr Tyr Arg Pro Thr Glu Val Asp Phe Leu Gln Gly Asp Cys
                325                 330                 335 tcc aag gcg cag cag aaa ctg aac tgg aag ccc cgc gtt gcc ttt gac       1056
Ser Lys Ala Gln Gln Lys Leu Asn Trp Lys Pro Arg Val Ala Phe Asp
                340                 345                 350 gag ctg gtg agg gag atg gtg caa gcc gat gtg gag ctc atg aga acc       1104
Glu Leu Val Arg Glu Met Val Gln Ala Asp Val Glu Leu Met Arg Thr
            355                 360                 365
```

```
aac ccc aac gcc tga gcacctctac aaaaaaattc gcgagacatg gactatggtg    1159
Asn Pro Asn Ala
    370 cagagccagc caaccagagt ccagccactc ctgagaccat cgaccataaa ccctcgactg    1219 cctgtgtcgt ccccacagct aagagctggg ccacaggttt gtgggcacca ggacggggac    1279 actccagagc taaggccact tcgcttttgt caaaggctcc tctcaatgat tttgggaaat    1339 caagaagttt aaaatcacat actcatttta cttgaaatta tgtcactaga caacttaaat    1399 ttttgagtct tgagattgtt tttctctttt cttattaaat gatctttcta tgacccagca    1459 aaaaaaaaaa aaaaaaggga tataaaaaaa aaaaaaaaaa aaaaa                   1504
```

<210> SEQ ID NO 19
<211> LENGTH: 372
<212> TYPE: PRT
<213> ORGANISM: Cricetulus griseus

<400> SEQUENCE: 19

```
Met Ala His Ala Pro Ala Ser Cys Pro Ser Ser Arg Asn Ser Gly Asp
1               5                   10                  15

Gly Asp Lys Gly Lys Pro Arg Lys Val Ala Leu Ile Thr Gly Ile Thr
                20                  25                  30

Gly Gln Asp Gly Ser Tyr Leu Ala Glu Phe Leu Leu Glu Lys Gly Tyr
            35                  40                  45

Glu Val His Gly Ile Val Arg Arg Ser Ser Ser Phe Asn Thr Gly Arg
        50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Ile Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Met His Ile Gly Lys Thr Ile Val Trp Glu Gly Lys Asn Glu Asn
```

Glu Val Gly Arg Cys Lys Glu Thr Gly Lys Ile His Val Thr Val Asp
305                 310                 315                 320

Leu Lys Tyr Tyr Arg Pro Thr Glu Val Asp Phe Leu Gln Gly Asp Cys
                325                 330                 335

Ser Lys Ala Gln Gln Lys Leu Asn Trp Lys Pro Arg Val Ala Phe Asp
            340                 345                 350

Glu Leu Val Arg Glu Met Val Gln Ala Asp Val Glu Leu Met Arg Thr
        355                 360                 365

Asn Pro Asn Ala
    370

<210> SEQ ID NO 20
<211> LENGTH: 1316
<212> TYPE: DNA
<213> ORGANISM: Cricetulus griseus

<400> SEQUENCE: 20

| | | | | | |
|---|---|---|---|---|---|
| gccccgcccc | ctccacctgg | accgagagta | gctggagaat | tgtgcaccgg | aagtagctct | 60 |
| tggactggtg | aaccctgcg | caggtgcagc | aacaatgggt | gagccccagg | gatccaggag | 120 |
| gatcctagtg | acaggggggct | ctggactggt | gggcagagct | atccagaagg | tggtcgcaga | 180 |
| tggcgctggc | ttacccggag | aggaatgggt | gtttgtctcc | tccaaagatg | cagatctgac | 240 |
| ggatgcagca | caaacccaag | ccctgttcca | gaaggtacag | cccacccatg | tcatccatct | 300 |
| tgctgcaatg | gtaggaggcc | ttttccggaa | tatcaaatac | aacttggatt | tctggaggaa | 360 |
| gaatgtgcac | atcaatgaca | acgtcctgca | ctcagctttc | gaggtgggca | ctcgcaaggt | 420 |
| ggtctcctgc | ctgtccacct | gtatcttccc | tgacaagacc | acctatccta | ttgatgaaac | 480 |
| aatgatccac | aatggtccac | cccacagcag | caattttggg | tactcgtatg | ccaagaggat | 540 |
| gattgacgtg | cagaacaggg | cctacttcca | gcagcatggc | tgcaccttca | ctgctgtcat | 600 |
| ccctaccaat | gtctttggac | tcatgacaa | cttcaacatt | gaagatggcc | atgtgctgcc | 660 |
| tggcctcatc | cataaggtgc | atctggccaa | gagtaatggt | tcagccttga | ctgtttgggg | 720 |
| tacagggaaa | ccacggaggc | agttcatcta | ctcactggac | ctagccggc | tcttcatctg | 780 |
| ggtcctgcgg | gagtacaatg | aagttgagcc | catcatcctc | tcagtgggcg | aggaagatga | 840 |
| agtctccatt | aaggaggcag | ctgaggctgt | agtggaggcc | atggacttct | gtggggaagt | 900 |
| cacttttgat | tcaacaaagt | cagatgggca | gtataagaag | acagccagca | atggcaagct | 960 |
| tcgggcctac | ttgcctgatt | tccgtttcac | acccttcaag | caggctgtga | aggagacctg | 1020 |
| tgcctggttc | accgacaact | atgagcaggc | ccggaagtga | agcatgggac | aagcgggtgc | 1080 |
| tcagctggca | atgcccagtc | agtaggctgc | agtctcatca | tttgcttgtc | aagaactgag | 1140 |
| gacagtatcc | agcaacctga | ccacatgct | ggtctctctg | ccaggggggct | tcatgcagcc | 1200 |
| atccagtagg | gccatgtttt | gtccatcctc | ggggggaaggc | cagaccaaca | ccttgtttgt | 1260 |
| ctgcttctgc | cccaacctca | gtgcatccat | gctggtcctg | ctgtcccttg | tctaga | 1316 |

<210> SEQ ID NO 21
<211> LENGTH: 321
<212> TYPE: PRT
<213> ORGANISM: Cricetulus griseus

<400> SEQUENCE: 21

Met Gly Glu Pro Gln Gly Ser Arg Arg Ile Leu Val Thr Gly Gly Ser
1               5                   10                  15

```
Gly Leu Val Gly Arg Ala Ile Gln Lys Val Val Ala Asp Gly Ala Gly
             20                  25                  30

Leu Pro Gly Glu Glu Trp Val Phe Val Ser Ser Lys Asp Ala Asp Leu
         35                  40                  45

Thr Asp Ala Ala Gln Thr Gln Ala Leu Phe Gln Lys Val Gln Pro Thr
     50                  55                  60

His Val Ile His Leu Ala Ala Met Val Gly Gly Leu Phe Arg Asn Ile
 65                  70                  75                  80

Lys Tyr Asn Leu Asp Phe Trp Arg Lys Asn Val His Ile Asn Asp Asn
                 85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Asp Glu Val Ser Ile Lys Glu Ala Ala
                245                 250                 255

Glu Ala Val Val Glu Ala Met Asp Phe Cys Gly Glu Val Thr Phe Asp
                260                 265                 270

Ser Thr Lys Ser Asp Gly Gln Tyr Lys Lys Thr Ala Ser Asn Gly Lys
            275                 280                 285

Leu Arg Ala Tyr Leu Pro Asp Phe Arg Phe Thr Pro Phe Lys Gln Ala
        290                 295                 300

Val Lys Glu Thr Cys Ala Trp Phe Thr Asp Asn Tyr Glu Gln Ala Arg
305                 310                 315                 320

Lys

<210> SEQ ID NO 22
<211> LENGTH: 2008
<212> TYPE: DNA
<213> ORGANISM: Cricetulus griseus

<400> SEQUENCE: 22
aacagaaact tattttcctg tgtggctaac tagaaccaga gtacaatgtt tccaattctt      60
tgagctccga aagacagaa gggagttgaa actctgaaaa tgcgggcatg gactggttcc     120
tggcgttgga ttatgctcat tcttttgcc tggggacct tattgtttta tataggtggt      180
catttggttc gagataatga ccaccctgac cattctagca gagaactctc caagattctt     240
gcaaagctgg agcgcttaaa acaacaaaat gaagacttga ggagaatggc tgagtctctc     300
cgaataccag aaggccctat tgatcagggg acagctacag gaagagtccg tgttttagaa     360
```

```
gaacagcttg ttaaggccaa agaacagatt gaaaattaca agaaacaagc taggaatgat      420
ctgggaaagg atcatgaaat cttaaggagg aggattgaaa atggagctaa agagctctgg      480 tttttctac  aaagtgaatt gaagaaatta aagaaattag aaggaaacga actccaaaga      540
catgcagatg aaattctttt ggatttagga catcatgaaa ggtctatcat acagatctta      600
tactacctca gtcaaacaga tggagcaggt gagtggcggg aaaagaagc  caaagatctg      660 acagagctgt ccagcggag  aataacatat ctgcagaatc ccaaggactg cagcaaagcc      720
agaaagctgg tatgtaatat caacaaaggc tgtggctatg gatgtcaact ccatcatgtg      780
gtttactgct tcatgattgc ttatggcacc cagcgaacac tcatcttgga atctcagaat      840
tggcgctatg ctactggagg atgggagact gtgtttagac ctgtaagtga gacatgcaca      900
gacaggtctg gcctctccac tggacactgg tcaggtgaag tgaaggacaa aaatgttcaa      960
gtggtcgagc tccccattgt agacagcctc catcctcgtc ctccttactt acccttggct     1020
gtaccgaaag accttgcaga tcgactcctg agagtccatg tgatcctgc agtgtggtgg      1080 gtatcccagt ttgtcaaata cttgatccgt ccacaacctt ggctggaaag ggaaatagaa     1140
gaaaccacca agaagcttgg cttcaaacat ccagttattg gagtccatgt cagacgcact     1200
gacaaagtgg gaacagaagc agccttccat cccattgagg aatacatggt acacgttgaa     1260
gaacattttc agcttctcga acgcagaatg aaagtggata aaaaagagt  gtatctggcc     1320 actgatgacc cttctttgtt aaaggaggca aagacaaagt actccaatta tgaatttatt     1380
agtgataact ctatttcttg gtcagctgga ctacacaacc gatacacaga aaattcactt     1440
cggggcgtga tcctggatat acactttctc tcccaggctg acttccttgt gtgtactttt     1500
tcatcccagg tctgtagggt tgcttatgaa atcatgcaaa cactgcatcc tgatgcctct     1560
gcaaacttcc attctttaga tgacatctac tattttggag gccaaaatgc ccacaaccag     1620
attgcagttt atcctcacca acctcgaact aaagaggaaa tccccatgga acctggagat     1680
atcattggtg tggctggaaa ccattggaat ggttactcta aaggtgtcaa cagaaaacta     1740
ggaaaaacag gcctgtaccc ttcctacaaa gtccgagaga agatagaaac agtcaaatac     1800
cctacatatc ctgaagctga aaaatagaga tggagtgtaa gagattaaca acagaattta     1860
gttcagacca tctcagccaa gcagaagacc cagactaaca tatggttcat tgacagacat     1920
gctccgcacc aagagcaagt gggaaccctc agatgctgca ctggtggaac gcctctttgt     1980
gaagggctgc tgtgccctca agcccatg                                         2008
```

<210> SEQ ID NO 23
<211> LENGTH: 1728
<212> TYPE: DNA
<213> ORGANISM: Mus musculus

<400> SEQUENCE: 23

```
atgcgggcat ggactggttc ctggcgttgg attatgctca ttctttttgc ctggggggacc       60 ttgttatttt atataggtgg tcatttggtt cgagataatg accaccctga tcactccagc      120
agagaactct ccaagattct tgcaaagctt gaacgcttaa acagcaaaaa tgaagacttg      180
aggcgaatgg ctgagtctct ccgaatacca gaaggcccca ttgaccaggg acagctacta      240
ggaagagtcc gtgttttaga agaacagctt gttaaggcca agaacagat  tgaaaattac      300 aagaaacaag ctgaaatgg  tctggggaag gatcatgaaa tcttaagaag gaggattgaa      360
aatggagcta agagctctg  gttttttcta caaagcgaac tgaagaaatt aaagcattta      420
```

```
gaaggaaatg aactccaaag acatgcagat gaaattcttt tggatttagg acaccatgaa     480
aggtctatca tgacagatct atactacctc agtcaaacag atggagcagg ggattggcgt     540
gaaaagagg ccaaagatct gacagagctg gtccagcgga gaataacata tctccagaat      600
cctaaggact gcagcaaagc caggaagctg gtgtgtaaca tcaataaagg ctgtggctat     660
ggttgtcaac tccatcacgt ggtctactgt ttcatgattg cttatggcac ccagcgaaca     720
ctcatcttgg aatctcagaa ttggcgctat gctactggtg gatgggagac tgtgtttaga     780
cctgtaagtg agacatgtac agacagatct ggcctctcca ctggacactg gtcaggtgaa     840
gtaaatgaca aaacattca agtggtcgag ctccccattg tagacagcct ccatcctcgg      900
cctccttact taccactggc tgttccagaa gaccttgcag accgactcct aagagtccat     960
ggtgaccctg cagtgtggtg ggtgtcccag tttgtcaaat acttgattcg tccacaacct    1020
tggctggaaa aggaaataga agaagccacc aagaagcttg gcttcaaaca tccagttatt    1080
ggagtccatg tcagacgcac agacaaagtg ggaacagaag cagccttcca ccccatcgag    1140
gagtacatgg tacacgttga agaacatttt cagcttctcg cacgcagaat gcaagtggat    1200
aaaaaaagag tatatctggc tactgatgat cctactttgt taaaggaggc aaagacaaag    1260
tactccaatt atgaatttat tagtgataac tctatttctt ggtcagctgg actacacaat    1320
cggtacacag aaaattcact tcggggtgtg atcctggata tacactttct ctcacaggct    1380
gactttctag tgtgtacttt ttcatcccag gtctgtcggg ttgcttatga aatcatgcaa    1440
accctgcatc ctgatgcctc tgcgaacttc cattctttgg atgacatcta ctattttgga    1500
ggccaaaatg cccacaatca gattgctgtt tatcctcaca aacctcgaac tgaagaggaa    1560
attccaatgg aacctggaga tatcattggt gtggctggaa accattggga tggttattct    1620
aaaggtatca cagaaaaact tggaaaaaca ggcttatatc cctcctacaa agtccgagag    1680
aagatagaaa cagtcaagta tcccacatat cctgaagctg aaaaatag                 1728
```

<210> SEQ ID NO 24
<211> LENGTH: 575
<212> TYPE: PRT
<213> ORGANISM: Cricetulus griseus

<400> SEQUENCE: 24

```
Met Arg Ala Trp Thr Gly Ser Trp Arg Trp Ile Met Leu Ile Leu Phe
 1               5                  10                  15

Ala Trp Gly Thr Leu Leu Phe Tyr Ile Gly Gly His Leu Val Arg Asp
                20                  25                  30

Asn Asp His Pro Asp His Ser Ser Arg Glu Leu Ser Lys Ile Leu Ala
            35                  40                  45

Lys Leu Glu Arg Leu Lys Gln Gln Asn Glu Asp Leu Arg Arg Met Ala
        50                  55                  60

Glu Ser Leu Arg Ile Pro Glu Gly Pro Ile Asp Gln Gly Thr Ala Thr
    65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
    130                 135                 140
```

-continued

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
            165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
            195                 200                 205

Lys Leu Val Cys Asn Ile Asn Lys Gly Cys Gly Tyr Gly Cys Gln Leu
            210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
            245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
            275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
            325                 330                 335

Arg Pro Gln Pro Trp Leu Glu Arg Glu Ile Glu Thr Thr Lys Lys
            340                 345                 350

Leu Gly Phe Lys His Pro Val Ile Gly Val His Val Arg Arg Thr Asp
            355                 360                 365

Lys Val Gly Thr Glu Ala Ala Phe His Pro Ile Glu Glu Tyr Met Val
            370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
            405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
            450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Val Tyr Pro
            500                 505                 510

His Gln Pro Arg Thr Lys Glu Glu Ile Pro Met Glu Pro Gly Asp Ile
            515                 520                 525

Ile Gly Val Ala Gly Asn His Trp Asn Gly Tyr Ser Lys Gly Val Asn
            530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys

<210> SEQ ID NO 25
<211> LENGTH: 575
<212> TYPE: PRT
<213> ORGANISM: Mus musculus

<400> SEQUENCE: 25

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Gly Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys His Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
            340                 345                 350

Leu Gly Phe Lys His Pro Val Ile Gly Val His Val Arg Arg Thr Asp
        355                 360                 365

```
Lys Val Gly Thr Glu Ala Ala Phe His Pro Ile Glu Glu Tyr Met Val
            370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Lys Pro Arg Thr Glu Glu Glu Ile Pro Met Glu Pro Gly Asp Ile
            515                 520                 525

Ile Gly Val Ala Gly Asn His Trp Asp Gly Tyr Ser Lys Gly Ile Asn
530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 26
<211> LENGTH: 383
<212> TYPE: DNA
<213> ORGANISM: Cricetulus griseus

<400> SEQUENCE: 26
gttaactggg gctctttaa accctgaatt tttctaaatc cccacctcca agagtttggt      60
ttaaactgat ttttttaatg aatacctttt gaagaataga gcattgtctc atcatgcaaa    120
gcttctcagg gattcagcta gcatgttgaa gaaacataag ggtgttaaat tgtttgtcac    180
aagtgctgaa taaatattga cgtagtcttc agctattcta tactggaagt agatgatatt    240
ctcattggaa attctgttag gaagtaaccc ttcttgtctt cttacctgca tagaatccca    300
ggatataaaa cttgtgcttg tcgcccttgc cattgtctct cactggtggc ctttattgca    360
tctcatatct gccttctctt tcc                                            383

<210> SEQ ID NO 27
<211> LENGTH: 564
<212> TYPE: DNA
<213> ORGANISM: Cricetulus griseus

<400> SEQUENCE: 27
taagaattcc tgtgcccagc tgtatgtgag gctctctgca ggtgtaggga tgtttctgct     60
ttctttctgc acatgcttca cagctgaagt cctttgggtg tgagattgac attcagatag    120
actaaagtga ctggacttgt tgggaaacat actgtatgca ttattgccgt tgcctccagg    180
tgaaattaac acctcattca ccaatccctg ttcatccaaa ctttctaccc acatcacttt    240
aaatagaaat tagacccaat atgactccct tttttcctaag ctgtttatag agattgtgct   300
```

```
ggagcagtga gctttgtgt tgtttgttt gttttgtaat ttccccatg aaaatttctc      360 taaactcaaa cctaagaggg aaaaaaaaaa aacagactta tatgtgccac acttgtaaaa      420
aaaaatcatg aaagatgtat atgatatttt taaacagttt gaatattaag atcacaattt      480
ctattttaaa aacaatcttg ttttacatat caatcaccca attcccttgc cttcccatcc      540
tcccattccc cccactgatc cccc                                             564

<210> SEQ ID NO 28
<211> LENGTH: 120
<212> TYPE: DNA
<213> ORGANISM: Cricetulus griseus

<400> SEQUENCE: 28
atgaatgttc attctttggg tatatgccca agagtagaat tgctaaatat tgaggtagac       60
tgattcccat tttcttgagg agtcgccata ttgatttcca aagtgactgt acaagttaac      120

<210> SEQ ID NO 29
<211> LENGTH: 274
<212> TYPE: DNA
<213> ORGANISM: Cricetulus griseus

<400> SEQUENCE: 29
aggcactagg taaatatttt tgaagaaaga atgagtatct cctatttcag aaaaactttt       60
attgacttaa atttaggata tcagaattag aaaacagtaa aaatttatag gagagttttt      120
aatgaatgtt attttaaggt tccatacaaa tagtaattaa aacttacaca aactatttgt      180
agtaatgatt cagtctggta taccctgatg agcattatac acttttaaat tctttttgta      240 aatttttta ttagttcaaa ttaggaacaa gctt                                  274

<210> SEQ ID NO 30
<211> LENGTH: 9196
<212> TYPE: DNA
<213> ORGANISM: Cricetulus griseus

<400> SEQUENCE: 30
tctagaccag gctggtctcg aactcacaga gaaccacctg cctctgccac ctgagtgctg       60
ggattaaagg tgtgcaccac caccgcccgg cgtaaaatca tattttttgaa tattgtgata      120 atttacatta taattgtaag taaaaatttt cagcctattt tgttatacat ttttgcgtaa      180
attattcttt tttgaaagtt tgttgtcca taatagtcta gggaaacata agttataat      240 ttttgtctat gtatttgcat atatatctat ttaatctcct aatgtccagg aaataaatag      300
ggtatgtaat agcttcaaca tgtggtatga tagaatttt cagtgctata taagttgtta      360
cagcaaagtg ttattaattc atatgtccat atttcaattt tttatgaatt attaaattga      420
atccttaagc tgccagaact agaatttat tttaatcagg aagccccaaa tctgttcatt      480
ctttctatat atgtggaaag gtaggcctca ctaactgatt cttcacctgt tttagaacat      540
ggtccaagaa tggagttatg taaggggaat tacaagtgtg agaaaactcc tagaaaacaa      600
gatgagtctt gtgaccttag tttctttaaa aacacaaaat tcttggaatg tgttttcatg      660
ttcctcccag gtggatagga gtgagtttat ttcagattat ttattacaac tggctgttgt      720
tacttgtttc tatgtctttta tagaaaaaca tattttttt gccacatgca gcttgtcctt      780
atgattttat acttgtgtga ctcttaactc tcagagtata aattgtctga tgctatgaat      840
aaagttggct attgtatgag acttcagccc acttcaatta ttggcttcat tctctcagat      900
cccaccacct ccagagtggt aaacaacttg aaccattaaa cagactttag tctttatttg      960
```

-continued

```
aatgatagat ggggatatca gatttatagg cacagggttt tgagaaaggg agaaggtaaa    1020
cagtagagtt taacaacaac aaaaagtata ctttgtaaac gtaaaactat ttattaaagt    1080
agtagacaag acattaaata ttccttggga ttagtgcttt ttgaattttg ctttcaaata    1140
atagtcagtg agtataccee tcccccattc tatattttag cagaaatcag aataaatggt    1200
gtttctggta cattcttttg tagagaattt attttctttg ggttttgtg catttaaagt     1260 caataaaaat taaggttcag taatagaaaa aaaactctga ttttggaat ccctttctt      1320 cagcttttct atttaatctc ttaatgataa tttaatttgt ggccatgtgg tcaaagtata    1380
tagccttgta tatgtaaatg ttttaaccaa cctgccttta cagtaactat ataattttat    1440
tctataatat atgactttc ttccatagct ttagagttgc ccagtcactt taagttacat     1500
tttcatatat gttctttgtg ggaggagata attttatttc taagagaatc ctaagcatac    1560
tgattgagaa atggcaaaca aaacacataa ttaaagctga taaagaacga catttggag     1620 tttaaaatac atagccaccc taagggttta actgttgtta gccttctttt ggaatttta     1680 ttagttcata tagaaaaatg gattttatcg tgacatttcc atatatgtat ataatatatt    1740
tacatcatat ccacctgtaa ttattagtgt ttttaaatat atttgaaaaa ataatggtct    1800
ggtttgatcc atttgaacct tttgatgttt ggtgtggttg ccaattggtt gatggttatg    1860
ataacctttg cttctctaag gttcaagtca gtttgagaat atgtcctcta aaaatgacag    1920
gttgcaagtt aagtagtgag atgacagcga gatggagtga tgagaatttg tagaaatgaa    1980
ttcacttata ctgagaactt gttttgcttt tagataatga acatattagc ctgaagtaca    2040
tagccgaatt gattaattat tcaaagatat aatctttaa tccctataaa agaggtatta     2100
cacaacaatt caagaaagat agaattagac ttccagtatt ggagtgaacc atttgttatc    2160
aggtagaacc ctaacgtgtg tggttgactt aaagtgttta cttttacct gatactgggt     2220 agctaattgt ctttcagcct cctggccaaa gataccatga aagtcaactt acgttgtatt    2280
ctatatctca aacaactcag ggtgtttctt actctttcca cagcatgtag agcccaggaa    2340
gcacaggaca agaaagctgc ctccttgtat caccaggaag atcttttgt aagagtcatc     2400 acagtatacc agagagacta attttgtctg aagcatcatg tgttgaaaca acagaaactt    2460
attttcctgt gtggctaact agaaccagag tacaatgttt ccaattcttt gagctccgag    2520
aagacagaag ggagttgaaa ctctgaaaat gcgggcatgg actggttcct ggcgttggat    2580
tatgctcatt cttttgcct gggggacctt attgttttat ataggtggtc atttggttcg     2640
agataatgac caccctgacc attctagcag agaactctcc aagattcttg caaagctgga    2700
gcgcttaaaa caacaaatg aagacttgag gagaatggct gagtctctcc ggtaggtttg     2760
aaatactcaa ggatttgatg aaatactgtg cttgaccttt aggtataggg tctcagtctg    2820
ctgttgaaaa atataatttc tacaaaccgt ctttgtaaaa ttttaagtat tgtagcagac    2880
tttttaaaag tcagtgatac atctatatag tcaatatagg tttacatagt tgcaatctta    2940
ttttgcatat gaatcagtat atagaagcag tggcatttat atgcttatgt tgcatttaca    3000
attatgttta gacgaacaca aactttatgt gatttggatt agtgctcatt aaatttttt     3060 attctatgga ctacaacaga gacataaatt ttgaaaggct tagttactct taaattctta    3120
tgatgaaaag caaaaattca ttgttaaata gaacagtgca tccggaatgt gggtaattat    3180
tgccatattt ctagtctact aaaaattgtg gcataactgt tcaaagtcat cagttgtttg    3240
gaaagccaaa gtctgattta aatggaaaac ataaacaatg atatctattt ctagataccT    3300
```

```
ttaacttgca gttactgagt ttacaagttg tctgacaact ttggattctc ttacttcata    3360
tctaagaatg atcatgtgta cagtgcttac tgtcacttta aaaaactgca gggctagaca    3420
tgcagatatg aagactttga cattagatgt ggtaattggc actaccagca agtggtatta    3480
agatacagct gaatatatta cttttttgagg aacataattc atgaatggaa agtggagcat    3540
tagagaggat gccttctggc tctcccacac cactgtttgc atccattgca tttcacactg    3600
cttttagaac tcagatgttt catatggtat attgtgtaac tcaccatcag ttttatcttt    3660
aaatgtctat ggatgataat gttgtatgtt aacactttta caaaaacaaa tgaagccata    3720
tcctcggtgt gagttgtgat ggtggtaatt gtcacaatag gattattcag caaggaacta    3780
agtcagggac aagaagtggg cgatactttg ttggattaaa tcattttact ggaagttcat    3840
cagggagggt tatgaaagtt gtggtctttg aactgaaatt atatgtgatt cattattctt    3900
gatttaggcc ttgctaatag taactatcat ttattgggaa tttgtcatat gtgccaattt    3960
gtcatgggcc agacagcgtg ttttactgaa tttctagata tctttatgag attctagtac    4020
tgttttcagc cattttacag atgaagaatc ttaaaaaatg ttaaataatt tagttttgccc    4080 aagattatac gttaacaaat ggtagaacct tctttgaatt ctggcagtat ggctacacag    4140
tccgaactct tatcttccta agctgaaaac agaaaaagca atgacccaga aaatttttatt   4200 taaaagtctc aggagagact tcccatcctg agaagatctc ttttccctt tataatttag     4260 gctcctgaat aatcactgaa ttttctccat gttccatcta tagtactgtt atttctgttt    4320 tcctttttc ttaccacaaa gtatcttgtt tttgctgtat gaaagaaaat gtgttattgt     4380
aatgtgaaat tctctgtccc tgcagggtcc cacatccgcc tcaatcccaa ataaacacac    4440
agaggctgta ttaattatga aactgttggt cagttggcta gggcttctta ttggctagct    4500
ctgtcttaat tattaaacca taactactat tgtaagtatt tccatgtggt cttatcttac    4560
caaggaaagg gtccagggac ctcttactcc tctggcgtgt tggcagtgaa gaggagagag    4620
cgatttccta tttgtctctg cttatttcct gattctgctc agctatgtca cttcctgcct    4680
ggccaatcag ccaatcagtg ttttattcat tagccaataa aagaaacatt tacacagaag    4740
gacttccccc atcatgttat ttgtatgagt tcttcagaaa atcatagtat cttttaatac    4800 taattttttat aaaaaattaa ttgtattgaa aattatgtgt atatgtgtct gtgtgtcgat   4860
ttgtgctcat aagtagcatg gagtgcagaa gagggaatca gatctttttt taagggacaa    4920
agagtttatt cagattacat tttaaggtga taatgtatga ttgcaaggtt atcaacatgg    4980
cagaaatgtg aagaagctgg tcacattaca tccagagtca agagtagaga gcaatgaatt    5040
gatgcatgca ttcctgtgct cagctcactt ttcctggagc tgagctgatt gtaagccatc    5100
tgatgtcttt gctgggaact aactcaaagg caagttcaaa acctgttctt aagtataagc    5160
catctctcca gtccctcata tggtctctta agacactttc tttatattct tgtacataga    5220
aattgaattc ctaacaactg cattcaaatt acaaaatagt ttttaaaagc tgatataata    5280
aatgtaaata caatctagaa cattttttata aataagcata ttaactcagt aaaaataaat   5340
gcatggttat tttccttcat tagggaagta tgtctcccca ggctgttctc tagattctac    5400
tagtaatgct gtttgtacac catccacagg ggttttattt taaagctaag acatgaatga    5460
tggacatgct tgttagcatt tagactttt tccttactat aattgagcta gtattttgt     5520 gctcagtttg atatctgtta attcagataa atgtaatagt aggtaatttc tttgtgataa    5580
aggcatataa attgaagttg gaaaacaaaa gcctgaaatg acagttttta agattcagaa    5640
caataatttt caaaagcagt tacccaactt tccaaataca atctgcagtt ttcttgatat    5700
```

```
gtgataaatt tagacaaaga aatagcacat tttaaaatag ctatttactc ttgattttt     5760 tttcaaattt aggctagttc actagttgtg tgtaaggtta tggctgcaaa catctttgac     5820
tcttggttag ggaatccagg atgatttacg tgtttggcca aaatcttgtt ccattctggg     5880
tttcttctct atctaggtag ctagcacaag ttaaggtgt ggtagtattg gaaggctctc      5940
aggtatatat ttctatattc tgtattttt tcctctgtca tatatttgct ttctgtttta      6000
ttgatttcta ctgttagttt gatacttact ttcttacact ttctttggga tttattttgc     6060
tgttctaaga tttcttagca agttcatatc actgatttta acagttgctt cttttgtaat     6120
atagactgaa tgcccttat ttgaaatgct tgggatcaga aactcagatt tgaacttttc      6180 tttttaata tttccatcaa gtttaccagc tgaatgtcct gatccaagaa tatgaaatct      6240
gaaatgcttt gaaatctgaa acttttagag tgataaagct tcccttaaa ttaatttgtg      6300 ttctatattt tttgacaatg tcaacctttc attgttatcc aatgagtgaa catattttca     6360
atttttttgt ttgatctgtt atattttgat ctgaccatat ttataaaatt ttatttaatt     6420
tgaatgttgt gctgttactt atctttatta ttatttttgc ttatttttcta gccaaatgaa    6480 attatattct gtattatttt agtttgaatt ttacttttgtg gcttagtaac tgccttttgt    6540
tggtgaatgc ttaagaaaaa cgtgtggtct actgatattg gttctaatct tatatagcat     6600
gttgtttgtt aggtagttga ttatgctggt cagattgtct tgagtttatg caaatgtaaa     6660
atatttagat gcttgttttg ttgtctaaga acaaagtatg cttgctgtct cctatcggtt     6720
ctggtttttc cattcatctc ttcaagctgt tttgtgtgtt gaatactaac tccgtactat     6780
cttgttttct gtgaattaac ccctttcaa aggtttcttt tctttttttt tttaagggac      6840
aacaagttta ttcagattac attttaagct gataatgtat gattgcaagg ttatcaacat     6900
ggcagaaatg tgaagaagct aggcacatta catccacatg gagtcaagag cagagagcag     6960
tgaattaatg catgcattcc tgtggtcagc tcacttttcc tattcttaga tagtctagga     7020
tcataaacct ggggaatagt gctaccacaa tgggcatatc cacttacttc agttcatgca     7080
atcaaccaag gcacatccac aggaaaaact gatttagaca acctctcatt gagactcttc     7140
ccagatgatt agactgtgtc aagttgacaa ttaaaactat cacacctgaa gccatcacta     7200
gtaaatataa tgaaaatgtt gattatcacc ataattcatc tgtatcccct tgttattgta     7260
gattttgtga agttcctatt caagtccctg ttccttcctt aaaaacctgt ttttttagtta   7320 aataggttt ttagtgttcc tgtctgtaaa tactttttta agttagata ttattttcaa       7380 gtatgttctc ccagtctttg gcttgtattt tcatcccttc aatacatata ttttttgtaat    7440 ttattttttt tatttaaatt agaaacaaag ctgcttttac atgtcagtct cagttccctc     7500
tccctcccct cctcccctgc tccccaccta agcccaatt ccaactcctt tcttctcccc      7560
aggaagggtg aggccctcca tgggggaaat cttcaatgtc tgtcatatca tttggagcag     7620
ggcctagacc ctccccagtg tgtctaggct gagagagtat ccctctatgt ggagagggct     7680
cccaaagttc atttgtgtac taggggtaaa tactgatcca ctatcagtgg ccccatagat    7740
tgtccggacc tccaaactga cttcctcctt cagggagtct ggaacagttc tatgctggtt     7800
tcccagatat cagtctgggg tccatgagca accccttgtt caggtcagtt gtttctgtag     7860
gtttccccag cccggtcttg acccctttgc tcatcacttc tccctctctg caactggatt     7920
ccagagttca gctcagtgtt tagctgtggg tgtctgcatc tgcttccatc agctactgga     7980
tgagggctct aggatggcat ataaggtagt catcagtctc attatcagag aagggcttt      8040
```

-continued

```
aaggtagcct cttgattatt gcttagattg ttagttgggg tcaaccttgt aggtctctgg    8100
acagtgacag aattctcttt aaacctataa tggctccctc tgtggtggta tcccttttct    8160
tgctctcatc cgttcctccc ctgactagat cttcctgctc cctcatgtcc tcctctcccc    8220
tccccttctc cccttctctt tcttctaact ccctctcccc tccacccacg atccccatta    8280
gcttatgaga tcttgtcctt attttagcaa aaccttttg gctataaaat taattaattt    8340
aatatgctta tatcaggttt attttggcta gtatttgtat gtgtttggtt agtgttttta    8400
accttaattg acatgtatcc ttatatttag acacagattt aaatatttga agtttttttt    8460 ttttttttt ttaaagattt atttattttt tatgtcttct gcctgcatgc cagaagaggg    8520
caccagatct cattcaaggt ggttgtgagc caccatgtgg ttgctgggaa ttgaactcag    8580
gacctctgga agaacagtca gtgctcttaa ccgctgagcc atctctccag cccctgaagt    8640
gtttctttta aagaggatag cagtgcatca ttttcccctt tgaccaatga ctcctacctt    8700
actgaattgt tttagccatt tatatgtaat gctgttacca ggtttacatt ttcttttatc    8760
ttgctaaatt tcttccctgt ttgtctcatc tcttatttt gtctgttgga ttatataggc    8820 tttattttt ctgttttac agtaagttat atcaaattaa aattatttta tggaatgggt    8880
gtgttgacta catgtatgtc tgtgcaccat gtgctgacct ggtcttggcc agaagaaggt    8940
gtcatattct ctgaaactgg tattgtggat gttacgaact gccatagggt gctaggaatc    9000 aaacccagc tcctctggaa aagcagccac tgctctgagc cactgagtcc tctcttcaag    9060
caggtgatgc caacttttaa tggttaccag tggataagag tgcttgtatc tctagcaccc    9120
atgaaaattt atgcattgct atatgggctt gtcacttcag cattgtgtga cagagacagg    9180
aggatcccaa gagctc                                                   9196
```

<210> SEQ ID NO 31
<211> LENGTH: 330
<212> TYPE: PRT
<213> ORGANISM: Artificial Sequence
<220> FEATURE:
<223> OTHER INFORMATION: Synthetic peptide

<400> SEQUENCE: 31

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160
```

```
Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 990
<212> TYPE: DNA
<213> ORGANISM: Artificial Sequence
<220> FEATURE:
<223> OTHER INFORMATION: Synthetic DNA

<400> SEQUENCE: 32
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga    360 ccgtcagtct tcctcttccc cccaaaaccc aaggacaccc tcatgatctc ccggaccccct   420 gaggtcacat gcgtggtggt ggacgtgagc cacgaagacc ccgaggtcca gttcaagtgg     480
tacgtggacg gcgtggaggt gcataatgcc aagacaaagc cgcgggagga gcagttcaac     540
agcacgttcc gtgtggtcag cgtcctcacc gtcctgcacc aggactggct gaacggcaag     600
gagtacaagt gcaaggtctc caacaaagcc ctcccagccc ccatcgagaa aaccatctcc     660
aaaaccaaag gacagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990
```

<210> SEQ ID NO 33
<211> LENGTH: 330
<212> TYPE: PRT
<213> ORGANISM: Artificial Sequence
<220> FEATURE:
<223> OTHER INFORMATION: Synthetic peptide

<400> SEQUENCE: 33

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 34
<211> LENGTH: 329
<212> TYPE: DNA
<213> ORGANISM: Artificial Sequence
<220> FEATURE:
<223> OTHER INFORMATION: Synthetic DNA

<400> SEQUENCE: 34

```
ccacaggtgt acaccctgcc cccatcccgg gaggagctga ccaagaacca ggtcagcctg      60
acctgcctgg tcaaaggctt ctatcccagc gacatcgccg tggagtggga gagcaatggg     120
cagccggaga caactacaa gaccacgcct cccgtgctgg actccgacgg ctccttcttc      180
ctctacagca agctcaccgt ggacaagagc aggtggcagc aggggaacgt cttctcatgc    240
tccgtgatgc atgaggctct gcacaaccac tacacgcaga gagcctctc cctgtctccg     300
ggtaaatgag tgcgactcgc gaggtaccg                                      329
```

<210> SEQ ID NO 35
<211> LENGTH: 49
<212> TYPE: DNA
<213> ORGANISM: Artificial Sequence
<220> FEATURE:
<223> OTHER INFORMATION: Synthetic DNA

<400> SEQUENCE: 35

```
ccacaggtgt acaccctgcc cccatcccgg gaggagctga ccaagaacc                 49
```

<210> SEQ ID NO 36
<211> LENGTH: 69
<212> TYPE: DNA
<213> ORGANISM: Artificial Sequence
<220> FEATURE:
<223> OTHER INFORMATION: Synthetic DNA

<400> SEQUENCE: 36

```
cggtacctcg cgagtcgcac tcatttaccc ggagacaggg agaggctctt ctgcgtgtag      60
tggttgtgc                                                             69
```

<210> SEQ ID NO 37
<211> LENGTH: 330
<212> TYPE: PRT
<213> ORGANISM: Artificial Sequence
<220> FEATURE:
<223> OTHER INFORMATION: Synthetic peptide

<400> SEQUENCE: 37

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
```

```
                145                 150                 155                 160
Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 329
<212> TYPE: DNA
<213> ORGANISM: Artificial Sequence
<220> FEATURE:
<223> OTHER INFORMATION: Synthetic DNA

<400> SEQUENCE: 38
ccacaggtgt acaccctgcc cccatcccgg gaggagatga ccaagaacca ggtcagcctg      60
acctgcctgg tcaaaggctt ctatcccagc gacatcgccg tggagtggga gagcaatggg     120
cagccggaga acaactacaa gaccacgcct cccgtgctgg actccgacgg ctccttcttc     180
ctctacagca agctcaccgt ggacaagagc aggtggcagc aggggaacgt cttctcatgc     240
tccgtgatgc atgaggctct gcacaaccac tacacgcaga agagcctctc cctgtctccg     300
ggtaaatgag tgcgactcgc gaggtaccg                                        329

<210> SEQ ID NO 39
<211> LENGTH: 49
<212> TYPE: DNA
<213> ORGANISM: Artificial Sequence
<220> FEATURE:
<223> OTHER INFORMATION: Synthetic DNA

<400> SEQUENCE: 39
ccacaggtgt acaccctgcc cccatcccgg gaggagatga ccaagaacc                  49

<210> SEQ ID NO 40
<211> LENGTH: 330
<212> TYPE: PRT
<213> ORGANISM: Artificial Sequence
<220> FEATURE:
<223> OTHER INFORMATION: Synthetic peptide

<400> SEQUENCE: 40
```

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 329
<212> TYPE: DNA
<213> ORGANISM: Artificial Sequence
<220> FEATURE:
<223> OTHER INFORMATION: Synthetic DNA

<400> SEQUENCE: 41
ccacaggtgt acaccctgcc cccatcccgg gaggagatga ccaagaacca ggtcagcctg    60
acctgcctgg tcaaaggctt ctaccccagc gacatcgccg tggagtggga gagcagcggg   120
cagccggaga caactacaa gaccacgcct cccgtgctgg actccgacgg ctccttcttc    180
```

```
ctctacagca agctcaccgt ggacaagagc aggtggcagc aggggaacgt cttctcatgc    240
tccgtgatgc atgaggctct gcacaaccac tacacgcaga agagcctctc cctgtctccg    300
ggtaaatgag tgcgactcgc gaggtaccg                                      329
```

<210> SEQ ID NO 42
<211> LENGTH: 174
<212> TYPE: DNA
<213> ORGANISM: Artificial Sequence
<220> FEATURE:
<223> OTHER INFORMATION: Synthetic DNA

<400> SEQUENCE: 42

```
ccacaggtgt acaccctgcc cccatcccgg gaggagatga ccaagaacca ggtcagcctg     60
acctgcctgg tcaaaggctt ctaccccagc gacatcgccg tggagtggga gagcagcggg    120
cagccggaga acaactacaa gaccacgcct cccgtgctgg actccgacgg ctcc          174
```

<210> SEQ ID NO 43
<211> LENGTH: 174
<212> TYPE: DNA
<213> ORGANISM: Artificial Sequence
<220> FEATURE:
<223> OTHER INFORMATION: Synthetic DNA

<400> SEQUENCE: 43

```
cggtacctcg cgagtcgcac tcatttaccc ggagacaggg agaggctctt ctgcgtgtag     60
tggttgtgca gagcctcatg catcacggag catgagaaga cgttcccctg ctgccacctg    120
ctcttgtcca cggtgagctt gctgtagagg aagaaggagc cgtcggagtc cagc          174
```

<210> SEQ ID NO 44
<211> LENGTH: 330
<212> TYPE: PRT
<213> ORGANISM: Artificial Sequence
<220> FEATURE:
<223> OTHER INFORMATION: Synthetic peptide

<400> SEQUENCE: 44

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
```

```
                    165                 170                 175
Glu Gln Phe Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
                260                 265                 270

Asn Tyr Asn Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 329
<212> TYPE: DNA
<213> ORGANISM: Artificial Sequence
<220> FEATURE:
<223> OTHER INFORMATION: Synthetic DNA

<400> SEQUENCE: 45
ccacaggtgt acaccctgcc cccatcccgg gaggagatga ccaagaacca ggtcagcctg      60
acctgcctgg tcaaaggctt ctaccccagc gacatcgccg tggagtggga gagcagcggg     120
cagccggaga caactacaa caccacgcct cccgtgctgg actccgacgg ctccttcttc     180
ctctacagca agctcaccgt ggacaagagc aggtggcagc aggggaacgt cttctcatgc     240
tccgtgatgc atgaggctct gcacaaccac tacacgcaga agagcctctc cctgtctccg     300
ggtaaatgag tgcgactcgc gaggtaccg                                       329

<210> SEQ ID NO 46
<211> LENGTH: 174
<212> TYPE: DNA
<213> ORGANISM: Artificial Sequence
<220> FEATURE:
<223> OTHER INFORMATION: Synthetic DNA

<400> SEQUENCE: 46
ccacaggtgt acaccctgcc cccatcccgg gaggagatga ccaagaacca ggtcagcctg      60
acctgcctgg tcaaaggctt ctaccccagc gacatcgccg tggagtggga gagcagcggg     120
cagccggaga caactacaa caccacgcct cccgtgctgg actccgacgg ctcc            174

<210> SEQ ID NO 47
<211> LENGTH: 330
<212> TYPE: PRT
<213> ORGANISM: Artificial Sequence
<220> FEATURE:
<223> OTHER INFORMATION: Synthetic peptide

<400> SEQUENCE: 47
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 329
<212> TYPE: DNA
<213> ORGANISM: Artificial Sequence
<220> FEATURE:
<223> OTHER INFORMATION: Synthetic DNA

<400> SEQUENCE: 48
ccacaggtgt acaccctgcc cccatcccgg gaggagatga ccaagaacca ggtcagcctg    60
acctgcctgg tcaaaggctt ctaccccagc gacatcgccg tggagtggga gagcagcggg   120
cagccggaga acaactacaa caccacgcct cccatgctgg actccgacgg ctccttcttc   180

```
ctctacagca agctcaccgt ggacaagagc aggtggcagc aggggaacgt cttctcatgc      240
tccgtgatgc atgaggctct gcacaaccac tacacgcaga agagcctctc cctgtctccg      300
ggtaaatgag tgcgactcgc gaggtaccg                                        329
```

<210> SEQ ID NO 49
<211> LENGTH: 174
<212> TYPE: DNA
<213> ORGANISM: Artificial Sequence
<220> FEATURE:
<223> OTHER INFORMATION: Synthetic DNA

<400> SEQUENCE: 49

```
ccacaggtgt acaccctgcc cccatcccgg gaggagatga ccaagaacca ggtcagcctg       60
acctgcctgg tcaaaggctt ctaccccagc gacatcgccg tggagtggga gagcagcggg      120
cagccggaga acaactacaa caccacgcct cccatgctgg actccgacgg ctcc            174
```

<210> SEQ ID NO 50
<211> LENGTH: 330
<212> TYPE: PRT
<213> ORGANISM: Artificial Sequence
<220> FEATURE:
<223> OTHER INFORMATION: Synthetic peptide

<400> SEQUENCE: 50

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                     245                 250                 255
Pro Ser Asp Ile Ala Val Glu Trp Glu Ser Ser Gly Gln Pro Glu Asn
                260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 51
<211> LENGTH: 329
<212> TYPE: DNA
<213> ORGANISM: Artificial Sequence
<220> FEATURE:
<223> OTHER INFORMATION: Synthetic DNA

<400> SEQUENCE: 51
ccacaggtgt acaccctgcc cccatcccgg gaggagatga ccaagaacca ggtcagcctg      60
acctgcctgg tcaaaggctt ctaccccagc gacatcgccg tggagtggga gagcagcggg     120
cagccggaga acaactacaa caccacgcct cccatgctgg actccgacgg ctccttcttc     180
ctctacagca agctcaccgt ggacaagagc aggtggcagc aggggaacat cttctcatgc     240
tccgtgatgc atgaggctct gcacaaccac tacacgcaga gagcctctc cctgtctccg      300 ggtaaatgag tgcgactcgc gaggtaccg                                       329

<210> SEQ ID NO 52
<211> LENGTH: 330
<212> TYPE: PRT
<213> ORGANISM: Artificial Sequence
<220> FEATURE:
<223> OTHER INFORMATION: Synthetic peptide

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160
```

```
Tyr Val Asp Gly Val Glu Val His Asn Ala Lys Thr Lys Pro Arg Glu
            165                 170                 175
Glu Gln Phe Asn Ser Thr Phe Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Thr Lys Gly
210                 215                 220
Gln Pro Arg Glu Pro Gln Val Tyr Thr Leu Pro Ser Arg Glu Glu
225                 230                 235                 240
Met Thr Lys Asn Gln Val Ser Leu Thr Cys Leu Val Lys Gly Phe Tyr
            245                 250                 255
Pro Ser Asp Ile Ala Val Glu Trp Glu Ser Ser Gly Gln Pro Glu Asn
        260                 265                 270
Asn Tyr Asn Thr Thr Pro Pro Met Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Ile Phe Ser Cys Ser Val Met His Glu Ala Leu His Asn Arg Tyr Thr
305                 310                 315                 320
Gln Lys Ser Leu Ser Leu Ser Pro Gly Lys
            325                 330

<210> SEQ ID NO 53
<211> LENGTH: 329
<212> TYPE: DNA
<213> ORGANISM: Artificial Sequence
<220> FEATURE:
<223> OTHER INFORMATION: Synthetic DNA

<400> SEQUENCE: 53
ccacaggtgt acaccctgcc cccatcccgg gaggagatga ccaagaacca ggtcagcctg      60
acctgcctgg tcaaaggctt ctaccccagc gacatcgccg tggagtggga gagcagcggg     120
cagccggaga caactacaa caccacgcct cccatgctgg actccgacgg ctccttcttc     180
ctctacagca agctcaccgt ggacaagagc aggtggcagc aggggaacat cttctcatgc     240
tccgtgatgc atgaggctct gcacaaccgc tacacgcaga agagcctctc cctgtctccg     300
ggtaaatgag tgcgactcgc gaggtaccg                                      329

<210> SEQ ID NO 54
<211> LENGTH: 69
<212> TYPE: DNA
<213> ORGANISM: Artificial Sequence
<220> FEATURE:
<223> OTHER INFORMATION: Synthetic DNA

<400> SEQUENCE: 54
cggtacctcg cgagtcgcac tcatttaccc ggagacaggg agaggctctt ctgcgtgtag      60
cggttgtgc                                                             69

<210> SEQ ID NO 55
<211> LENGTH: 330
<212> TYPE: PRT
<213> ORGANISM: Artificial Sequence
<220> FEATURE:
<223> OTHER INFORMATION: Synthetic peptide

<400> SEQUENCE: 55
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Phe Thr
305                 310                 315                 320

Gln Lys Ser Leu Ser Leu Ser Pro Gly Lys
                325                 330

<210> SEQ ID NO 56
<211> LENGTH: 329
<212> TYPE: DNA
<213> ORGANISM: Artificial Sequence
<220> FEATURE:
<223> OTHER INFORMATION: Synthetic DNA

<400> SEQUENCE: 56
ccacaggtgt acaccctgcc cccatcccgg gaggagatga ccaagaacca ggtcagcctg      60
acctgcctgg tcaaaggctt ctaccccagc gacatcgccg tggagtggga gagcagcggg     120
cagccggaga acaactacaa caccacgcct cccatgctgg actccgacgg ctccttcttc     180

```
ctctacagca agctcaccgt ggacaagagc aggtggcagc aggggaacat cttctcatgc    240
tccgtgatgc atgaggctct gcacaaccac ttcacgcaga agagcctctc cctgtctccg    300
ggtaaatgag tgcgactcgc gaggtaccg                                       329
```

<210> SEQ ID NO 57
<211> LENGTH: 69
<212> TYPE: DNA
<213> ORGANISM: Artificial Sequence
<220> FEATURE:
<223> OTHER INFORMATION: Synthetic DNA

<400> SEQUENCE: 57

```
cggtacctcg cgagtcgcac tcatttaccc ggagacaggg agaggctctt ctgcgtgaag     60
tggttgtgc                                                             69
```

<210> SEQ ID NO 58
<211> LENGTH: 121
<212> TYPE: PRT
<213> ORGANISM: Artificial Sequence
<220> FEATURE:
<223> OTHER INFORMATION: Synthetic peptide

<400> SEQUENCE: 58

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Asp Phe
                 20                  25                  30

Tyr Met Asn Trp Val Arg Gln Pro Pro Gly Arg Gly Leu Glu Trp Ile
             35                  40                  45

Gly Phe Ile Arg Asp Lys Ala Lys Gly Tyr Thr Thr Glu Tyr Asn Pro
         50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser
            115                 120
```

<210> SEQ ID NO 59
<211> LENGTH: 363
<212> TYPE: DNA
<213> ORGANISM: Artificial Sequence
<220> FEATURE:
<223> OTHER INFORMATION: Synthetic DNA

<400> SEQUENCE: 59

```
caggtccaac tgcaggagag cggtccaggt cttgtgagac ctagccagac cctgagcctg     60
acctgcaccg tgtctggctt caccttcacc gatttctaca tgaactgggt gagacagcca    120
cctggacgag gtcttgagtg gattggattt attagagaca agctaaaggg ttacacaaca    180
gagtacaatc catctgtgaa ggggagagtg acaatgctgg tagacaccag caagaaccag    240
ttcagcctga gactcagcag cgtgacagcc gccgacaccg cggtctatta ttgtgcaaga    300
gagggccaca ctgctgctcc ttttgattac tggggtcaag gcagcctcgt cacagtctcc    360
tca                                                                  363
```

<210> SEQ ID NO 60
<211> LENGTH: 107
<212> TYPE: PRT
<213> ORGANISM: Artificial Sequence
<220> FEATURE:
<223> OTHER INFORMATION: Synthetic peptide

<400> SEQUENCE: 60

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Ile Asp Lys Tyr
             20                  25                  30

Leu Asn Trp Tyr Gln Gln Lys Pro Gly Lys Ala Pro Lys Leu Leu Ile
         35                  40                  45

Tyr Asn Thr Asn Asn Leu Gln Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Gln Gly Thr Lys Val Glu Ile Lys
            100                 105
```

<210> SEQ ID NO 61
<211> LENGTH: 321
<212> TYPE: DNA
<213> ORGANISM: Artificial Sequence
<220> FEATURE:
<223> OTHER INFORMATION: Synthetic DNA

<400> SEQUENCE: 61

```
gacatccaga tgacccagag cccaagcagc ctgagcgcca gcgtgggtga cagagtgacc      60
atcacctgta aagcaagtca gaatattgac aaatacttaa actggtacca gcagaagcca     120
ggtaaggctc caaagctgct gatctacaat acaaacaatt tgcaaacggg tgtgccaagc     180
agattcagcg gtagcggtag cggtaccgac ttcaccttca ccatcagcag cctccagcca     240
gaggacatcg ccacctacta ctgcttgcag catataagta ggccgcgcac gttcggccaa     300
gggaccaagg tggaaatcaa a                                               321
```

<210> SEQ ID NO 62
<211> LENGTH: 451
<212> TYPE: PRT
<213> ORGANISM: Artificial Sequence
<220> FEATURE:
<223> OTHER INFORMATION: Synthetic peptide

<400> SEQUENCE: 62

```
Gln Val Gln Leu Gln Glu Ser Gly Pro Gly Leu Val Arg Pro Ser Gln
  1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
 50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95
```

Tyr Cys Ala Arg Glu Gly His Thr Ala Ala Pro Phe Asp Tyr Trp Gly
            100                 105                 110

Gln Gly Ser Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Ser Gly Gln Pro Glu Asn Asn Tyr Asn Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 63
<211> LENGTH: 214
<212> TYPE: PRT
<213> ORGANISM: Artificial Sequence
<220> FEATURE:
<223> OTHER INFORMATION: Synthetic peptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Leu Gln His Ile Ser Arg Pro Arg
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 64
<211> LENGTH: 476
<212> TYPE: DNA
<213> ORGANISM: Artificial Sequence
<220> FEATURE:
<223> OTHER INFORMATION: Synthetic DNA

<400> SEQUENCE: 64
cccacaagct gcggccgcga cccctcacca tgggatggag ctgtatcatc ctcttcttgg      60
tagcaacagc tacaggtgtc cactcccagg tccaactgca ggagagcggt ccaggtcttg    120
tgagacctag ccagaccctg agcctgacct gcaccgtgtc tggcttcacc ttcaccgatt    180
tctacatgaa ctgggtgaga cagccacctg gacgaggtct tgagtggatt ggatttatta    240
gagacaaagc taaggttac acaacagagt acaatccatc tgtgaagggg agagtgacaa    300
tgctggtaga caccagcaag aaccagttca gcctgagact cagcagcgtg acagccgccg    360
acaccgcggt ctattattgt gcaagagagg gccacactgc tgctcctttt gattactggg    420
gtcaaggcag cctcgtcaca gtctcctcag cctccaccaa gggcccatcg gtcttc        476

<210> SEQ ID NO 65
<211> LENGTH: 131
<212> TYPE: DNA
<213> ORGANISM: Artificial Sequence
<220> FEATURE:
<223> OTHER INFORMATION: Synthetic DNA

<400> SEQUENCE: 65

```
cccacaagct gcggccgcga cccctcacca tgggatggag ctgtatcatc ctcttcttgg      60
tagcaacagc tacaggtgtc cactcccagg tccaactgca ggagagcggt ccaggtcttg     120
tgagacctag c                                                          131
```

<210> SEQ ID NO 66
<211> LENGTH: 140
<212> TYPE: DNA
<213> ORGANISM: Artificial Sequence
<220> FEATURE:
<223> OTHER INFORMATION: Synthetic DNA

<400> SEQUENCE: 66

```
gctttgtctc taataaatcc aatccactca agacctcgtc caggtggctg tctcacccag      60
ttcatgtaga atcggtgaa ggtgaagcca gacacggtgc aggtcaggct cagggtctgg     120
ctaggtctca caagacctgg                                                 140
```

<210> SEQ ID NO 67
<211> LENGTH: 140
<212> TYPE: DNA
<213> ORGANISM: Artificial Sequence
<220> FEATURE:
<223> OTHER INFORMATION: Synthetic DNA

<400> SEQUENCE: 67

```
ggattggatt tattagagac aaagctaaag gttacacaac agagtacaat ccatctgtga      60
aggggagagt gacaatgctg gtagacacca gcaagaacca gttcagcctg agactcagca     120
gcgtgacagc cgccgacacc                                                 140
```

<210> SEQ ID NO 68
<211> LENGTH: 131
<212> TYPE: DNA
<213> ORGANISM: Artificial Sequence
<220> FEATURE:
<223> OTHER INFORMATION: Synthetic DNA

<400> SEQUENCE: 68

```
gaagaccgat gggcccttgg tggaggctga ggagactgtg acgaggctgc cttgacccca      60
gtaatcaaaa ggagcagcag tgtggccctc tcttgcacaa taatagaccg cggtgtcggc     120
ggctgtcacg c                                                          131
```

<210> SEQ ID NO 69
<211> LENGTH: 421
<212> TYPE: DNA
<213> ORGANISM: Artificial Sequence
<220> FEATURE:
<223> OTHER INFORMATION: Synthetic DNA

<400> SEQUENCE: 69

```
cccacaagct gaattcgcct cctcaaaatg gatggagct gtatcatcct cttcttggta      60
gcaacagcta caggtgtcca ctccgacatc cagatgaccc agagcccaag cagcctgagc     120
gccagcgtgg gtgacagagt gaccatcacc tgtaaagcaa gtcagaatat tgacaaatac     180
ttaaactggt accagcagaa gccaggtaag gctccaaagc tgctgatcta caatacaaac     240
aatttgcaaa cgggtgtgcc aagcagattc agcggtagcg gtagcggtac cgacttcacc     300
ttcaccatca gcagcctcca gccagaggac atcgccacct actactgctt gcagcatata     360
agtaggccgc gcacgttcgg ccaagggacc aaggtggaaa tcaaacgtac ggtggctgca     420
c                                                                     421
```

<210> SEQ ID NO 70
<211> LENGTH: 120
<212> TYPE: DNA
<213> ORGANISM: Artificial Sequence
<220> FEATURE:
<223> OTHER INFORMATION: Synthetic DNA

<400> SEQUENCE: 70

```
cccacaagct gaattcgcct cctcaaaatg ggatggagct gtatcatcct cttcttggta      60
gcaacagcta caggtgtcca ctccgacatc cagatgaccc agagcccaag cagcctgagc    120
```

<210> SEQ ID NO 71
<211> LENGTH: 117
<212> TYPE: DNA
<213> ORGANISM: Artificial Sequence
<220> FEATURE:
<223> OTHER INFORMATION: Synthetic DNA

<400> SEQUENCE: 71

```
ggagccttac ctggcttctg ctggtaccag tttaagtatt tgtcaatatt ctgacttgct      60
ttacaggtga tggtcactct gtcacccacg ctggcgctca ggctgcttgg gctctgg       117
```

<210> SEQ ID NO 72
<211> LENGTH: 125
<212> TYPE: DNA
<213> ORGANISM: Artificial Sequence
<220> FEATURE:
<223> OTHER INFORMATION: Synthetic DNA

<400> SEQUENCE: 72

```
gcagaagcca ggtaaggctc caaagctgct gatctacaat acaaacaatt tgcaaacggg      60
tgtgccaagc agattcagcg gtagcggtag cggtaccgac ttcaccttca ccatcagcag    120
cctcc                                                                 125
```

<210> SEQ ID NO 73
<211> LENGTH: 123
<212> TYPE: DNA
<213> ORGANISM: Artificial Sequence
<220> FEATURE:
<223> OTHER INFORMATION: Synthetic DNA

<400> SEQUENCE: 73

```
gtgcagccac cgtacgtttg atttccacct tggtcccttg gccgaacgtg cgcggcctac      60
ttatatgctg caagcagtag taggtggcga tgtcctctgg ctggaggctg ctgatggtga    120
agg                                                                   123
```

<210> SEQ ID NO 74
<211> LENGTH: 451
<212> TYPE: PRT
<213> ORGANISM: Artificial Sequence
<220> FEATURE:
<223> OTHER INFORMATION: Synthetic peptide

<400> SEQUENCE: 74

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45
```

-continued

```
Gly Phe Ile Arg Asp Lys Ala Lys Gly Tyr Thr Thr Glu Tyr Asn Pro
 50                  55                  60
Ser Val Lys Gly Arg Val Thr Met Leu Val Asp Thr Ser Lys Asn Gln
 65                  70                  75                  80
Phe Ser Leu Arg Leu Ser Ser Val Thr Ala Ala Asp Thr Ala Val Tyr
                 85                  90                  95
Tyr Cys Ala Arg Glu Gly His Thr Ala Ala Pro Phe Asp Tyr Trp Gly
                100                 105                 110
Gln Gly Ser Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
450
```

<210> SEQ ID NO 75
<211> LENGTH: 451
<212> TYPE: PRT
<213> ORGANISM: Artificial Sequence
<220> FEATURE:
<223> OTHER INFORMATION: Synthetic peptide

<400> SEQUENCE: 75

```
Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Thr Phe Thr Asp Phe
             20                  25                  30

Tyr Met Asn Trp Val Arg Gln Pro Pro Gly Arg Gly Leu Glu Trp Ile
         35                  40                  45

Gly Phe Ile Arg Asp Lys Ala Lys Gly Tyr Thr Thr Glu Tyr Asn Pro
     50                  55                  60

Ser Val Lys Gly Arg Val Thr Met Leu Val Asp Thr Ser Lys Asn Gln
 65                  70                  75                  80

Phe Ser Leu Arg Leu Ser Ser Val Thr Ala Ala Asp Thr Ala Val Tyr
                 85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 76
<211> LENGTH: 330
<212> TYPE: PRT
<213> ORGANISM: Homo sapiens

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 77
<211> LENGTH: 326
<212> TYPE: PRT
<213> ORGANISM: Homo sapiens

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
```

325

<210> SEQ ID NO 78
<211> LENGTH: 377
<212> TYPE: PRT
<213> ORGANISM: Homo sapiens

<400> SEQUENCE: 78

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365
```

```
Lys Ser Leu Ser Leu Ser Pro Gly Lys
    370                 375

<210> SEQ ID NO 79
<211> LENGTH: 327
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 80
<211> LENGTH: 110
<212> TYPE: PRT
<213> ORGANISM: Homo sapiens
```

<400> SEQUENCE: 80

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 81
<211> LENGTH: 126
<212> TYPE: PRT
<213> ORGANISM: Homo sapiens

<400> SEQUENCE: 81

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp
        115                 120                 125

<210> SEQ ID NO 82
<211> LENGTH: 128
<212> TYPE: PRT
<213> ORGANISM: Homo sapiens

<400> SEQUENCE: 82

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

<210> SEQ ID NO 83
<211> LENGTH: 154
<212> TYPE: PRT
<213> ORGANISM: Homo sapiens

<400> SEQUENCE: 83

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn
145                 150

<210> SEQ ID NO 84
<211> LENGTH: 162
<212> TYPE: PRT
<213> ORGANISM: Homo sapiens

<400> SEQUENCE: 84

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125
```

```
Thr Lys Asn Gln Val Ser Leu Thr Cys Leu Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys

<210> SEQ ID NO 85
<211> LENGTH: 167
<212> TYPE: PRT
<213> ORGANISM: Homo sapiens

<400> SEQUENCE: 85

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val
                165

<210> SEQ ID NO 86
<211> LENGTH: 192
<212> TYPE: PRT
<213> ORGANISM: Homo sapiens

<400> SEQUENCE: 86

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
```

```
            115                 120                 125
Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

<210> SEQ ID NO 87
<211> LENGTH: 204
<212> TYPE: PRT
<213> ORGANISM: Homo sapiens

<400> SEQUENCE: 87

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn
        195                 200

<210> SEQ ID NO 88
<211> LENGTH: 12
<212> TYPE: PRT
<213> ORGANISM: Homo sapiens

<400> SEQUENCE: 88

Tyr Thr Gln Lys Ser Leu Ser Leu Ser Pro Gly Lys
1               5                   10

<210> SEQ ID NO 89
<211> LENGTH: 205
<212> TYPE: PRT
<213> ORGANISM: Homo sapiens

<400> SEQUENCE: 89
```

-continued

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His
        195                 200                 205

<210> SEQ ID NO 90
<211> LENGTH: 217
<212> TYPE: PRT
<213> ORGANISM: Homo sapiens

<400> SEQUENCE: 90

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

```
                        165                 170                 175
Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 91
<211> LENGTH: 110
<212> TYPE: PRT
<213> ORGANISM: Homo sapiens

<400> SEQUENCE: 91

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110
```